(12) United States Patent
Bhat

(10) Patent No.: US 9,506,030 B2
(45) Date of Patent: *Nov. 29, 2016

(54) COMPOUNDS AND METHODS FOR ENHANCED CELLULAR UPTAKE

(71) Applicant: REGULUS THERAPEUTICS INC., San Diego, CA (US)

(72) Inventor: Balkrishen Bhat, San Deigo, CA (US)

(73) Assignee: Regulus Therapeutics Inc., San Diego, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/266,127

(22) Filed: Apr. 30, 2014

(65) Prior Publication Data

US 2015/0031130 A1   Jan. 29, 2015

Related U.S. Application Data

(60) Provisional application No. 61/818,441, filed on May 1, 2013, provisional application No. 61/818,447, filed on May 1, 2013, provisional application No. 61/822,115, filed on May 10, 2013, provisional application No. 61/895,708, filed on Oct. 25, 2013.

(51) Int. Cl.

| | | |
|---|---|---|
| C07H 17/02 | (2006.01) |
| C07H 21/02 | (2006.01) |
| C12N 5/00 | (2006.01) |
| C12N 5/02 | (2006.01) |
| C12N 5/071 | (2010.01) |
| C12N 15/11 | (2006.01) |
| C12N 15/113 | (2010.01) |

(52) U.S. Cl.
CPC ........... *C12N 5/0602* (2013.01); *C12N 15/111* (2013.01); *C12N 15/113* (2013.01); *C12N 2310/11* (2013.01); *C12N 2310/113* (2013.01); *C12N 2310/315* (2013.01); *C12N 2310/3231* (2013.01); *C12N 2310/351* (2013.01); *C12N 2501/999* (2013.01)

(58) Field of Classification Search
CPC . C12N 15/111; C12N 15/113; C12N 5/0602; C12N 2310/11; C12N 2310/113; C12N 2310/3231; C12N 2310/351; C12N 2310/315; C12N 2501/999
See application file for complete search history.

(56) References Cited

U.S. PATENT DOCUMENTS

| | | | |
|---|---|---|---|
| 5,994,517 A | 11/1999 | Ts'o et al. |
| 6,300,319 B1 | 10/2001 | Manoharan |
| 6,906,182 B2 | 6/2005 | Ts'o et al. |
| 7,491,805 B2 | 2/2009 | Vargeese et al. |
| 8,106,022 B2 | 1/2012 | Manoharan et al. |
| 8,129,515 B2 | 3/2012 | Esau et al. |
| 8,163,708 B2 | 4/2012 | Elmen et al. |
| 8,288,356 B2 | 10/2012 | Obad et al. |
| 8,313,772 B2 | 11/2012 | Rozema et al. |
| 8,361,980 B2 | 1/2013 | Kauppinen et al. |
| 8,404,659 B2 | 3/2013 | Kauppinen et al. |
| 8,426,554 B2 | 4/2013 | Rozema et al. |
| 8,450,467 B2 | 5/2013 | Manoharan et al. |
| 8,828,956 B2 | 9/2014 | Manoharan et al. |
| 9,157,083 B2 * | 10/2015 | Bhat ..................... C12N 15/111 |
| 9,309,513 B2 * | 4/2016 | Bhat ..................... C12N 15/111 |
| 2006/0148740 A1 | 7/2006 | Platenburg |
| 2009/0203132 A1 * | 8/2009 | Swayze ................ C07D 207/12 435/375 |
| 2010/0183639 A1 | 7/2010 | Uhlmann et al. |
| 2011/0243880 A1 | 10/2011 | Yurkovetskiy et al. |
| 2012/0122801 A1 | 5/2012 | Platenburg et al. |
| 2012/0157509 A1 | 6/2012 | Hadwiger et al. |
| 2013/0178512 A1 | 7/2013 | Manoharan et al. |
| 2014/0350090 A1 * | 11/2014 | Bhat ..................... C12N 15/111 514/44 R |

FOREIGN PATENT DOCUMENTS

| | | |
|---|---|---|
| WO | WO 95/30746 | 11/1995 |
| WO | WO 00/76554 | 12/2000 |
| WO | WO 01/25248 | 4/2001 |
| WO | WO 2004094595 | 11/2004 |
| WO | WO 2005013901 | 2/2005 |
| WO | WO 2005061710 | 7/2005 |
| WO | WO 2006078217 | 7/2006 |
| WO | WO 2006078278 | 7/2006 |
| WO | WO 2006112872 | 10/2006 |
| WO | WO 2007021896 | 2/2007 |
| WO | WO 2007112753 | 10/2007 |
| WO | WO 2007112754 | 10/2007 |
| WO | WO 2008091703 | 7/2008 |
| WO | WO 2008132234 | 11/2008 |
| WO | WO 2009043353 | 4/2009 |
| WO | WO 2009068033 | 6/2009 |
| WO | WO 2009073809 | 6/2009 |
| WO | WO 2010076248 | 7/2010 |
| WO | WO 2010122538 | 10/2010 |
| WO | WO 2011047312 | 4/2011 |

(Continued)

OTHER PUBLICATIONS

Leriche et al., "Cleavable linkers in chemical biology," Bioorg Med Chem., 2012, 20:571-582.

Regulus Theraputics Inc., "RG-101: A Potentially Disruptive Agent to the HCV Treatment Landscape," Presentation, Feb. 9, 2015, 18 pages.

(Continued)

*Primary Examiner* — Lawrence E Crane

(74) *Attorney, Agent, or Firm* — McNeill Baur PLLC

(57) ABSTRACT

Described herein are conjugated modified oligonucleotides that are complementary to a target RNA. The conjugate facilitates cellular uptake of the modified oligonucleotide, resulting improved potency.

25 Claims, 12 Drawing Sheets

(56) References Cited

FOREIGN PATENT DOCUMENTS

| WO | WO 2011130458 | 10/2011 |
|---|---|---|
| WO | WO 2012007477 | 1/2012 |
| WO | WO 2012083046 | 6/2012 |
| WO | WO 2012089352 | 7/2012 |
| WO | WO 2013033230 | 3/2013 |
| WO | WO 2013068348 | 5/2013 |
| WO | WO 2014076195 | 5/2014 |
| WO | WO 2014118267 | 8/2014 |
| WO | WO 2014118272 | 8/2014 |
| WO | WO 2014179445 | 11/2014 |
| WO | WO 2014179446 | 11/2014 |
| WO | WO 2014179620 | 11/2014 |

OTHER PUBLICATIONS

Xanthopoulos, Transcript of Oral Presentation, 12th Annual Needham Healthcare Conference, May 1, 2013, 9 pages.
Bhat et al., "RG-101, a GalNAC-conjugated anti-miR employing a unique mechanism of action by targeting host factor microRNA-122 (miR-122), demonstrates potent activity and reduction of HCV in preclinical studies," AASLD Abstracts, Abstract #LB-28, Hepatology, 2013, 58:1393A.
Bhat et al., "RG-101, a GalNAC-conjugated anti-miR employing a unique mechanism of action by targeting host factor microRNA-122 (miR-122), demonstrates potent activity and reduction of HCV in preclinical studies," 64th Annual Meeting AASLD, Washington D.C. Nov. 3, 2013, 1 page.
Biessen et al., "Targeted delivery of oligodeoxynucleotides to parenchymal liver cells in vivo," Biochem. J., 1999, 340: 783-792.
Biton et al., "DNA photocleavage by DNA and DNA-LNA amino acid-dye conjugates," Bioconjug Chem., 2010, 21:616-621, includes supplemental data, (7 pages).
Duff et al., "Intrabody-Specific Delivery of Antisense Conjugates in Animals: Ligand-Linker-Antisense Oligomer Conjugates," Methods Enzymol., 2000, 313: 297-321.
Gagnon et al., "Antisense and antigene inhibition of gene expression by cell-permeable oligonucleotide-oligospermine conjugates," J Am Chem Soc., 2011, 133:8404-8407.
Gibson et al., "Targeting microRNAs and Biological Networks: An Innovative Approach to Treat Disease," Presentation, Tides Conference, May 15, 2013, 31 pages.
Godeau et al., "Lipid-conjugated oligonucleotides via "click chemistry" efficiently inhibit hepatitis C virus translation," J Med Chem., 2008, 51:4374-4376, includes supplemental data (19 pages).
Hangeland et al., "Cell-Type Specific and Ligand Specific Enhancement of Cellular Uptake of Oligodeoxynucleoside-Methylphosphonates Covalently Linked with a Neoglycopeptide, YEE(ah-GalNAc)$_3$," Bioconjug Chem., 1995, 6:695-701.
Haussecker et al., "miR-122 Continues to Blaze the Trail for MicroRNA Therapeutics," Molecular Therapy, 2010, 18:240-242.
Hogan et al., "Anti-miRs Competitively Inhibit microRNAs in Argonaute Complexes," PLoS One, 2014, 9:e100951, 11 pages.
Horwich et al., "Design and delivery of antisense oligonucleotides to block microRNA function in cultured *Drosophila* and human cells," Nature Protocols, 2008, 3:1537-1549.
Karskela et al., "Synthesis of Cellular Uptake of Fluorescently Labeled Multivalent Hyaluronan Disaccharide Conjugates of Oligonucleotide Phosphorothioates," Bioconjugate Chem., 2008, 19:2549-2558.
Katajisto et al., "Solid-Phase Synthesis of Multiantennary Oligonucleotide Glycoconjugates Utilizing On-Support Oximation," Bioconjugate Chem., 2004, 15:890-896.
Lehmann et al., "Synthesis and properties of bile acid phosphoramidites 5'-tethered to antisense oligodeoxynucleotides against HCV," Bioorg Med Chem., 2001, 9:1827-1835.

Maier et al., "Synthesis of Antisense Oligonucleotides Conjugated to a Multivalent Carbohydrate Cluster for Cellular Targeting," Bioconjugate Chem., 2003, 14:18-29.
Makino et al., "Intravenous injection with antisense oligodeoxynucleotides against angiotensinogen decreases blood pressure in spontaneously hypertensive rats," Hypertension, 1998, 31:1166-1170.
Manoharan, "Oligonucleotide Conjugates as Potential Antisense Drugs with Improved Uptake, Biodistribution, Targeted Delivery, and Mechanism of Action," Antisense Nucl. Acid Drug Develop., 2002, 12:103-128.
Merwin et al., "Targeted Delivery of DNA Using YEE(GalNAcAH)$_3$, a Synthetic Glycopeptide Ligand for the Asialoglycoprotein Receptor," Bioconjug Chem., 1994, 5:612-620.
Rajur et al., "Covalent protein-oligonucleotide conjugates for efficient delivery of antisense molecules," Bioconjug Chem., 1997, 8:935-940.
Raouane et al., "Synthesis, characterization, and in vivo delivery of siRNA-squalene nanoparticles targeting fusion oncogene in papillary thyroid carcinoma," J Med Chem, 2011, 54:4067-4076, includes supplemental data (10 pages).
Regulus Thereapeutics Inc., "Regulus Provides Update on 'Road to the Clinic' Strategy and Reports First Quarter 2013 Financial Results and Recent Highlights," Press Release, May 14, 2013, 3 pages.
Regulus Thereapeutics Inc., "Targeting microRNAs and Biological Networks: An Innovative Approach to Treat Disease," Presentation, Tides Conference, May 15, 2013, 31 pages.
Regulus Thereapeutics Inc., "Positive Preclinical Profile of RG-101, a GalNAc-conjugated anti-miR Targeting microRNA-122, Supports Clinical Development for the Treatment of HCV," Press Release, Nov. 4, 2013, 2 pages.
Regulus Thereapeutics Inc., "RG-101 Human Proof-of-Concept," Presentation, Oct. 22, 2014, 23 pages.
Regulus Thereapeutics Inc., "A Single Subcutaneous Dose of 2mg/kg of RG-101, Regulus' Wholly-Owned, GalNac-Conjugated anti-miR Targeting microRNA-122, Demonstrates 4.1 log10 Mean Viral Load Reduction as Monotherapy at Day 29 in Patients with Varied HCV Genotypes and Treatment History," Press Release, Oct. 22, 2014, 3 pages.
Sliedregt et al., "Design and Synthesis of Novel Amphiphilic Dendritic Galactosides for Selective Targeting of Liposomes to the Hepatic Asialoglycoprotein Receptor," 1999, 42: 609-618.
Spinelli et al., "Glycoclusters on oligonucleotide and PNA scaffolds: synthesis and applications," Chem Soc Rev., 2013, 42:4557-4573.
Tyagi et al., "Molecular beacons: probes that fluoresce upon hybridization," Nat Biotechnol., 1996, 14:303-308.
Tripathi et al., "The Nuclear-Retained Noncoding RNA MALAT1 Regulates Alternative Splicing by Modulating SR Splicing Factor Phosphorylation," Molecular Cell, 2010, 39:925-938.
Van Rooij et al., "Developing MicroRNA Therapeutics," Circ Res., 2012, 110:496-507.
Zatsepin et al., "Synthesis and Applications of Oligonucleotide—Carbohydrate Conjugate," Chemistry & Biodiversity, Helvetica Chimica Acta, 2004, 1(10):1413-1415.
Zheng et al., "Distribution and anti-HBV effects of antisense oligodeoxynucleotides conjugated to galactosylated poly-L-lysine," World J Gastroenterol., 2003, 9:1251-1255.
Zhu et al., "Site-specific delivery of oligonucleotides to hepatocytes after systemic administration," Bioconjug Chem, 2008, 19:290-298.
Zhu et al., "Targeted Delivery of siRNA to Hepatocytes and Hepatic Stellate Cells by Bioconjugation," Bioconjug Chem., 2010, 21:2119-2127.
International Search Report and Written Opinion for PCT/US2014/036136, mailed Oct. 13, 2014, 12 pages.
International Search Report and Written Opinion for PCT/US2014/036137, mailed Dec. 15, 2014, 20 pages.

\* cited by examiner

A

B

COMPOUNDS AND METHODS FOR ENHANCED CELLULAR UPTAKE

This application claims the benefit of U.S. Provisional Application No. 61/818,441, filed May 1, 2013; 61/818,447, filed May 1, 2013; 61/822,115, filed May 10, 2013; and 61/895,708, filed Oct. 25, 2013; each of which is incorporated by reference herein in its entirety for any purpose.

FIELD OF INVENTION

Provided herein are compounds and methods for enhanced cellular uptake of modified oligonucleotides.

DESCRIPTION OF RELATED ART

Strategies for therapeutic modulation of RNA function often employ the use of antisense oligonucleotides that are designed to bind to the RNA target through Watson-Crick base pairing, and, once bound to the target, modulate its function. Such antisense oligonucleotides are chemically modified to impart desired pharmacokinetic and pharmacodynamic properties to the oligonucleotides. Modified oligonucleotides may modulate a target RNA through a variety of mechanisms, including mechanisms that involve binding of the modified oligonucleotide to the target RNA and interference with its function without promoting degradation of the RNA (e.g., steric hindrance), as well as mechanisms that do promote degradation of the RNA after binding of the modified oligonucleotide, by activities of enzymes such as RNaseH or Argonaute 2. Numerous types of RNAs may be selected as targets of modified oligonucleotides, including messenger RNAs, pre-messenger RNAs, and non-coding RNAs such as microRNAs.

MicroRNAs (microRNAs), also known as "mature microRNA" are small (approximately 18-24 nucleotides in length), non-coding RNA molecules encoded in the genomes of plants and animals. In certain instances, highly conserved, endogenously expressed microRNAs regulate the expression of genes by binding to the 3'-untranslated regions (3'-UTR) of specific mRNAs. More than 1000 different microRNAs have been identified in plants and animals. Certain mature microRNAs appear to originate from long endogenous primary microRNA transcripts (also known as pri-microRNAs, pri-mirs, pri-miRs or pri-pre-microRNAs) that are often hundreds of nucleotides in length (Lee, et al., EMBO J., 2002, 21(17), 4663-4670).

SUMMARY OF INVENTION

Provided herein are compounds comprising modified oligonucleotides covalently attached to a conjugate moiety. In certain embodiments, a compound has the structure $L_n$-linker-X-MO, wherein each L is, independently, a ligand and n is from 1 to 10; X is a phosphodiester linkage or a phosphorothioate linkage; and MO is a modified oligonucleotide.

In certain embodiments, a compound has the structure $L_n$-linker-$X_1$—$N_m$—$X_2$-MO, wherein each L is, independently, a ligand and n is from 1 to 10; each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, a compound has the structure $L_n$-linker-X—$N_m$—Y-MO, wherein each L is, independently, a ligand and n is from 1 to 10; each N is, independently, a modified or unmodified nucleoside and m is from 1 to 5; X is a phosphodiester linkage or a phosphorothioate linkage; Y is a phosphodiester linkage; and MO is a modified oligonucleotide.

In certain embodiments, a compound has the structure $L_n$-linker-Y—$N_m$—Y-MO, wherein each L is, independently, a ligand and n is from 1 to 10; each N is, independently, a modified or unmodified nucleoside and m is from 1 to 5; each Y is a phosphodiester linkage; and MO is a modified oligonucleotide.

In certain embodiments, if n is greater than 1, $L_n$-linker has the structure:

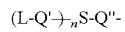

wherein each L is, independently, a ligand; n is from 1 to 10; S is a scaffold; and Q' and Q" are, independently, linking groups.

In certain embodiments, Q' and Q" are each independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

In certain embodiments, a scaffold links 2, 3, 4, or 5 ligands to a modified oligonucleotide. In certain embodiments, a scaffold links 3 ligands to a modified oligonucleotide.

In certain embodiments, a compound has the structure:

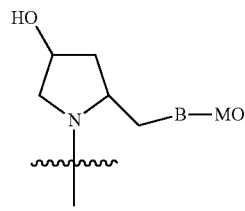

wherein:
B is selected from —O—, —S—, —N($R^N$)—, —Z—P(Z')(Z")O—, —Z—P(Z')(Z")O—$N_m$—X—, and —Z—P(Z')(Z")O—$N_m$—Y—;
MO is a modified oligonucleotide;
$R^N$ is selected from H, methyl, ethyl, propyl, isopropyl, butyl, and benzyl;
Z, Z', and Z" are each independently selected from O and S;
each N is, independently, a modified or unmodified nucleoside;
m is from 1 to 5;
X is selected from a phosphodiester linkage and a phosphorothioate linkage;
Y is a phosphodiester linkage; and
the wavy line indicates the connection to the rest of the linker and ligand(s).

In certain embodiments, X is a phosphodiester linkage.
In certain embodiments, n is from 1 to 5, 1 to 4, 1 to 3, or 1 to 2. In certain embodiments, n is 3.
In certain embodiments, at least one ligand is a carbohydrate.
In certain embodiments, at least one ligand is selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-mannofuranose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, N-acetylgalactosamine.

In certain embodiments, at least one ligand is selected from N-acetylgalactosamine, galactose, galactosamine, N-formylgalactosamine, N-propionyl-galactosamine, N-n-butanoylgalactosamine, and N-iso-butanoyl-galactosamine.

In certain embodiments, each ligand is N-acetylgalactosamine.

In certain embodiments, a compound has the structure:

purine nucleobase is independently selected from adenine, guanine, hypoxanthine, xanthine, and 7-methylguanine. In certain embodiments, N″ is a β-D-deoxyriboadenosine or a β-D-deoxyriboguanosine.

In certain embodiments, where p is 1, 2, 3, or 4, at least one N′ comprises a pyrimidine nucleobase. In certain embodiments, N″ comprises a pyrimidine nucleobase. In certain embodiments, each pyrimidine nucleobase is independently selected from cytosine, 5-methylcytosine, thymine, uracil, and 5,6-dihydrouracil.

In certain embodiments, p is 1, N′ and N″ are each a β-D-deoxyriboadenosine, and N′ and N″ are linked by a phosphodiester internucleoside linkage. In certain embodiments, p is 1, N′ and N″ are each a β-D-deoxyriboadenosine, and N′ and N″ are linked by a phosphodiester internucleoside linkage. In certain embodiments, p is 1, N′ and N″ are each a β-D-deoxyriboadenosine, and N′ and N″ are linked by a phosphorothioate internucleoside linkage.

(I)

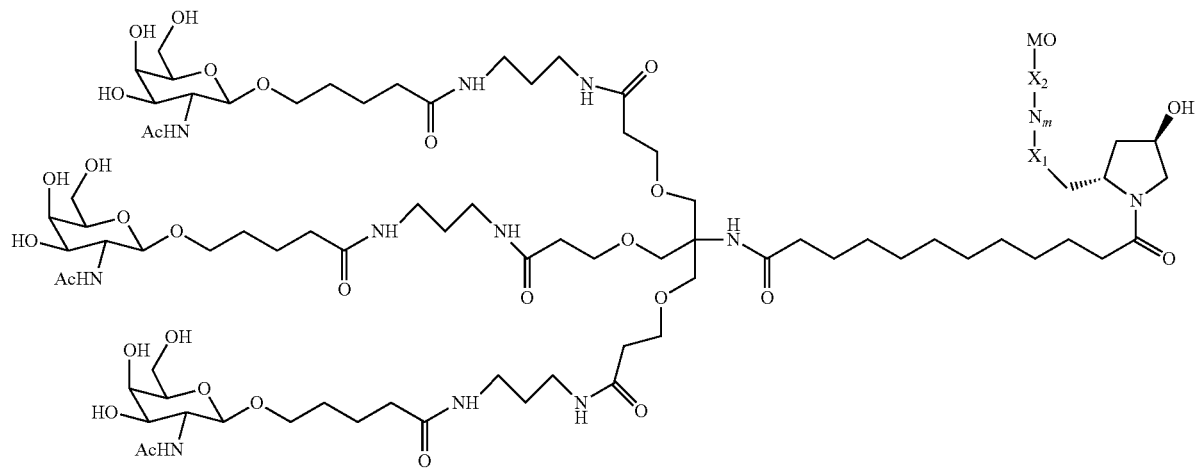

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, at least one of $X_1$ and $X_2$ is a phosphodiester linkage. In certain embodiments, each of $X_1$ and $X_2$ is a phosphodiester linkage.

In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage.

In certain embodiments, $N_m$ is $N'_p N''$, wherein each N′ is, independently, a modified or unmodified nucleoside and p is from 0 to 4; and N″ is a nucleoside comprising an unmodified sugar moiety. In certain embodiments, p is 0. In certain embodiments, p is 1, 2, 3, or 4.

In certain embodiments, each N′ comprises an unmodified sugar moiety. In certain embodiments, each unmodified sugar moiety is, independently, a β-D-ribose or a β-D-deoxyribose. In certain embodiments, N″ comprises a purine nucleobase. In certain embodiments, at least one N′ comprises a purine nucleobase. In certain embodiments, each In any of the embodiments described herein, the sugar moiety of each N is independently selected from a β-D-ribose, a β-D-deoxyribose, a 2′-O-methoxy sugar, a 2′-O-methyl sugar, a 2′-fluoro sugar, and a bicyclic sugar moiety. In certain embodiments, each bicyclic sugar moiety is independently selected from a cEt sugar moiety, an LNA sugar moiety, and an ENA sugar moiety. In certain embodiments, a cEt sugar moiety is an S-cEt sugar moiety. In certain embodiments, a cEt sugar moiety is an R-cEt sugar moiety. In any embodiments described herein, the sugar moiety of each N is independently selected from β-D-ribose, a β-D-deoxyribose, and a 2′-fluoro sugar.

In any of the embodiments provided herein, a compound comprises a modified oligonucleotide having a nucleobase sequence that is complementary to a target RNA. In certain embodiments, the target RNA is a microRNA. In certain embodiments, the target RNA is a messenger RNA. In certain embodiments, the target RNA is a pre-messenger RNA. In certain embodiments, the target RNA is a long non-coding RNA. In certain embodiments, the modified oligonucleotide is hybridized to a second modified oligonucleotide, wherein the nucleobase sequence of the second modified oligonucleotide is complementary to the nucleobase sequence of the modified oligonucleotide. In certain embodiments, the target RNA is a human target RNA.

In certain embodiments, the nucleobase sequence of the modified oligonucleotide is at least 90%, at least 91%, at least 92%, at least 93%, at least 94%, at least 95%, at least 96%, at least 97%, at least 98%, at least 99%, or 100% complementary to the nucleobase sequence of the target RNA.

In certain embodiments, the nucleobase sequence of the modified oligonucleotide is partially identical to the nucleobase sequence of a microRNA. In certain embodiments, the nucleobase sequence of the modified oligonucleotide is at least 90%, at least 95% or 100% identical to the nucleobase sequence of the microRNA.

In certain embodiments, the microRNA is a human microRNA.

In certain embodiments, the modified oligonucleotide consists of 7 to 10, 7 to 12, 8 to 25, 12 to 25, 15 to 25, 15 to 22, or 17 to 22 linked nucleosides.

In certain embodiments, the modified oligonucleotide comprises at least one nucleoside with a modified sugar moiety. In certain embodiments, each nucleoside of the modified oligonucleotide comprises a modified sugar moiety. In certain embodiments, the modified oligonucleotide comprises a plurality of nucleosides with a modified sugar moiety, and a plurality of nucleosides with an unmodified sugar moiety. In certain embodiments, each modified sugar moiety is the same modified sugar moiety. In certain embodiments, each modified sugar moiety is independently selected from a 2'-O-methyl sugar moiety, a 2'-O-methoxyethyl sugar moiety, a 2'-fluoro sugar moiety, and a bicyclic sugar moiety. In certain embodiments, each bicyclic sugar moiety is independently selected from a cEt sugar moiety and an LNA sugar moiety. In certain embodiments, each unmodified sugar moiety is independently selected from a β-D-deoxyribose and a β-D-ribose. In certain embodiments, the modified oligonucleotide comprises a plurality of non-bicyclic nucleosides and a plurality of bicyclic nucleosides. In certain embodiments, each non-bicyclic nucleoside has the same type of sugar moiety. In certain embodiments, at least two non-bicyclic nucleosides comprise sugar moieties that are different from one another. In certain embodiments, each non-bicyclic nucleoside is independently selected from a β-D-deoxyribonucleoside, a β-D-ribonucleoside, 2'-O-methyl nucleoside, a 2'-O-methoxyethyl nucleoside, and a 2'-fluoronucleoside. In certain embodiments, each bicyclic nucleoside has the same type of sugar moiety. In certain embodiments, at least two bicyclic nucleosides have sugar moieties that are different from one another. In certain embodiments, each bicyclic nucleoside is independently selected from bicyclic nucleoside is selected from a cEt nucleoside, and LNA nucleoside, and an ENA nucleoside. In certain embodiments, each cEt nucleoside is an S-cEt nucleoside.

In certain embodiments, at least one linkage of the modified oligonucleotide is a modified internucleoside linkage. In certain embodiments, each internucleoside linkage of the modified oligonucleotide is a modified internucleoside linkage. In certain embodiments, a modified internucleoside linkage is a phosphorothioate internucleoside linkage.

In certain embodiments, a modified oligonucleotide comprises a modified nucleobase.

In certain embodiments, a modified oligonucleotide comprises a 5-methylcytosine. In certain embodiments, each cytosine of the modified oligonucleotide is a 5-methylcytosine.

Provided herein are methods comprising contacting a cell with any of the compounds provided herein. In certain embodiments, the cell is in vivo. In certain embodiments, the cell is in vitro. In certain embodiments, the cell is a liver cell. In certain embodiments, the cell is a hepatocyte.

Provided herein are methods comprising improving the potency of a modified oligonucleotide, the method comprising a. forming a compound having the structure $L_n$-linker-X—$N_m$—X-MO, wherein each L is, independently, a ligand and n is from 1 to 10; each N is, independently, a modified or unmodified nucleoside and m is from 1 to 5; each X is, independently, a phosphodiester linkage or a phosphorothioate linkage; and MO is a modified oligonucleotide; and b. thereby improving the potency of the modified oligonucleotide, relative to the unconjugated modified oligonucleotide.

Provided herein is a process of making a compound having the structure:

(I)

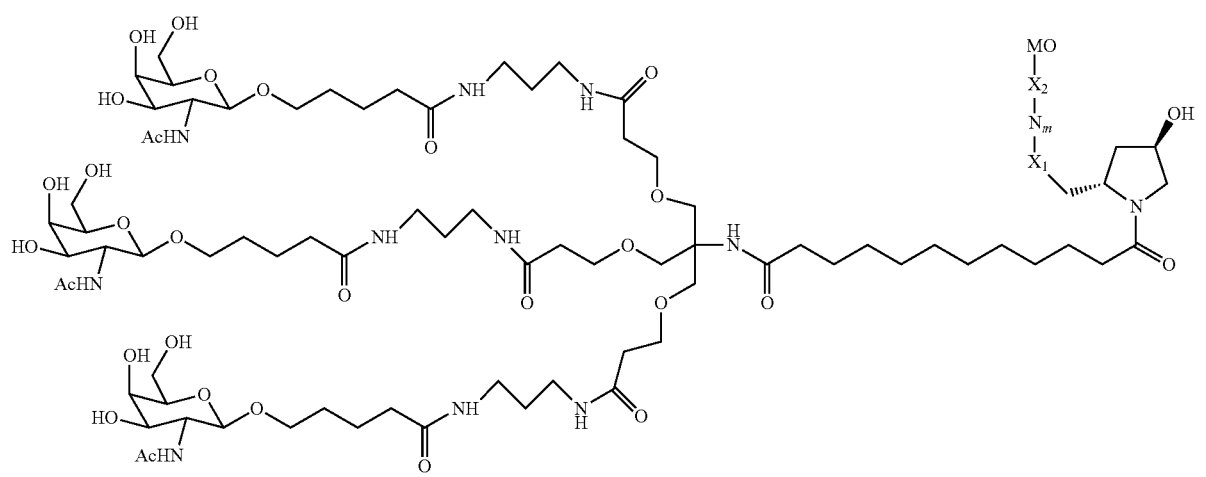

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide, the process comprising the steps of:

providing a solid support containing a conjugate as shown in formula IV;

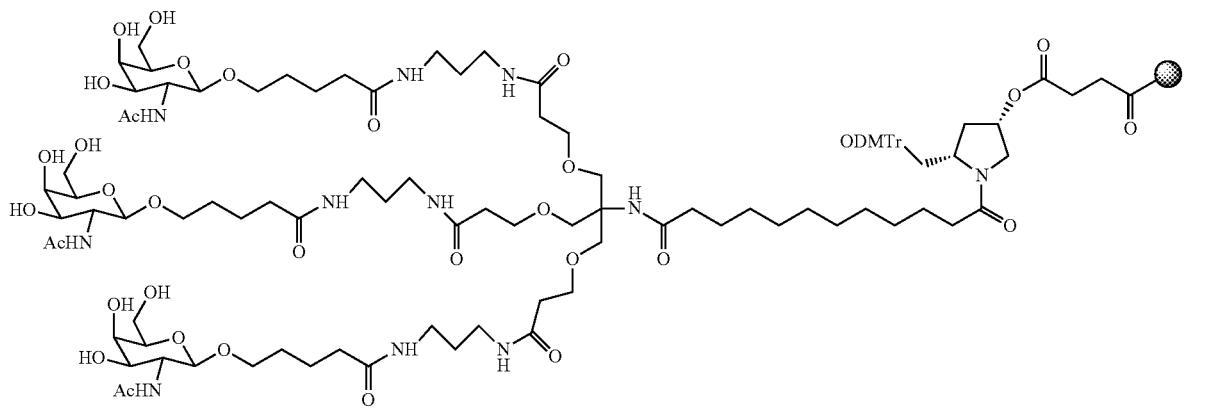

(IV)

deprotecting the DMT group under conditions effective to produce a reactive hydroxyl;
performing sequential phosphoramidite coupling steps to form $N_m$;
performing sequential phosphoramidite coupling steps to form the modified oligonucleotide; and
releasing the conjugated modified oligonucleotide from the solid support.

Provided herein are methods comprising administering to a subject a compound provided herein. In certain embodiments, the subject is a human. In certain embodiments, the compound is present in a pharmaceutical composition. In certain embodiments, the subject has a disease associated with a target RNA that is present in a liver cell.

Any compound provided herein may be for use in therapy.

DETAILED DESCRIPTION

Figure 1:
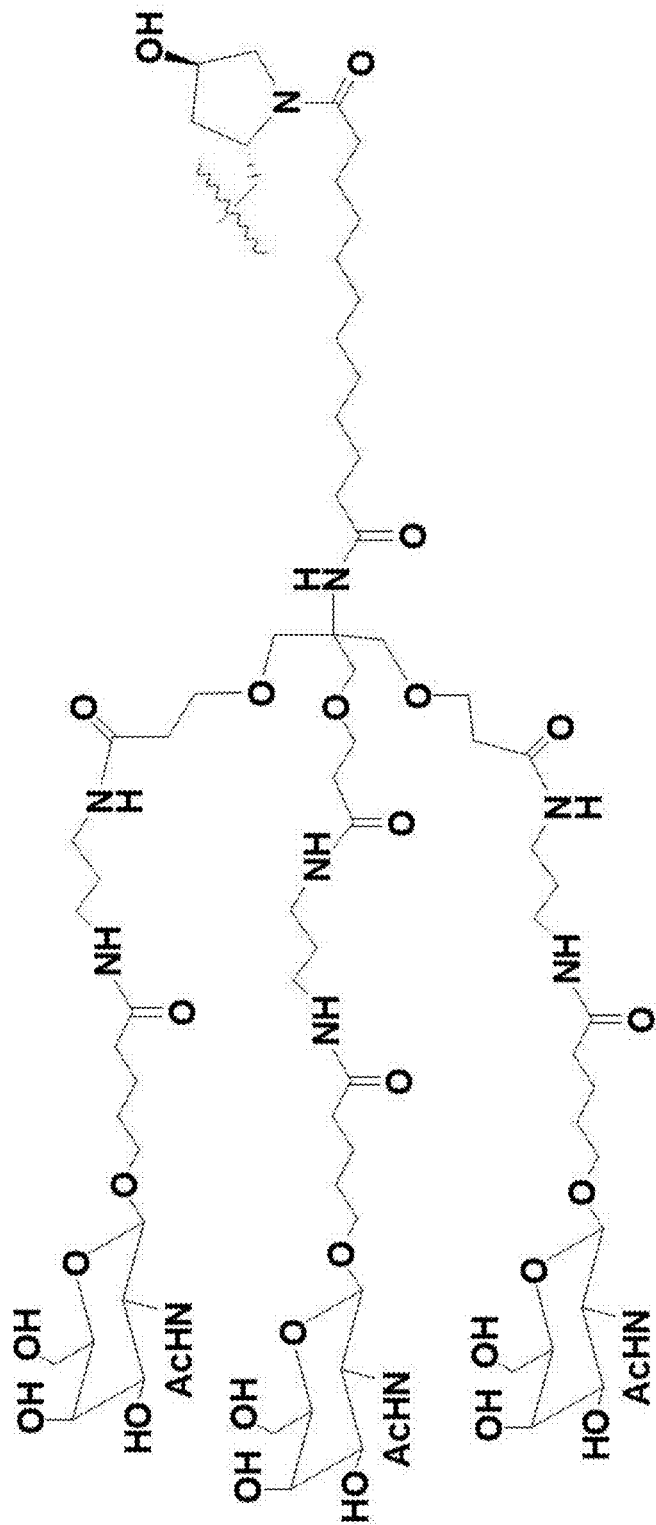
FIG. 1. Structure of conjugate moiety comprising three GalNAc ligands.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Target nucleic acid" means a nucleic acid to which an oligonucleotide is designed to hybridize.
"Target RNA" means an RNA to which an oligonucleotide is complementary.
"Targeting" means the process of design and selection of nucleobase sequence that will hybridize to a target nucleic acid.

"Targeted to" means having a nucleobase sequence that will allow hybridization to a target nucleic acid.

"Target engagement" means the interaction of an oligonucleotide with the microRNA to which it is complementary, in a manner that changes the activity, expression or level of the microRNA. In certain embodiments, target engagement means an anti-miR interacting with the microRNA to which it is complementary, such that the activity of the microRNA is inhibited.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"5' target site" means the nucleobase of a target nucleic acid which is complementary to the 3'-most nucleobase of a particular oligonucleotide.

"3' target site" means the nucleobase of a target nucleic acid which is complementary to the 5'-most nucleobase of a particular oligonucleotide.

"Region" means a portion of linked nucleosides within a nucleic acid. In certain embodiments, an oligonucleotide has a nucleobase sequence that is complementary to a region of a target nucleic acid. For example, in certain embodiments an oligonucleotide is complementary to a region of a microRNA stem-loop sequence. In certain embodiments, an oligonucleotide is fully complementary to a region of a microRNA stem-loop sequence.

"Segment" means a smaller or sub-portion of a region.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microrna.sanger.ac.uk/). In certain embodiments, microRNA is abbreviated as "microRNA" or "miR."

"Pre-microRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature microRNA sequence. Pre-microRNA sequences and stem-loop sequences may overlap. Examples of stem-loop sequences are found in the microRNA database known as miRBase (http://microrna.sanger.ac.uk/).

"Pri-microRNA" or "pri-miR" means a non-coding RNA having a hairpin structure that is a substrate for the double-stranded RNA-specific ribonuclease Drosha.

"microRNA precursor" means a transcript that originates from a genomic DNA and that comprises a non-coding, structured RNA comprising one or more microRNA sequences. For example, in certain embodiments a microRNA precursor is a pre-microRNA. In certain embodiments, a microRNA precursor is a pri-microRNA.

"microRNA-regulated transcript" means a transcript that is regulated by a microRNA.

"Monocistronic transcript" means a microRNA precursor containing a single microRNA sequence.

"Polycistronic transcript" means a microRNA precursor containing two or more microRNA sequences.

"Seed sequence" means a nucleobase sequence comprising from 6 to 8 contiguous nucleobases of nucleobases 1 to 9 of the 5'-end of a mature microRNA sequence.

"Seed match sequence" means a nucleobase sequence that is complementary to a seed sequence, and is the same length as the seed sequence.

"Anti-miR" means an oligonucleotide having nucleobase sequence complementary to a microRNA. In certain embodiments, an anti-miR is a modified oligonucleotide.

"Anti-miR-X" where "miR-X" designates a particular microRNA, means an oligonucleotide having a nucleobase sequence complementary to miR-X. In certain embodiments, an anti-miR-X is fully complementary to miR-X. In certain embodiments, an anti-miR-X is at least 80%, at least 85%, at least 90%, or at least 95% complementary to miR-X. In certain embodiments, an anti-miR-X is a modified oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Gapmer" means a modified oligonucleotide having an internal region of linked β-D-deoxyribonucleosides positioned between two external regions of linked nucleosides, where each nucleoside of each external region comprises a modified sugar moiety. The β-D-deoxyribonucleosides may or may not have a modified nucleobase.

"Gap" is an internal region of a gapmer that is positioned between the external regions.

"Wing" is an external region of a gapmer that is adjacent to a 5' or 3' end of the internal region of the gapmer.

"Symmetric gapmer" means each nucleoside of each external region comprises the same sugar modification.

"Asymmetric gapmer" means each nucleoside of one external region comprises a first sugar modification, and each nucleoside of the other external region comprises a second sugar modification.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybrizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary to a microRNA, i.e. each nucleobase of the oligonucleotide is complementary to a nucleobase at a corresponding position in the microRNA. In certain embodiments, an oligonucleotide wherein each nucleobase has complementarity to a nucleobase within a region of a microRNA stem-loop sequence is fully complementary to the microRNA stem-loop sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"Oligomeric compound" means a compound that comprises a plurality of linked monomeric subunits. Oligomeric compounds included oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar, and unmodified nucleobase. A modified nucleoside may have a modified sugar and a modified nucleobase. A modified nucleoside may have a natural sugar and a modified nucleobase.

"2'-modified nucleoside" means a nucleoside comprising a sugar with any modification at the position equivalent to the 2' position of the furanosyl ring as the positions are numbered in 2-deoxyribose or ribose. It is to be understood that 2'-modified nucleosides include, without limitation, nucleosides comprising bicyclic sugar moieties.

"Modified internucleoside linkage" means any change from a naturally occurring internucleoside linkage.

"Phosphorothioate internucleoside linkage" means a linkage between nucleosides where one of the non-bridging atoms is a sulfur atom.

A "phosphorothioate linkage" means a linkage between two chemical moieties having the same structure as a phosphorothioate internucleoside linkage, e.g., —OP(O)(S)O—.

A "phosphodiester linkage" means a linkage between two chemical moieties having the same structure as a phosphodiester internucleoside linkage, e.g., —OP(O)$_2$O—.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Modified nucleobase" means any nucleobase that is not an unmodified nucleobase.

"Furanosyl" means a structure comprising a 5-membered ring consisting of four carbon atoms and one oxygen atom.

"Naturally occurring furanosyl" means a ribofuranosyl as found in naturally occurring RNA or a deoxyribofuranosyl as found in naturally occurring DNA.

"Sugar moiety" means a naturally occurring furanosyl or a modified sugar moiety.

"Modified sugar moiety" means a substituted sugar moiety or a sugar surrogate.

"Substituted sugar moiety" means a furanosyl that is not a naturally occurring furanosyl. Substituted sugar moieties include, but are not limited to sugar moieties comprising modifications at the 2'-position, the 5'-position and/or the 4'-position of a naturally occurring furanosyl. Certain substituted sugar moieties are bicyclic sugar moieties.

"Sugar surrogate" means a structure that does not comprise a furanosyl and that is capable of replacing the naturally occurring furanosyl of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

"β-D-deoxyribose" means a naturally occurring DNA sugar moiety.

"β-D-ribose" means a naturally occurring RNA sugar moiety.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a ($CH_2$)—O bridge between the 4' and 2' furanose ring atoms.

"ENA sugar moiety" means a substituted sugar moiety comprising a ($CH_2$)$_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $CH(CH_3)$—O bridge is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methyl nucleoside" means a modified nucleoside having a 2'-O-methyl sugar modification.

"2'-O-methoxyethyl nucleoside" means a modified nucleoside having a 2'-O-methoxyethyl sugar modification. A 2'-O-methoxyethyl nucleoside may comprise a modified or unmodified nucleobase.

"2'-fluoro nucleoside" means a modified nucleoside having a 2'-fluoro sugar modification. A 2'-fluoro nucleoside may comprise a modified or unmodified nucleobase.

"Bicyclic nucleoside" means a modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"Non-bicyclic nucleoside" means a nucleoside that has a sugar other than a bicyclic sugar. In certain embodiments, a non-bicyclic nucleoside comprises a naturally occurring sugar. In certain embodiments, a non-bicyclic nucleoside comprises a modified sugar. In certain embodiments, a non-bicyclic nucleoside is a β-D-deoxyribonucleoside. In certain embodiments, a non-bicyclic nucleoside is a 2'-O-methoxyethyl nucleoside.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

"Motif" means a pattern of modified and/or unmodified nucleobases, sugars, and/or internucleoside linkages in an oligonucleotide. In certain embodiments, a motif is a nucleoside pattern.

"Nucleoside pattern" means a pattern of nucleoside modifications in an oligonucleotide or a region thereof. A nucleoside pattern is a motif that describes the arrangement of nucleoside modifications in an oligonucleotide.

"Stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

"Stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

"Stabilizing internucleoside linkage" means an internucleoside linkage that provides improved nuclease stability to an oligonucleotide relative to that provided by a phosphodiester internucleoside linkage. In one embodiment, a stabilizing internucleoside linkage is a phosphorothioate internucleoside linkage.

A "linking group" as used herein refers to an atom or group of atoms that attach a first chemical entity to a second chemical entity via one or more covalent bonds.

A "linker" as used herein, refers to an atom or group of atoms that attach one or more ligands to a modified or unmodified nucleoside via one or more covalent bonds. The modified or unmodified nucleoside may be part of a modified oligonucleotide as described herein, or may be attached to a modified oligonucleotide through a phosphodiester or phosphorothioate bond. In some embodiments, the linker attaches one or more ligands to the 3' end of a modified oligonucleotide. In some embodiments, the linker attaches one or more ligands to the 5' end of a modified oligonucleotide. In some embodiments, the linker attaches one or more ligands to a modified or unmodified nucleoside that is attached to the 3' end of a modified oligonucleotide. In some embodiments, the linker attaches one or more ligands to a modified or unmodified nucleoside that is attached to the 5' end of a modified oligonucleotide. When the linker attaches one or more ligands to the 3' end of a modified oligonucleotide or to a modified or unmodified nucleoside attached to the 3' end of a modified oligonucleotide, in some embodiments, the attachment point for the linker may be the 3' carbon of a modified or unmodified sugar moiety. When the linker attaches one or more ligands to the 5' end of a modified oligonucleotide or to a modified or unmodified nucleoside attached to the 5' end of a modified oligonucleotide, in some embodiments, the attachment point for the linker may be the 5' carbon of a modified or unmodified sugar moiety.

"Subject" means a human or non-human animal selected for treatment or therapy.

"Subject in need thereof" means the state in which a subject is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion.

Parenteral administration includes, but is not limited to, subcutaneous administration, intravenous administration, or intramuscular administration.

"Subcutaneous administration" means administration just below the skin.

"Intravenous administration" means administration into a vein.

"Intracardial administration" means administration into the heart. In certain embodiments, intracardial administration occurs by way of a catheter. In certain embodiments, intracardial administration occurs by way of open heart surgery.

"Pulmonary administration" means administration to the lungs.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Improved liver function" means the change in liver function toward normal limits. In certain embodiments, liver function is assessed by measuring molecules found in a subject's blood. For example, in certain embodiments, improved liver function is measured by a reduction in blood liver transaminase levels.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

Overview

The activity of a modified oligonucleotide is based on the specific hybridization event that occurs between a modified oligonucleotide and its target RNA and produces a desired pharmacological endpoint. In order for this to occur, certain pharmacokinetic processes must take place, for example, delivery of an intact drug to the target cell or tissue, and entry of the modified oligonucleotide into the cell containing the target RNA. Modified oligonucleotides may be conjugated to one or more moieties which improve delivery to the target cell or tissue and/or cellular uptake of the oligonucleotide, ultimately resulting in enhanced potency. For example, increased cellular uptake of compounds may be achieved by utilizing conjugates that are ligands for cell-surface receptors. The binding of a ligand conjugated to an exogenous molecule (e.g., a drug) to its cell surface receptor leads to receptor-mediated endocytosis of the conjugated molecule, thereby facilitating transmembrane transport of the exogenous molecule. For example, the targeted delivery to hepatocyte cells may be achieved by covalently attaching a conjugate comprising a carbohydrate moiety to a modified oligonucleotide. Upon recognition and binding of the carbohydrate moiety by the asialoglycoprotein receptor present on the surface of a hepatocyte cell, the conjugated modified oligonucleotide is transported across the cell membrane into the hepatocyte. By improving delivery in this manner, the potency of the modified oligonucleotide can be enhanced, as a lower does of compound is required to achieve the desired pharmacological endpoint.

Certain conjugates described herein have the advantage of providing improved delivery to target cell types and also being cleavable in vivo to produce the unconjugated modified oligonucleotide upon in vivo administration. As described above, in vivo targeting to a specific tissue or cell type may be enhanced by using a conjugate moiety. Once the conjugated modified oligonucleotide reaches its site of action, however, the presence of all or part of the covalently-linked conjugate moiety may alter the activity of certain conjugated modified oligonucleotides or may impact the analyses required to understand certain pharmacokinetic properties of the modified oligonucleotide, such as half-life in the target cell. As such, it may be desirable to administer a compound comprising a modified oligonucleotide attached to a conjugate moiety that is sufficiently stable to improve cellular uptake, but also allows for cleavage of the conjugate moiety once the compound has been internalized by the target cell. Accordingly, provided herein are compounds comprising a modified oligonucleotide linked to a cleavable conjugate moiety, which improve the potency of the modified oligonucleotide and permit partial or completed release of the modified oligonucleotide in its unconjugated form.

Certain Conjugated Compounds

In certain embodiments, a compound provided herein comprises a conjugate moiety linked to the 5' terminus or the 3' terminus of a modified oligonucleotide. In certain embodiments, the compound comprises a conjugate moiety linked to the 3' terminus of a modified oligonucleotide. In certain embodiments, the compound comprises a conjugate moiety linked to the 5' terminus of a modified oligonucleotide. In certain embodiments, the compound comprises a first conjugate moiety linked to a 3' terminus of the modified oligonucleotide and a second conjugate moiety linked to the 5' terminus of a modified oligonucleotide.

In certain embodiments, a conjugate moiety comprises at least one ligand selected from a carbohydrate, cholesterol, a lipid, a phospholipid, an antibody, a lipoprotein, a hormone, a peptide, a vitamin, a steroid, or a cationic lipid.

Ligands may be covalently attached to a modified oligonucleotide by any suitable linker. Various linkers are known in the art, and certain nonlimiting exemplary linkers are described, e.g., in PCT Publication No. WO 2013/033230 and U.S. Pat. No. 8,106,022 B2. In some embodiments, a linker may be selected that is resistant to enzymatic cleavage in vivo. In some embodiments, a linker may be selected that is resistant to hydrolytic cleavage in vivo. In some embodiments, a linker may be selected that will undergo enzymatic cleavage in vivo. In some embodiments, a linker may be selected that will undergo hydrolytic cleavage in vivo.

In certain embodiments, a compound comprising a conjugated modified oligonucleotide described herein has the structure:

$$L\text{-}X_1\text{—}N_m\text{—}X_2\text{-MO};$$

wherein each L is a ligand; each N is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage. In certain embodiments, m is 1 and $X_1$ and $X_2$ are each phosphodiester.

In certain embodiments, a compound comprising a conjugated modified oligonucleotide described herein has Structure A:

$$L_n\text{-linker-MO};$$

wherein each L is, independently, a ligand and n is from 1 to 10; and MO is a modified oligonucleotide.

In certain embodiments, a compound comprising a conjugated modified oligonucleotide described herein has Structure B:

$$L_n\text{-linker-}X_1\text{—}N_m\text{—}X_2\text{-MO};$$

wherein each L is, independently, a ligand and n is from 1 to 10; each N is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprising a conjugated modified oligonucleotide described herein has Structure C:

$$L_n\text{-linker-}X\text{—}N_m\text{—}Y\text{-MO};$$

wherein each L is, independently, a ligand and n is from 1 to 10; each N is, independently, a modified or unmodified nucleoside and m is from 1 to 5; X is a phosphodiester linkage or a phosphorothioate linkage; Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprising a conjugated modified oligonucleotide described herein has Structure D:

$$L_n\text{-linker-}Y\text{—}N_m\text{—}Y\text{-MO};$$

wherein each L is, independently, a ligand and n is from 1 to 10; each N is, independently, a modified or unmodified nucleoside and m is from 1 to 5; each Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, when n is greater than 1, the linker comprises a scaffold capable of linking more than one L to the remainder of the compound (i.e., to the modified oligonucleotide (MO), to $X_1$—$N_m$—$X_2$-MO, to X—$N_m$—Y-MO, etc.). In some such embodiments, the $L_n$-linker portion of the compound (such as a compound of Structure A, B, C, or D) comprises Structure E:

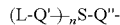

wherein each L is, independently, a ligand; n is from 1 to 10; S is a scaffold; and Q' and Q'' are, independently, linking groups.

In some embodiments, each Q' and Q'' is independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

In some embodiments, a scaffold is capable of linking 2, 3, 4, or 5 ligands to a modified oligonucleotide. In some embodiments, a scaffold is capable of linking 3 ligands to a modified oligonucleotide.

A nonlimiting exemplary Structure E is Structure E(i):

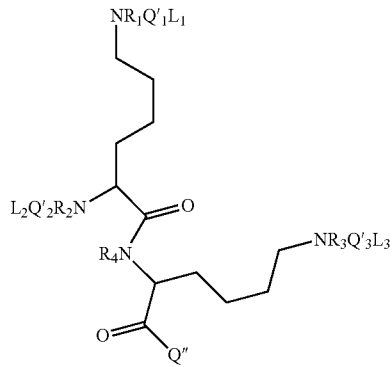

wherein $L_1$, $L_2$, and $L_3$ are each, independently, a ligand; $Q'_1$, $Q'_2$, $Q'_3$, and Q'' are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q'' are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments, $R_1$, $R_2$, $R_3$, and $R_4$ are each selected from H and methyl.

A further nonlimiting exemplary Structure E is Structure E(ii):

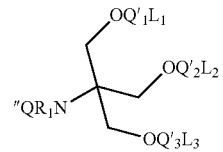

wherein $L_1$, $L_2$, and $L_3$ are each, independently, a ligand; $Q'_1$, $Q'_2$, $Q'_3$, and Q'' are each, independently, a linking group; and $R_1$ is selected from H, $C_1$-$C_6$ alkyl, and substituted $C_1$-$C_6$ alkyl.

In some embodiments, $Q'_1$, $Q'_2$, $Q'_3$, and Q'' are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$ is selected from H, methyl, ethyl, propyl, isopropyl, and butyl. In some embodiments, $R_1$ is H or methyl.

A further nonlimiting exemplary Structure E is Structure E(iii):

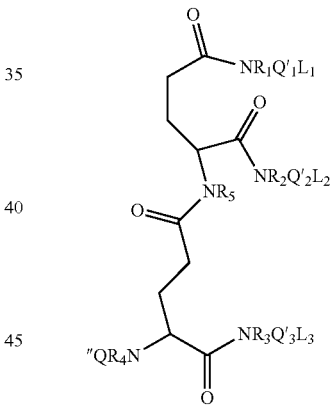

wherein $L_1$, $L_2$, and $L_3$ are each, independently, a ligand; $Q'_1$, $Q'_2$, $Q'_3$, and Q'' are each, independently, a linking group; and $R_1$, $R_2$, $R_3$, $R_4$, and $R_5$ are each, independently, selected from H, $C_1$-$C_6$ alkyl, and substituted $C_1$-$C_6$ alkyl.

In some embodiments, $Q'_1$, $Q'_2$, $Q'_3$, and Q'' are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, $R_4$, and $R_5$ are each, independently, selected from H, methyl, ethyl, propyl, isopropyl, and butyl. In some embodiments $R_1$, $R_2$, $R_3$, $R_4$, and $R_5$ are each selected from H and methyl.

A further nonlimiting exemplary Structure E is Structure E(iv):

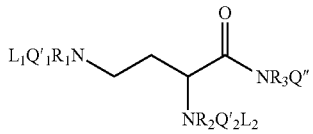

wherein $L_1$ and $L_2$ are each, independently, a ligand; $Q'_1$, $Q'_2$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(v):

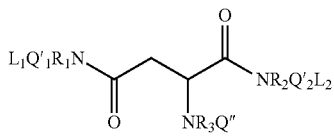

wherein $L_1$ and $L_2$ are each, independently, a ligand; $Q'_1$, $Q'_2$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vi):

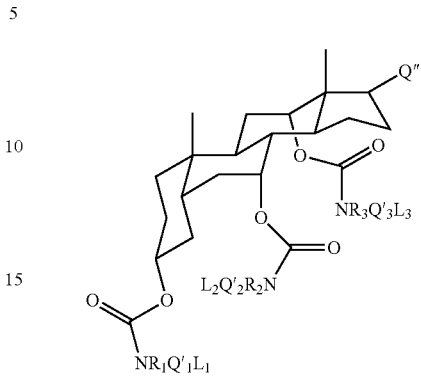

wherein $L_1$, $L_2$, and $L_3$ are each, independently, a ligand; $Q'_1$, $Q'_2$, $Q'_3$, and $Q''$ are each, independently, a linking group; and $R_1$, $R_2$, and $R_3$ are each, independently, selected from H, $C_1$-$C_6$ alkyl, and substituted $C_1$-$C_6$ alkyl.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl.

A further nonlimiting exemplary Structure E is Structure E(vii):

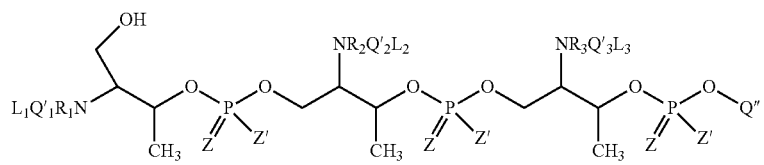

wherein $L_1$, $L_2$, and $L_3$ are each, independently, a ligand; $Q'_1$, $Q'_2$, $Q'_3$, and $Q''$ are each, independently, a linking group; $R_1$, $R_2$, and $R_3$ are each, independently, selected from H, $C_1$-$C_6$ alkyl, and substituted $C_1$-$C_6$ alkyl; and Z and Z' each independently selected from O and S.

In some embodiments, $Q'_1$, $Q'_2$, $Q'_3$, and $Q''$ are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, and $R_3$ are each, independently, selected from H, methyl, ethyl, propyl, isopropyl, and butyl. In some embodiments $R_1$, $R_2$, and $R_3$ are each selected from H and methyl. In some embodiments, Z or Z' on at least one P atom is S, and the other Z or Z' is O (i.e., a phosphorothioate linkage). In some embodiments, each —OP(Z)(Z')O— is a phosphorothioate linkage. In some embodiments, Z and Z' are both O on at least one P atom (i.e., a phosphodiester linkage). In some embodiments, each —OP(Z)(Z')O— is a phosphodiester linkage.

A further nonlimiting exemplary Structure E is Structure E(viii):

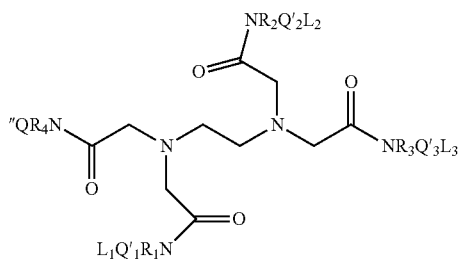

wherein $L_1$, $L_2$, and $L_3$ are each, independently, a ligand; $Q'_1$, $Q'_2$, $Q'_3$, and Q" are each, independently, a linking group; and $R_1$, $R_2$, $R_3$, and $R_4$ are each, independently, selected from H, $C_1$-$C_6$ alkyl, and substituted $C_1$-$C_6$ alkyl.

In some embodiments, $Q'_1$, $Q'_2$, $Q'_3$, and Q" are each, independently, selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid. In some embodiments, $R_1$, $R_2$, $R_3$, and $R_4$ are each, independently, selected from H, methyl, ethyl, propyl, isopropyl, and butyl. In some embodiments $R_1$, $R_2$, $R_3$, and $R_4$ are each selected from H and methyl.

Nonlimiting exemplary scaffolds and/or linkers comprising scaffolds, and synthesis thereof, are described, e.g., PCT Publication No. WO 2013/033230, U.S. Pat. No. 8,106,022 B2, U.S. Publication No. 2012/0157509 A1; U.S. Pat. No. 5,994,517; U.S. Pat. No. 7,491,805 B2; U.S. Pat. No. 8,313,772 B2; Manoharan, M., Chapter 16, Antisense Drug Technology, Crooke, S. T., Marcel Dekker, Inc., 2001, 391-469.

In some embodiments, the L-linker portion of the compound comprises Structure F:

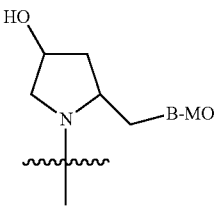

wherein:

B is selected from —O—, —S—, —N($R^N$)—, —Z—P(Z')(Z")O—, —Z—P(Z')(Z")O—$N_m$—X—, and —Z—P(Z')(Z")O—$N_m$—Y—;

MO is a modified oligonucleotide;

$R^N$ is selected from H, methyl, ethyl, propyl, isopropyl, butyl, and benzyl;

Z, Z', and Z" are each independently selected from O and S;

each N is, independently, a modified or unmodified nucleoside;

m is from 1 to 5;

X is selected from a phosphodiester linkage and a phosphorothioate linkage;

Y is a phosphodiester linkage; and the wavy line indicates the connection to the rest of the linker and ligand(s).

In certain embodiments, the wavy line indicates a connection to Structure E, above.

In certain embodiments, n is from 1 to 5, 1 to 4, 1 to 3, or 1 to 2. In certain embodiments, n is 1. In certain embodiments, n is 2. In certain embodiments, n is 3. In certain embodiments, n is 4. In certain embodiments, n is 5.

In some embodiments, the $L_n$-linker portion of the compound comprises Structure G:

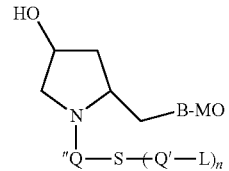

wherein:

B is selected from —O—, —S—, —N($R^N$)—, —Z—P(Z')(Z")O—, —Z—P(Z')(Z")O—$N_m$—X—, and —Z—P(Z')(Z")O—$N_m$—Y—;

MO is a modified oligonucleotide;

$R^N$ is selected from H, methyl, ethyl, propyl, isopropyl, butyl, and benzyl;

Z, Z', and Z" are each independently selected from O and S;

each N is, independently, a modified or unmodified nucleoside;

m is from 1 to 5;

X is selected from a phosphodiester linkage and a phosphorothioate linkage;

Y is a phosphodiester linkage;

each L is, independently, a ligand; n is from 1 to 10; S is a scaffold; and Q' and Q" are, independently, linking groups.

In some embodiments, each Q' and Q" are independently selected from a peptide, an ether, polyethylene glycol, an alkyl, a $C_1$-$C_{20}$ alkyl, a substituted $C_1$-$C_{20}$ alkyl, a $C_2$-$C_{20}$ alkenyl, a substituted $C_2$-$C_{20}$ alkenyl, a $C_2$-$C_{20}$ alkynyl, a substituted $C_2$-$C_{20}$ alkynyl, a $C_1$-$C_{20}$ alkoxy, a substituted $C_1$-$C_{20}$ alkoxy, amino, amido, a pyrrolidine, 8-amino-3,6-dioxaoctanoic acid (ADO), succinimidyl 4-(N-maleimidomethyl) cyclohexane-1-carboxylate, and 6-aminohexanoic acid.

A nonlimiting exemplary $L_n$-linker portion (e.g., of Structure F or G) of a compound is shown in Structure H below:

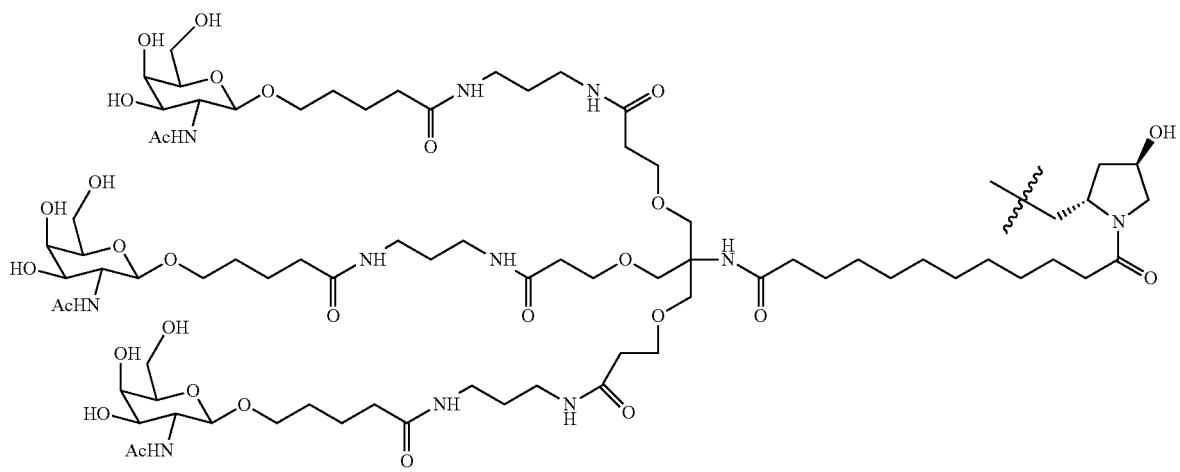 [SMILES: *C[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

wherein the wavy line indicates attachment to the modified oligonucleotide (MO), to $X_1$, e.g. in Structure B, or to X or Y, e.g., in Structure C, or D.

In certain embodiments, each ligand is a carbohydrate. A compound comprising a carbohydrate-conjugated modified oligonucleotide, when recognized by a cell surface lectin, is transported across the cell membrane into the cell. In certain embodiments, a cell surface lectin is a C-type lectin. In certain embodiments, the C-type lectin is present on a Kuppfer cell. In certain embodiments, a C-type lectin is present on a macrophage. In certain embodiments, a C-type lectin is present on an endothelial cell. In certain embodiments, a C-type lectin is present on a monocyte. In certain embodiments, a C-type lectin is present on a leukocyte. In certain embodiments, a C-type lectin is present on a dendritic cell. In certain embodiments, a C-type lectin is present on a B cell. A conjugate may facilitate uptake of an anti-miR-122 compound into any cell type that expresses a C-type lectin.

In certain embodiments, a C-type lectin is the asialoglycoprotein receptor (ASGPR). In certain embodiments, a conjugate comprises one or more ligands having affinity for the ASGPR, including but not limited to galactose or a galactose derivative. In certain embodiments, a ligand having affinity for the ASGPR is N-acetylgalactosamine, galactose, galactosamine, N-formylgalactosamine, N-propionyl-galactosamine, N-n-butanoylgalactosamine, or N-iso-butanoyl-galactosamine. Such conjugates facilitate the uptake of compounds into cells that express the ASGPR, for example, hepatocytes and dendritic cells.

In certain embodiments, a ligand is a carbohydrate selected from mannose, glucose, galactose, ribose, arabinose, fructose, fucose, xylose, D-mannose, L-mannose, D-galactose, L-galactose, D-glucose, L-glucose, D-ribose, L-ribose, D-arabinose, L-arabinose, D-fructose, L-fructose, D-fucose, L-fucose, D-xylose, L-xylose, alpha-D-manno-furanose, beta-D-mannofuranose, alpha-D-mannopyranose, beta-D-mannopyranose, alpha-D-glucofuranose, Beta-D-glucofuranose, alpha-D-glucopyranose, beta-D-glucopyranose, alpha-D-galactofuranose, beta-D-galactofuranose, alpha-D-galactopyranose, beta-D-galactopyranose, alpha-D-ribofuranose, beta-D-ribofuranose, alpha-D-ribopyranose, beta-D-ribopyranose, alpha-D-fructofuranose, alpha-D-fructopyranose, glucosamine, galactosamine, sialic acid, and N-acetylgalactosamine.

In certain embodiments, a ligand is selected from N-acetylgalactosamine, galactose, galactosamine, N-formylgalactosamine, N-propionyl-galactosamine, N-n-butanoylgalactosamine, and N-iso-butanoyl-galactosamine.

In certain embodiments, a ligand is N-acetylgalactosamine.

In certain embodiments, a compound comprises the structure:

(I)

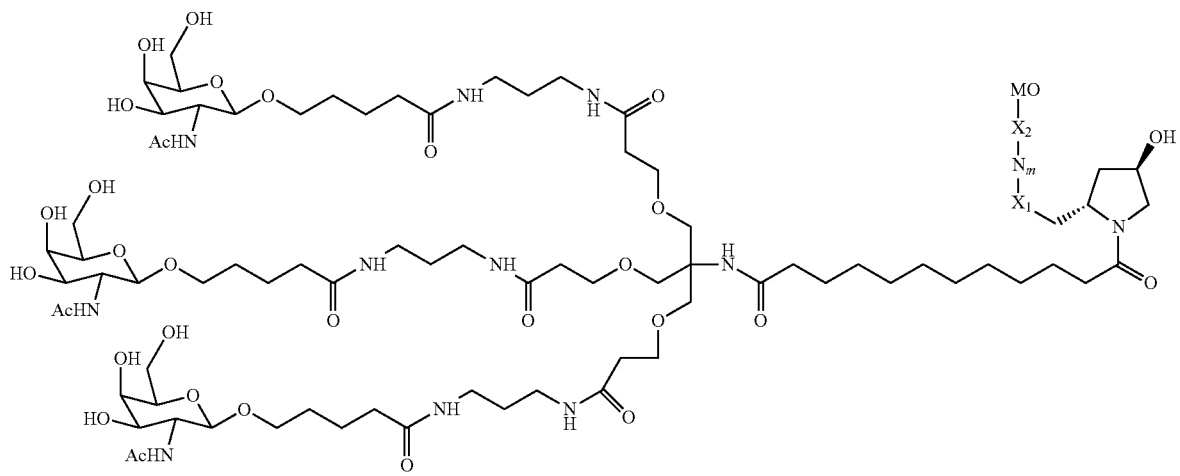

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprises the structure:

nucleoside and m is from 1 to 5; Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In certain embodiments, a compound comprises the structure:

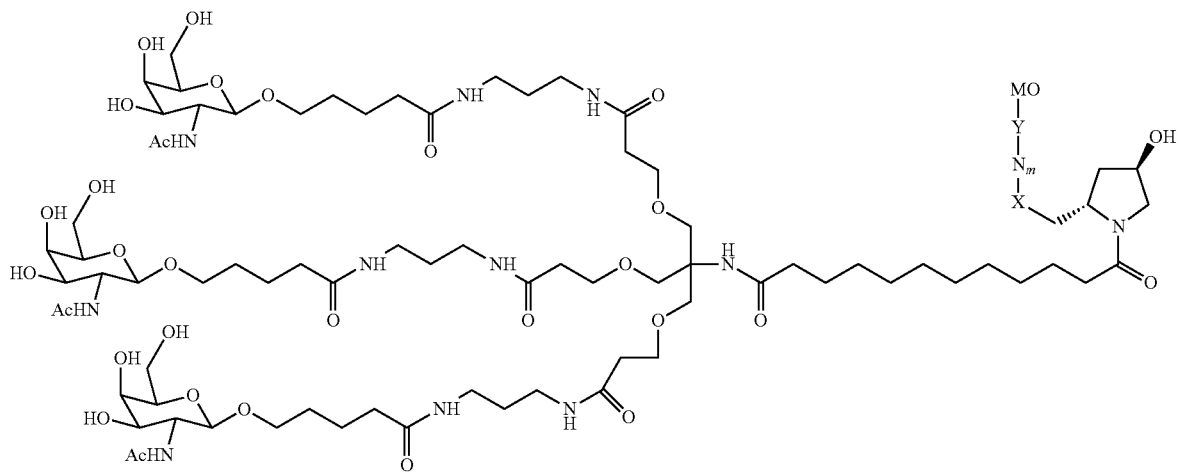

(II)

wherein X is a phosphodiester linkage or a phosphorothioate linkage; each N is, independently, a modified or unmodified

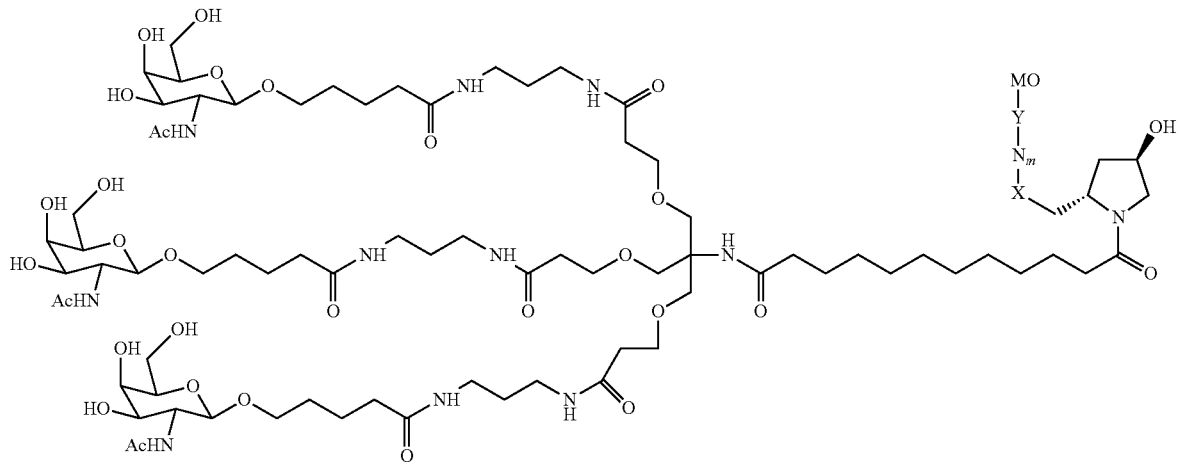

(II)

wherein X is a phosphodiester linkage; each N is, independently, a modified or unmodified nucleoside and m is from 1 to 5; Y is a phosphodiester linkage; and MO is a modified oligonucleotide. In certain embodiments, m is 1. In certain embodiments, m is 2. In certain embodiments, m is 3, 4, or 5. In certain embodiments, m is 2, 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or phosphorothioate internucleoside linkage.

In some embodiments, a compound has the structure:

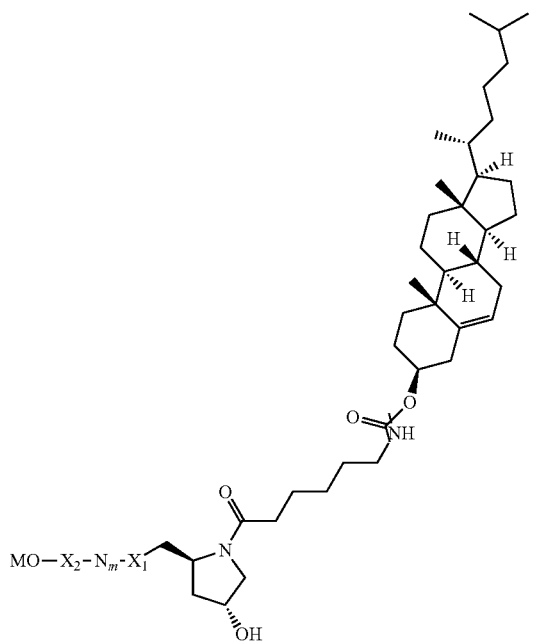

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide.

In certain embodiments, at least one of $X_1$ and $X_2$ is a phosphodiester linkage. In certain embodiments, each of $X_1$ and $X_2$ is a phosphodiester linkage.

In certain embodiments, m is 1. In certain embodiments, m is 2. In certain embodiments, m is 2, 3, 4, or 5. In certain embodiments, m is 3, 4, or 5. In certain embodiments, when m is greater than 1, each modified or unmodified nucleoside of $N_m$ may be connected to adjacent modified or unmodified nucleosides of $N_m$ by a phosphodiester internucleoside linkage or a phosphorothioate internucleoside linkage. In certain embodiments, when m is 2, the nucleosides of $N_m$ are linked by a phosphodiester internucleoside linkage.

In any of the embodiments described herein, $N_m$ may be $N'_pN''$, where each N' is, independently, a modified or unmodified nucleoside and p is from 0 to 4; and N'' is a nucleoside comprising an unmodified sugar moiety.

In certain embodiments, p is 0. In certain embodiments, p is 1, 2, 3, or 4. In certain embodiments, when p is 1, 2, 3, or 4, each N' comprises an unmodified sugar moiety.

In certain embodiments, an unmodified sugar moiety is a β-D-ribose or a β-D-deoxyribose.

In certain embodiments, where p is 1, 2, 3, or 4, N' comprises a purine nucleobase. In certain embodiments, N'' comprises a purine nucleobase. In certain embodiments, a purine nucleobase is selected from adenine, guanine, hypoxanthine, xanthine, and 7-methylguanine. In certain embodiments, N is a β-D-deoxyriboadenosine or a β-D-deoxyriboguanosine. In certain embodiments, N'' is a β-D-deoxyriboadenosine or a β-D-deoxyriboguanosine. In some embodiments, p is 1 and N' and N'' are each a β-D-deoxyriboadenosine.

In certain embodiments, where p is 1, 2, 3, or 4, N' comprises a pyrimidine nucleobase. In certain embodiments, N'' comprises a pyrimidine nucleobase. In certain embodiments, a pyrimidine nucleobase is selected from cytosine, 5-methylcytosine, thymine, uracil, and 5,6-dihydrouracil.

In any of the embodiments described herein, the sugar moiety of each N is independently selected from a β-D-ribose, a β-D-deoxyribose, a 2'-O-methoxy sugar, a 2'-O-methyl sugar, a 2'-fluoro sugar, and a bicyclic sugar moiety. In certain embodiments, each bicyclic sugar moiety is independently selected from a cEt sugar moiety, an LNA sugar moiety, and an ENA sugar moiety. In certain embodiments, the cEt sugar moiety is an S-cEt sugar moiety. In certain embodiments, the cEt sugar moiety is an R-cEt sugar moiety. In any embodiments described herein, the sugar moiety of each N may be independently selected from β-D-ribose, a β-D-deoxyribose, and a 2'-fluoro sugar.

In certain embodiments, a compound comprises the structure:

(II)

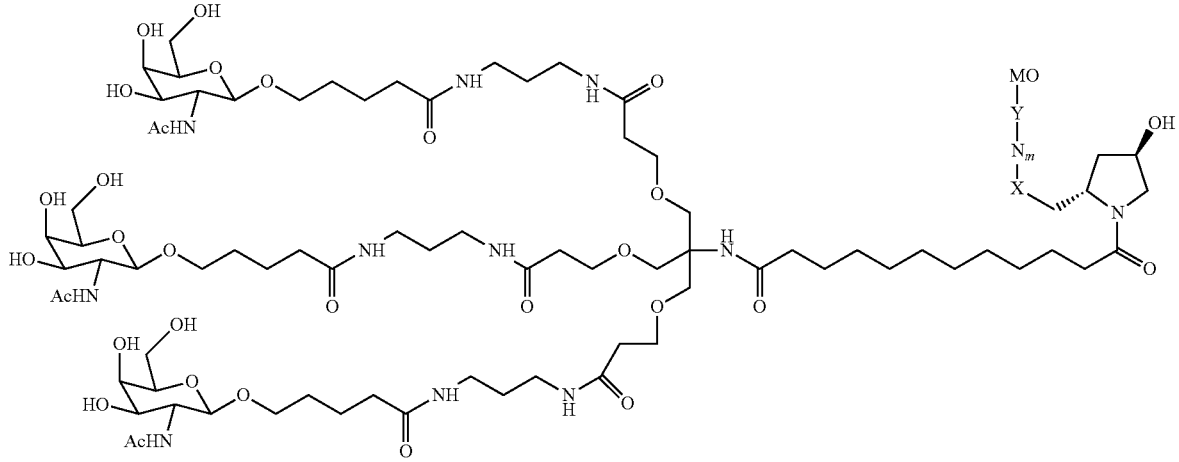

wherein X is a phosphodiester linkage; m is 1; N is a β-D-deoxyriboadenosine; Y is a phosphodiester linkage; and MO is a modified oligonucleotide.

In certain embodiments, a compound comprises the structure:

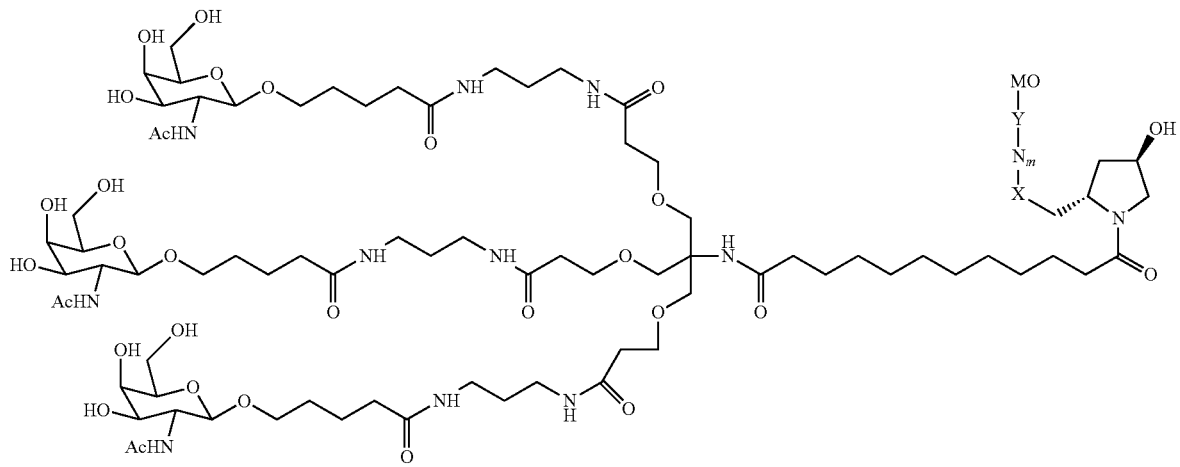

(II)

wherein X is a phosphodiester linkage; m is 2; each N is a β-D-deoxyriboadenosine; the nucleosides of N are linked by a phosphodiester internucleoside linkage; Y is a phosphodiester linkage; and MO is a modified oligonucleotide.

Additional moieties for conjugation to a modified oligonucleotide include phenazine, phenanthridine, anthraquinone, acridine, fluoresceins, rhodamines, coumarins, and dyes. In certain embodiments, a conjugate group is attached directly to a modified oligonucleotide.

In certain embodiments, the nucleobase sequence of a modified oligonucleotide is at least 80%, at least 85%, at least 90%, at least 91%, at least 92%, at least 95%, at least 96%, or 100% complementary to the nucleobase sequence of the target RNA. In certain embodiments, a modified oligonucleotide is at least 90%, at least 93%, at least 94%, at least 95%, or 100% complementary to a target RNA.

In certain embodiments, a modified oligonucleotide comprises at least one nucleoside with a modified sugar moiety. In certain embodiments, a modified oligonucleotide comprises a plurality of non-bicyclic nucleosides and a plurality of bicyclic nucleosides.

In certain embodiments, at least 70% of the nucleosides of a modified oligonucleotide comprise a modified sugar moiety. In certain embodiments, at least 80% of the nucleosides of a modified oligonucleotide comprise a modified sugar moiety. In certain embodiments, at least 90% of the nucleosides of a modified oligonucleotide comprise a modified sugar moiety. In certain embodiments, at least 95% of the nucleosides of a modified oligonucleotide comprise a modified sugar moiety.

In certain embodiments, at least two bicyclic nucleosides comprise sugar moieties that are different from one another. In certain embodiments, each bicyclic nucleoside has the same type of sugar moiety. In certain embodiments, at least two non-bicyclic nucleosides comprise sugar moieties that are different from one another. In certain embodiments, each non-bicyclic nucleoside has the same type of sugar moiety.

In certain embodiments, each non-bicyclic nucleoside is independently selected from a β-D-deoxyribonucleoside, a β-D-ribonucleoside, 2'-O-methyl nucleoside, a 2'-O-methoxyethyl nucleoside, and a 2'-fluoronucleoside. In certain embodiments, each non-bicyclic nucleoside is independently selected from a β-D-deoxyribonucleoside, and a 2'-O-methoxyethyl nucleoside. In certain embodiments, each non-bicyclic nucleoside is a β-D-deoxyribonucleoside.

In certain embodiments, the bicyclic nucleoside is selected from a cEt nucleoside, and LNA nucleoside, and an ENA nucleoside. In certain embodiments, the cEt nucleoside is an S-cEt nucleoside. In certain embodiments, the cEt nucleoside is an R-cEt nucleoside.

In certain embodiments, the modified oligonucleotide comprises a plurality of modified nucleosides and a plurality of β-D-deoxyribonucleoside, wherein each β-D-deoxyribonucleoside may comprise a modified or unmodified nucleobase. In certain embodiments, the modified oligonucleotide is a gapmer. In certain embodiments, the sugar moiety of each nucleoside is a modified sugar moiety. In certain embodiments, a modified nucleoside is a 2'-O-methoxyethyl nucleoside. In certain embodiments, a modified nucleoside is an S-cEt nucleoside.

In certain embodiments, a modified oligonucleotide consists of 7, 8, 9, 10, 11, 12, 13, 14, 15, 16, 17, 18, 19, 20, 21, 22, 23, 24, or 25 linked nucleosides. In certain embodiments, a modified oligonucleotide consists of 7 to 10 linked nucleosides. In certain embodiments, a modified oligonucleotide consists of 8 to 10 linked nucleosides. In certain embodiments, a modified oligonucleotide consists of 8 to 12 linked nucleosides. In certain embodiments, a modified oligonucleotide consists of 8 to 25 linked nucleosides. In certain embodiments, a modified oligonucleotide consists of 12 to 25 linked nucleosides. In certain embodiments, a modified oligonucleotide consists of 15 to 25 linked nucleosides. In certain embodiments, a modified oligonucleotide consists of 15 to 22 linked nucleosides. In certain embodiments, a modified oligonucleotide consists of 17 to 22 linked nucleosides. In certain embodiments, a modified oligonucleotide consists of 7 linked nucleosides. In certain embodiments, a modified oligonucleotide consists of 8 linked nucleosides. In certain embodiments, a modified oligonucleotide consists of 9 linked nucleosides. In certain embodiments, a modified oligonucleotide consists of 10 linked nucleosides. In certain embodiments, a modified oligonucleotide consists of 11 linked nucleosides. In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 8 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 8 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides.

In certain embodiments, at least one internucleoside linkage of a modified oligonucleotide is a modified internucleoside linkage. In certain embodiments, each internucleoside linkage of a modified oligonucleotide is a modified internucleoside linkage. In certain embodiments, the modified internucleoside linkage is a phosphorothioate internucleoside linkage. In certain embodiments, at least one nucleoside of a modified oligonucleotide comprises a modified nucleobase. In certain embodiments, at least one pyrimidine of the modified oligonucleotide comprises a 5-methyl group. In certain embodiments, at least one nucleoside of a modified oligonucleotide comprises a 5-methylcytosine. In certain embodiments, each cytosine of a modified oligonucleotide is a 5-methylcytosine.

In certain embodiments, where a modified oligonucleotide is between 7 and 12 linked nucleosides in length, each nucleoside of the modified oligonucleotide comprises a modified sugar moiety. In certain embodiments, where a modified oligonucleotide is between 7 and 10 linked nucleosides in length, each nucleoside of the modified oligonucleotide comprises a modified sugar moiety. In certain embodiments, where a modified oligonucleotide is between 8 and 12 linked nucleosides, each nucleoside of the modified oligonucleotide comprises a modified sugar moiety. In certain embodiments, a modified oligonucleotide consists of 7 linked nucleosides, wherein each nucleoside of the modified oligonucleotide comprises a modified sugar moiety. In certain embodiments, a modified oligonucleotide consists of 8 linked nucleosides, wherein each nucleoside of the modified oligonucleotide comprises a modified sugar moiety. In certain embodiments, a modified oligonucleotide consists of 9 linked nucleosides, wherein each nucleoside of the modified oligonucleotide comprises a modified sugar moiety. In certain embodiments, a modified oligonucleotide consists of 10 linked nucleosides, wherein each nucleoside of the modified oligonucleotide comprises a modified sugar moiety. In certain embodiments, a modified oligonucleotide consists of 11 linked nucleosides, wherein each nucleoside of the modified oligonucleotide comprises a modified sugar moiety. In certain embodiments, a modified oligonucleotide consists of 12 linked nucleosides, wherein each nucleoside of the modified oligonucleotide comprises a modified sugar moiety. In certain embodiments, each nucleoside of the modified oligonucleotide comprises a bicyclic sugar moiety. In certain embodiments, the bicyclic sugar moiety is a cEt sugar moiety. In certain embodiments, the cEt sugar moiety is an S-cEt sugar moiety. In certain embodiments, the bicyclic sugar moiety is an LNA sugar moiety.

In certain embodiments, a modified oligonucleotide is a gapmer.

Certain Metabolic Products

Upon exposure to exonucleases and/or endonucleases in vitro or in vivo, compounds may undergo cleavage at various positions throughout the compound. The products of such cleavage may retain some degree of the activity of the parent compound, and as such are considered active metabolites. As such, a metabolic product of a compound may be used in the methods described herein. In certain embodiments, a modified oligonucleotide (unconjugated or conjugated) undergoes cleavage at the 5' end and/or the 3' end, resulting in a metabolic product that has 1, 2, or 3 fewer nucleotides at the 5' end and/or the 3' end, relative to the parent modified oligonucleotide. In certain embodiments, a modified oligonucleotide undergoes cleavage at the 5' end, releasing the 5'-terminal nucleotide and resulting in a metabolic product that has 1 less nucleotide at the 5' end, relative to the parent modified oligonucleotide. In certain embodiments, a modified oligonucleotide undergoes cleavage at the 5' end, releasing two 5'-terminal nucleosides and resulting in a metabolic product that has two fewer nucleotides at the 5' end, relative to the parent modified oligonucleotide. In certain embodiments, a modified oligonucleotide undergoes cleavage at the 3' end, releasing the 3'-terminal nucleotide and resulting in a metabolic product that has one less nucleotide at the 3' end, relative to the parent modified oligonucleotide. In certain embodiments, a modified oligonucleotide undergoes cleavage at the 3' end, releasing two 3'-terminal nucleosides and resulting in a metabolic product that has two fewer nucleotides at the 3' end, relative to the parent modified oligonucleotide.

Compounds comprising modified oligonucleotide linked to a conjugate moiety may also undergo cleavage at a site within the linker between the modified oligonucleotide and the ligand. In certain embodiments, cleavage yields the parent modified oligonucleotide comprising a portion of the conjugate moiety. In certain embodiments, cleavage yields the parent modified oligonucleotide comprising one or more subunits of the linker between the modified oligonucleotide and the ligand. For example, where a compound has the structure $L_n$-linker-$N_m$—P-MO, in some embodiments, cleavage yields the parent modified oligonucleotide comprising one or more nucleotides of $N_m$. In some embodiments, cleavage of a conjugated modified oligonucleotide yields the parent modified oligonucleotide. In some such embodiments, for example, where a compound has the structure $L_n$-linker-$N_m$—P-MO, in some embodiments, cleavage yields the parent modified oligonucleotide without any of the nucleotides of $N_m$.

Certain Uses of Conjugated Modified Oligonucleotides

In certain embodiments, the target RNA is associated with a disease. Accordingly, administration of a conjugated modified oligonucleotide compound to a subject may treat, prevent, or delay the onset of a disease associated with the target RNA. In certain embodiments, the disease is associated with a target RNA expressed in a liver cell. In certain embodiments, the disease is associated with a target RNA expressed in a hepatocyte. In certain embodiments, the disease is associated with a target RNA expressed in a macrophage. In certain embodiments, the disease is associated with a target RNA expressed in a dendritic cell. In certain embodiments, the target RNA is a microRNA.

Provided herein are conjugated compounds, for use in therapy.

Certain Target RNAs

Any of the compounds provided herein may comprise a modified oligonucleotide that has a nucleobase sequence complementary to a target RNA. In any of the embodiments described herein, a target RNA may be any nucleic acid capable of being targeted including, without limitation, microRNAs, pri-microRNAs, pre-microRNAs, pre-messenger RNAs, messenger RNAs, long noncoding RNAs, small transfer RNAs, small nuclear RNAs, small nucleolar RNAs, small ribosomal RNAs, small hairpin RNAs, endogenous antisense RNAs, guide RNAs, tiny noncoding RNAs, small single or double stranded RNAs that are encoded by heterochromatic repeats at centromeres or other chromosomal origin, and any precursors thereof. Target RNAs may be coding or non-coding sequences; single- or double-stranded, or single-stranded with partial double-stranded character; may occur naturally within introns or exons of messenger RNAs (mRNAs), ribosomal RNAs (rRNAs), or transfer RNAs (tRNAs); and can be endogenously transcribed or exogenously produced.

Upon hybridization of a modified oligonucleotide to its target RNA, the function of the target RNA may be inhibited through a nondegradative mechanism, for example RNA antagonism, modulation of RNA splicing, modulation of polyadenylation, disruption of RNA secondary structure, and inhibition of translation, or through a mechanism that promotes degradation of the target RNA, for example RNase H, RNA interference, ribozymes, and double-stranded RNases.

Certain MicroRNA Targets

Any of the compounds provided herein may comprise a modified oligonucleotide having a nucleobase sequence complementary to a microRNA.

Nucleobase sequences of certain mature microRNA and their corresponding stem-loop sequence are found in miRBase, an online searchable database of microRNA sequences and annotation, found at microrna.sanger.ac.uk. Entries in the miRBase Sequence database represent a predicted hairpin portion of a microRNA transcript (the stem-loop), with information on the location and sequence of the mature microRNA sequence. The microRNA stem-loop sequences in the database are not strictly precursor microRNAs (pre-microRNAs), and may in some instances include the pre-microRNA and some flanking sequence from the presumed primary transcript. The sequences of the microRNA targets encompass any version of the microRNA, including the sequences described in Release 15.0 of the miRBase sequence database and sequences described in any earlier Release of the miRBase sequence database. A sequence database release may result in the re-naming of certain microRNAs. The compositions of the present invention encompass modified oligonucleotides that are complementary to any nucleobase sequence version of the microRNA targets.

In certain embodiments, each nucleobase of a modified oligonucleotide targeted to a microRNA is capable of undergoing base-pairing with a nucleobase at each corresponding position in the nucleobase sequence of the microRNA, or a precursor thereof. In certain embodiments the nucleobase sequence of a modified oligonucleotide may have one or more mismatched basepairs with respect to its target microRNA or precursor sequence, and remains capable of hybridizing to its target sequence.

In certain embodiments, a modified oligonucleotide has a nucleobase sequence that is complementary to the nucleobase sequence of a microRNA precursor, such as a microRNA stem-loop sequence. As a mature microRNA is contained within a microRNA precursor sequence, a modified oligonucleotide having a nucleobase sequence complementary to a microRNA is also complementary to a region of a the corresponding microRNA precursor.

In certain embodiments, a modified oligonucleotide consists of a number of linked nucleosides that is equal to the length of the microRNA sequence to which it is complementary.

In certain embodiments, the number of linked nucleosides of a modified oligonucleotide is less than the length of a microRNA, or a precursor thereof. In certain embodiments, the oligonucleotide has a nucleobase sequence that is complementary to a region of the microRNA, or the precursor thereof. A modified oligonucleotide having a number of linked nucleosides that is less than the length of the microRNA, wherein each nucleobase of a modified oligonucleotide is complementary to each nucleobase at a corresponding position in a microRNA nucleobase sequence, is considered to be a modified oligonucleotide having a nucleobase sequence that is fully complementary to a region of a microRNA nucleobase sequence. For example, a modified oligonucleotide consisting of 22 linked nucleosides, where the nucleobases of nucleosides 1 through 22 are each complementary to a corresponding position of a microRNA that is 23 nucleobases in length, is fully complementary to a 22 nucleobase region of the nucleobase sequence of the microRNA. Such a modified oligonucleotide has a nucleobase sequence that is 100% complementarity to a 22 nucleobase portion of the microRNA. Further, such a modified oligonucleotide is considered to be 100% complementary to the microRNA.

In certain embodiments, the number of linked nucleosides of a modified oligonucleotide is one less than the length of the microRNA. In certain embodiments, a modified oligonucleotide has one less nucleoside at the 5' terminus. In certain embodiments, a modified oligonucleotide has one less nucleoside at the 3' terminus. In certain embodiments, a modified oligonucleotide has two fewer nucleosides at the 5' terminus. In certain embodiments, a modified oligonucleotide has two fewer nucleosides at the 3' terminus.

In certain embodiments, a region of the nucleobase sequence of a modified oligonucleotide is fully complementary to a region of the nucleobase sequence of a microRNA. In certain embodiments, 8 contiguous nucleobases of a modified oligonucleotide are each complementary to 8 contiguous nucleobases of a microRNA. In certain embodiments, 9 contiguous nucleobases of a modified oligonucleotide are each complementary to 9 contiguous nucleobases of a microRNA. In certain embodiments, 10 contiguous nucleobases of a modified oligonucleotide are each complementary to 10 contiguous nucleobases of a microRNA. In certain embodiments, 11 contiguous nucleobases of a modified oligonucleotide are each complementary to 11 contiguous nucleobases of a microRNA. In certain embodiments, 12 contiguous nucleobases of a modified oligonucleotide are each complementary to 12 contiguous nucleobases of a microRNA. In certain embodiments, 13 contiguous nucleobases of a modified oligonucleotide are each complementary to 13 contiguous nucleobases of a microRNA. In certain embodiments, 14 contiguous nucleobases of a modified oligonucleotide are each complementary to 14 contiguous nucleobases of a microRNA. In certain embodiments, 15 contiguous nucleobases of a modified oligonucleotide are each complementary to 15 contiguous nucleobases of a microRNA. In certain embodiments, 16 contiguous nucleobases of a modified oligonucleotide are each complementary to 16 contiguous nucleobases of a microRNA. In certain embodiments, 17 contiguous nucleobases of a modified oligonucleotide are each complementary to 17 contiguous nucleobases of a microRNA. In certain embodiments, 18 contiguous nucleobases of a modified oligonucleotide are each complementary to 18 contiguous nucleobases of a microRNA. In certain embodiments, 19 contiguous nucleobases of a modified oligonucleotide are each complementary to 19 contiguous nucleobases of a microRNA. In certain embodiments, 20 contiguous nucleobases of a modified oligonucleotide are each complementary to 20 contiguous nucleobases of a microRNA. In certain embodiments, 22 contiguous nucleobases of a modified oligonucleotide are each complementary to 22 contiguous nucleobases of a microRNA. In certain embodiments, 23 contiguous nucleobases of a modified oligonucleotide are each complementary to 23 contiguous nucleobases of a microRNA. In certain embodiments, 24 contiguous nucleobases of a modified oligonucleotide are each complementary to 24 contiguous nucleobases of a microRNA. In certain embodiments, 25 contiguous nucleobases of a modified oligonucleotide are each complementary to 25 contiguous nucleobases of a microRNA.

In certain embodiments, a modified oligonucleotide comprises a nucleobase sequence that is complementary to a seed sequence, i.e. a modified oligonucleotide comprises a seed-match sequence. In certain embodiments, a seed sequence is a hexamer seed sequence. In certain embodiments, a hexamer seed sequence is nucleobases 1-6 of a microRNA. In certain embodiments, a hexamer seed sequence is nucleobases 2-7 of a microRNA. In certain embodiments, a hexamer seed sequence is nucleobases 3-8 of a microRNA. In certain embodiments, a seed sequence is a heptamer seed sequence. In certain embodiments, a heptamer seed sequence is nucleobases 1-7 of a microRNA. In certain embodiments, a heptamer seed sequence is nucleobases 2-8 of a microRNA. In certain embodiments, the seed sequence is an octamer seed sequence. In certain embodiments, an octamer seed sequence is nucleobases 1-8 of a microRNA. In certain embodiments, an octamer seed sequence is nucleobases 2-9 of a microRNA.

In certain embodiments, a nucleobase sequence of a modified oligonucleotide is 100% complementary to a microRNA nucleobase sequence listed herein, or a precursor thereof. In certain embodiments, a modified oligonucleotide has a nucleobase sequence having one mismatch with respect to the nucleobase sequence of a microRNA, or a precursor thereof. In certain embodiments, a modified oligonucleotide has a nucleobase sequence having two mismatches with respect to the nucleobase sequence of a microRNA, or a precursor thereof. In certain embodiments, a modified oligonucleotide has a nucleobase sequence having no more than two mismatches with respect to the nucleobase sequence of a microRNA, or a precursor thereof. In certain embodiments, the mismatched nucleobases are contiguous. In certain embodiments, the mismatched nucleobases are not contiguous.

In certain embodiments, the number of linked nucleosides of a modified oligonucleotide is greater than the length of a microRNA sequence. In certain embodiments, the nucleobase of an additional nucleoside is complementary to a nucleobase of a microRNA stem-loop sequence. In certain embodiments, the number of linked nucleosides of a modified oligonucleotide is one greater than the length of a microRNA. In certain embodiments, the additional nucleoside is at the 5' terminus of a modified oligonucleotide. In certain embodiments, the additional nucleoside is at the 3' terminus of a modified oligonucleotide. In certain embodiments, the number of linked nucleosides of a modified oligonucleotide is two greater than the length of a microRNA. In certain embodiments, the two additional nucleosides are at the 5' terminus of a modified oligonucleotide. In certain embodiments, the two additional nucleosides are at the 3' terminus of a modified oligonucleotide. In certain embodiments, one additional nucleoside is located at the 5' terminus and one additional nucleoside is located at the 3' terminus of a modified oligonucleotide. In certain embodiments, a region of the modified oligonucleotide may be fully complementary to the nucleobase sequence of a microRNA, but the entire modified oligonucleotide is not fully complementary to a microRNA. For example, a modified oligonucleotide consisting of 23 linked nucleosides, where the nucleobases of nucleosides 1 through 22 are each complementary to a corresponding position of a microRNA that is 22 nucleobases in length, has a 22 nucleoside portion that is 100% complementary to the nucleobase sequence of a microRNA.

Certain Nucleobase Sequences

Any nucleobase sequences set forth herein, including but not limited to those found in the Examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in practice, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$CGAUCG," wherein $^{me}$C indicates a cytosine base comprising a methyl group at the 5-position.

Certain Synthesis Methods

Modified oligonucleotides may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite trimester with an oxidizing or sulfurizing agent), and capping (acetylation of unreacted 5'-hydroxyl groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exchange resin.

GalNAc-conjugated modified oligonucleotides may be made with automated solid phase synthesis, similar to the solid phase synthesis that produced unconjugated oligonucleotides. During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example in U.S. Pat. No. 8,106,022, which is herein incorporated by reference in its entirety for the description of the synthesis of carbohydrate-containing conjugates, including conjugates comprising one or more GalNAc moieties, and of the synthesis of conjugate covalently linked to solid support.

Provided herein are processes of making a GalNAc-conjugated modified oligonucleotide having the structure shown in formula (IV):

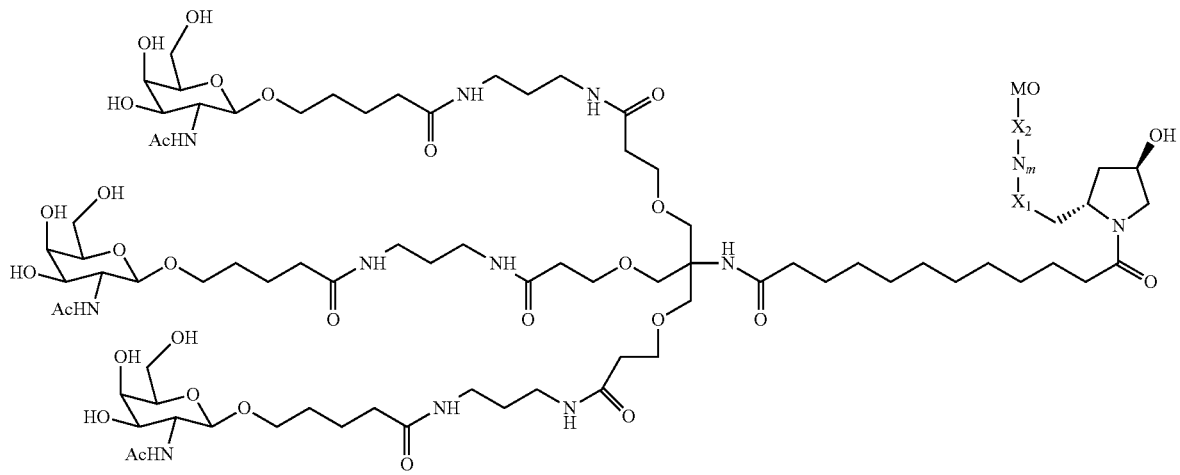

(I)

wherein each N is, independently, a modified or unmodified nucleoside and m is from 1 to 5; $X_1$ and $X_2$ are each, independently, a phosphodiester linkage or a phosphorothioate linkage; and MO is a modified oligonucleotide; comprising the steps of:

providing a solid support comprising a conjugate as shown in formula IV;

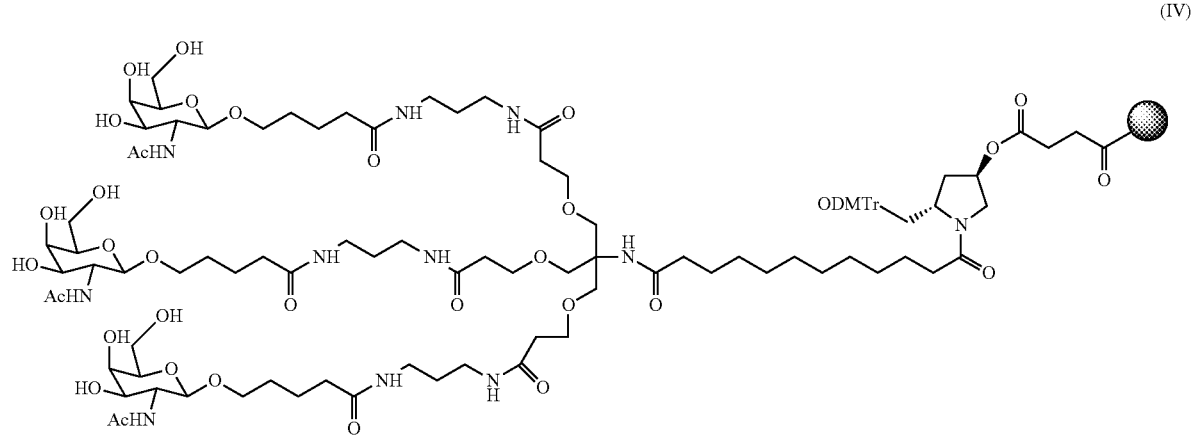

(IV)

deprotecting the DMT group under conditions effective to produce a reactive hydroxyl;

performing sequential phosphoramidite coupling steps to form $N_m$;

performing sequential phosphoramidite coupling steps to form MO;

and releasing the conjugated modified oligonucleotide from the solid support.

Certain Modified Oligonucleotides

In certain embodiments, a modified oligonucleotide consists of 8 to 30 linked nucleosides. In certain embodiments, a modified oligonucleotide consists of 15 to 30 linked nucleosides. In certain embodiments, a modified oligonucleotide consists of 12 to 25 linked nucleosides. In certain embodiments, a modified oligonucleotide consists of 15 to 21 linked nucleosides. In certain embodiments, a modified oligonucleotide consists of 15 to 19 linked nucleosides. In certain embodiments, a modified oligonucleotide consists of 15 to 16 linked nucleosides. In certain embodiments, a modified oligonucleotide consists of 19 to 24 linked nucleosides. In certain embodiments, a modified oligonucleotide consists of 21 to 24 linked nucleosides.

In certain embodiments, a modified oligonucleotide consists of 8 linked nucleosides. In certain embodiments, a modified oligonucleotide consists of 9 linked nucleosides. In certain embodiments, a modified oligonucleotide consists of 10 linked nucleosides. In certain embodiments, a modified oligonucleotide consists of 11 linked nucleosides. In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

In certain embodiments, a modified oligonucleotide is a fully modified oligonucleotide. In certain embodiments, fully modified oligonucleotides comprise a sugar modification at each nucleoside. In certain embodiments, fully modified oligonucleotides comprise at least one modified internucleoside linkage. In certain embodiments, fully modified oligonucleotides comprise a sugar modification at each nucleoside, and each internucleoside linkage is a modified internucleoside linkage. In certain embodiments, fully modified oligonucleotide comprise a sugar modification at each nucleoside, and comprise at least one phosphorothioate internucleoside linkage. In certain embodiments, a fully modified oligonucleotide comprises a sugar modification at each nucleoside, and each internucleoside linkage is a phosphorothioate internucleoside linkage. In certain embodiments, each nucleoside of a fully modified oligonucleotide comprises the same modified sugar moiety.

In certain embodiments, a modified oligonucleotide is a uniformly modified oligonucleotide. In certain embodiments, each nucleoside of a uniformly modified oligonucleotide comprises the same sugar modified moiety. In certain embodiments, each internucleoside linkage of a uniformly modified oligonucleotide comprises the same modified internucleotide linkage.

In certain embodiments, a modified oligonucleotide has a gapmer motif. In certain embodiments, each nucleoside of each external comprises the same modified sugar moiety. In certain embodiments, at least two nucleosides of one external region comprise modified sugar moieties that are different from one another. In certain embodiments, at least two nucleosides of each external region comprise modified sugar moieties that are different from one another. In certain embodiments, each nucleoside of each external region comprises a 2'-O-methoxyethyl sugar. In certain embodiments, each nucleoside of each external region comprises a bicyclic sugar moiety. In certain embodiments, the bicyclic sugar moiety is a cEt sugar moiety. In certain embodiments, the cEt sugar moiety is an S-cEt sugar moiety. In certain embodiments, the bicyclic sugar moiety is an LNA sugar moiety.

In certain embodiments, each external region of a gapmer consists of the same number of linked nucleosides. In certain embodiments, one external region of a gapmer consists a number of linked nucleosides different that that of the other external region.

In certain embodiments, each external region comprises, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiments, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

In certain embodiments, each external region comprises 5 linked nucleosides, and the internal region comprises 10 linked nucleosides. In certain embodiments, each external region comprises 4 linked nucleosides, and the internal region comprises 10 linked nucleosides. In certain embodiments, each external region comprises 3 linked nucleosides, and the internal region comprises 10 linked nucleosides. In certain embodiments, each external region comprises 2 linked nucleosides, and the internal region comprises 10 linked nucleosides.

In certain embodiments, a modified oligonucleotide is a single-stranded siRNA. In certain embodiments, a modified oligonucleotide is a double-stranded siRNA. In certain embodiments, a modified oligonucleotide is a single-stranded microRNA mimic. In certain embodiments, a modified oligonucleotide is a double-stranded microRNA mimic.

Certain Modifications

Provided herein are compounds comprising modified oligonucleotides attached to a conjugate moiety. A modified oligonucleotid may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain embodiments, a modified nucleoside is a stabilizing nucleoside. An example of a stabilizing nucleoside is a sugar-modified nucleoside.

In certain embodiments, a modified nucleoside comprises a modified sugar moiety. In certain embodiments, a modified nucleoside comprising a modified sugar moiety comprises an unmodified nucleobase. In certain embodiments, a modified sugar comprises a modified nucleobase. In certain embodiments, a modified nucleoside is a 2'-modified nucleoside.

In certain embodiments, a 2'-modified nucleoside comprises a bicyclic sugar moiety. In certain embodiments, the bicyclic sugar moiety is a D sugar in the alpha configuration. In certain embodiments, the bicyclic sugar moiety is a D sugar in the beta configuration. In certain embodiments, the bicyclic sugar moiety is an L sugar in the alpha configuration. In certain embodiments, the bicyclic sugar moiety is an L sugar in the beta configuration.

In certain embodiments, the bicyclic sugar moiety comprises a bridge group between the 2' and the 4'-carbon atoms. In certain embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. Examples of such 4' to 2' sugar substituents, include, but are not limited to: —[C($R_a$)($R_b$)]$_n$—, —[C($R_a$)($R_b$)]$_n$—O—, —C($R_aR_b$)—N(R)—O— or, —C($R_aR_b$)—O—N(R)—; 4'-CH$_2$-2', 4'-(CH$_2$)$_2$-2', 4'-(CH$_2$)$_3$-2'; 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or $C_1$-$C_{12}$ alkyl; 4'-CH$_2$—N(R)—O-2', wherein R is H, $C_1$-$C_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise 1 or from 2 to 4 linked groups independently selected from —[C($R_a$)($R_b$)]$_n$—, —C($R_a$)=C(R)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. In certain embodiments, bicyclic nucleosides include, but are not limited to, (A) α-L-Methyleneoxy (4'-CH$_2$—O-2') BNA; (B) β-D-Methyleneoxy (4'-CH$_2$—O-2') BNA; (C) Ethyleneoxy (4'-(CH$_2$)$_2$—O-2') BNA; (D) Aminooxy (4'-CH$_2$—O—N(R)-2') BNA; (E) Oxyamino (4'-CH$_2$—N(R)—O-2') BNA; (F) Methyl(methyleneoxy) (4'-CH(CH$_3$)—O-2') BNA (also referred to as constrained ethyl or cEt); (G) methylene-thio (4'-CH$_2$—S-2') BNA; (H) methylene-amino (4'-CH$_2$—N(R)-2') BNA; (I) methyl carbocyclic (4'-CH$_2$—CH(CH$_3$)-2') BNA; (J) c-MOE (4'-CH$_2$—OMe-2') BNA and (K) propylene carbocyclic (4'-(CH$_2$)$_3$-2') BNA as depicted below.

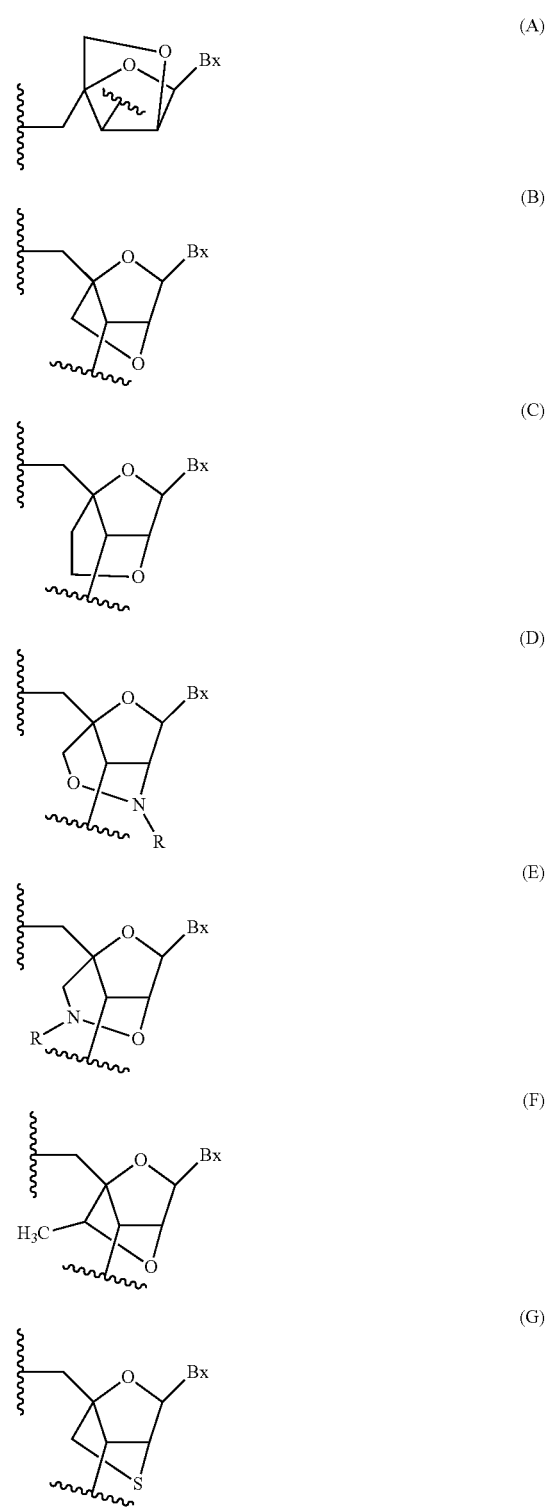

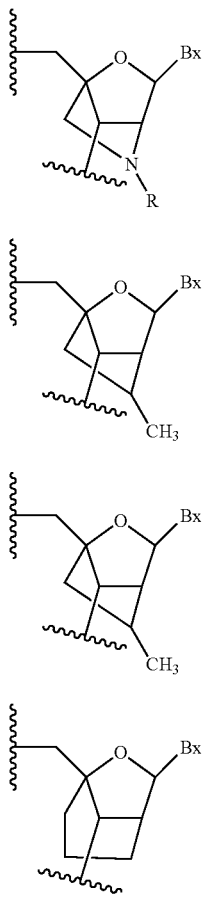

wherein Bx is a nucleobase moiety and R is, independently, H, a protecting group, or $C_1$-$C_{12}$ alkyl.

In certain embodiments, a 2'-modified nucleoside comprises a 2'-substituent group selected from halo, allyl, amino, azido, SH, CN, OCN, $CF_3$, $OCF_3$, O—, S—, or $N(R_m)$-alkyl; O—, S—, or $N(R_m)$-alkenyl; O—, S— or $N(R_m)$-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N $(R_m)(R_n)$ or O—$CH_2$—C(=O)—$N(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, —$O(CH_2)_2O(CH_2)_2N(CH_3)_2$, and N-substituted acetamide (O—$CH_2$—C(=O)—$N(R_m)$ $(R_n)$ where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'-$O(CH_2)_2SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a nucleoside comprising a modified sugar moiety is a 4'-thio modified nucleoside. In certain embodiments, a nucleoside comprising a modified sugar moiety is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—$(CH_2)_2$—$OCH_3$, and 2'-F.

In certain embodiments, a modified oligonucleotide comprises one or more internucleoside modifications. In certain embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain embodiments, an internucleoside linkage is formed by a short chain alkyl internucleoside linkage. In certain embodiments, an internucleoside linkage is formed by a cycloalkyl internucleoside linkages. In certain embodiments, an internucleoside linkage is formed by a mixed heteroatom and alkyl internucleoside linkage. In certain embodiments, an internucleoside linkage is formed by a mixed heteroatom and cycloalkyl internucleoside linkages. In certain embodiments, an internucleoside linkage is formed by one or more short chain heteroatomic internucleoside linkages. In certain embodiments, an internucleoside linkage is formed by one or more heterocyclic internucleoside linkages. In certain embodiments, an internucleoside linkage has an amide backbone. In certain embodiments, an internucleoside linkage has mixed N, O, S and $CH_2$ component parts.

In certain embodiments, a modified oligonucleotide comprises one or more modified nucleobases.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and 0-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

In certain embodiments, a modified oligonucleotide comprises one or more stabilizing groups that are attached to one or both termini of an oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Pharmaceutical Compositions

Any of the compounds provided herein may be prepared as a pharmaceutical composition.

In certain embodiments, a pharmaceutical composition is administered in the form of a dosage unit (e.g., tablet, capsule, bolus, etc.). In some embodiments, a pharmaceutical composition comprises a compound provided herein at a dose within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. In certain embodiments, such pharmaceutical compositions comprise a compound provided herein present at a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose compound provided herein selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical composition comprising a compound provided herein is administered at a dose of 10 mg/kg or less, 9 mg/kg or less, 8 mg/kg or less, 7.5 mg/kg or less, 7 mg/kg or less, 6.5 mg/kg or less, 6 mg/kg or less, 5.5 mg/kg or less, 5 mg/kg or less, 4.5 mg/kg or less, 4 mg/kg or less, 3.5 mg/kg or less, 3 mg/kg or less, 2.5 mg/kg or less, 2 mg/kg or less, 1.5 mg/kg or less, 1 mg/kg or less, 0.75 mg/kg or less, 0.5 mg/kg or less, or 0.25 mg/kg or less.

In certain embodiments, a pharmaceutical agent is sterile lyophilized compound that is reconstituted with a suitable diluent, e.g., sterile water for injection or sterile saline for injection. The reconstituted product is administered as a subcutaneous injection or as an intravenous infusion after dilution into saline. The lyophilized drug product consists of a compound which has been prepared in water for injection, or in saline for injection, adjusted to pH 7.0-9.0 with acid or base during preparation, and then lyophilized. The lyophilized compound may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. Further, in some embodiments, the lyophilized compound is present in an amount that ranges from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, or 400 mg to 600 mg. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, a pharmaceutical composition provided herein comprises a compound in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprises a polyamine compound or a lipid moiety complexed with a nucleic acid. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more compounds and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more compounds provided herein to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition provided herein is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, one or more modified oligonucleotides provided herein is administered as a prodrug. In certain embodiments, upon in vivo administration, a prodrug is chemically or enzymatically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain embodiments, prodrugs possess superior transmittal across cell membranes. In certain embodiments, a prodrug facilitates delivery of a modified oligonucleotide to the desired cell type, tissue, or organ. In certain embodiments, a prodrug is a compound comprising a conjugated modified oligonucleotide. In certain instances, a prodrug may have improved solubility compared to the corresponding active form. In certain embodiments, prodrugs are less water soluble than the corresponding active form. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug, and/or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). In certain embodiments, a prodrug is a compound comprising a modified oligonucleotide is linked to a conjugated moiety in such a way as to allow for cleavage of the conjugate moiety and regeneration of the modified oligonucleotide upon in vivo administration. A compound comprising a modified oligonucleotide linked to a cleavable conjugate moiety, such as, for example, a compound of structure B, C, D, (I), or (II) described herein, may release the modified oligonucleotide in its unconjugated form, upon in vivo administration.

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administering to a subject comprises intraarterial, pulmonary, oral, rectal, transmucosal, intestinal, enteral, topical, transdermal, suppository, intrathecal, intraventricular, intraperitoneal, intranasal, intraocular, intramuscular, intramedullary, and intratumoral administration.

Certain Additional Therapies

Treatments for a disease associated with a target RNA may comprise more than one therapy. As such, in certain embodiments provided herein are methods for treating a subject having or suspected of having a disease associated with a target RNA comprising administering at least one therapy in addition to administering a GalNAc-conjugated modified oligonucleotide.

In certain embodiments, the at least one additional therapy comprises a pharmaceutical agent.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid is prednisone. In certain embodiments, an anti-inflammatory agent is a non-steroidal anti-inflammatory drugs. In certain embodiments, a non-steroidal anti-inflammatory agent is ibuprofen, a COX-I inhibitors, or a COX-2 inhibitors.

In certain embodiments, pharmaceutical agents include, but are not limited to, diuretics (e.g. sprionolactone, eplerenone, furosemide), inotropes (e.g. dobutamine, milrinone), digoxin, vasodilators, angiotensin II converting enzyme (ACE) inhibitors (e.g. are captopril, enalapril, lisinopril, benazepril, quinapril, fosinopril, and ramipril), angiotensin II receptor blockers (ARB) (e.g. candesartan, irbesartan, olmesartan, losartan, valsartan, telmisartan, eprosartan), calcium channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide).

In certain embodiments, pharmaceutical agents include heparinoids. In certain embodiments, a heparinoid is pentosan polysulfate.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and *echinacea*), and vaccines, e.g., the immunostimulating complex (ISCOM), which comprises a vaccine formulation that combines a multimeric presentation of antigen and an adjuvant.

In certain embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Further examples of additional pharmaceutical agents include, but are not limited to, immunoglobulins, including, but not limited to intravenous immunoglobulin (IVIg); analgesics (e.g., acetaminophen); salicylates; antibiotics; antivirals; antifungal agents; adrenergic modifiers; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Kits

Any compound provided herein can be present in a kit. The kit can also contain instructions for using a compound provided herein. In some embodiments, a compound provided herein can be present within a vial. A plurality of vials, such as 10, can be present in, for example, dispensing packs. In some embodiments, the vial is manufactured so as to be accessible with a syringe.

In some embodiments, the kits may be used for administration a compound provided herein to a subject. In such instances, in addition to a compound provided herein, the kit can further comprise one or more of the following: syringe, alcohol swab, cotton ball, and/or gauze pad. In some embodiments, the compounds can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds.

Certain Quantitation Assays

The effects of a modified oligonucleotide on the activity of its target RNA may be assessed by a variety of methods known in the art. In certain embodiments, these methods are be used to quantitate microRNA levels in cells or tissues in vitro or in vivo.

In certain embodiments, changes in target levels and/or activity are measured by microarray analysis. In certain embodiments, changes in target levels and/or activity are measured by one of several commercially available PCR assays, such as the TaqMan® MicroRNA Assay (Applied Biosystems).

In vitro activity of anti-miR compounds may be assessed using a luciferase cell culture assay. In this assay, a microRNA luciferase sensor construct is engineered to contain one or more binding sites of the microRNA of interest, and a luciferase gene. When the microRNA binds to its cognate site in the luciferase sensor construct, luciferase expression is suppressed. When the appropriate anti-miR is introduced into the cells, it binds to the target microRNA and relieves suppression of luciferase expression. Thus, in this assay anti-miRs that are effective inhibitors of the anti-miR of interest will cause an increase in luciferase expression.

Activity of anti-miR compounds may be assessed by measuring the mRNA and/or protein level of a target of a microRNA. A microRNA binds to its cognate site within one or more target RNAs, leading to suppression of a target RNA, thus inhibition of the microRNA results in the increase in the level of mRNA and/or protein of a target of the microRNA (i.e., derepression). The derepression of one or more target RNAs may be measured in vivo or in vitro.

EXAMPLES

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

Example 1

Conjugated Modified Oligonucleotides

GalNAc-containing compounds were formed by conjugating the structure in FIG. 2 to the 3' end of the modified oligonucleotides shown in Table A. Sugar moieties, internucleoside linkages, and nucleobases are indicated as follows: the superscript "Me" indicates 5-methylcytosine; nucleosides not followed by a subscript are β-D-deoxyribonucleosides; nucleosides followed by a subscript "E" are 2'-MOE nucleosides; nucleosides followed by a subscript "S" are S-cEt nucleosides; nucleosides followed by a subscript "L" are LNA nucleosides; and each internucleoside linkage is a phosphorothioate internucleoside linkage.

TABLE A

Unconjugated and Conjugated Modified Oligonucleotides

Figure 2A:
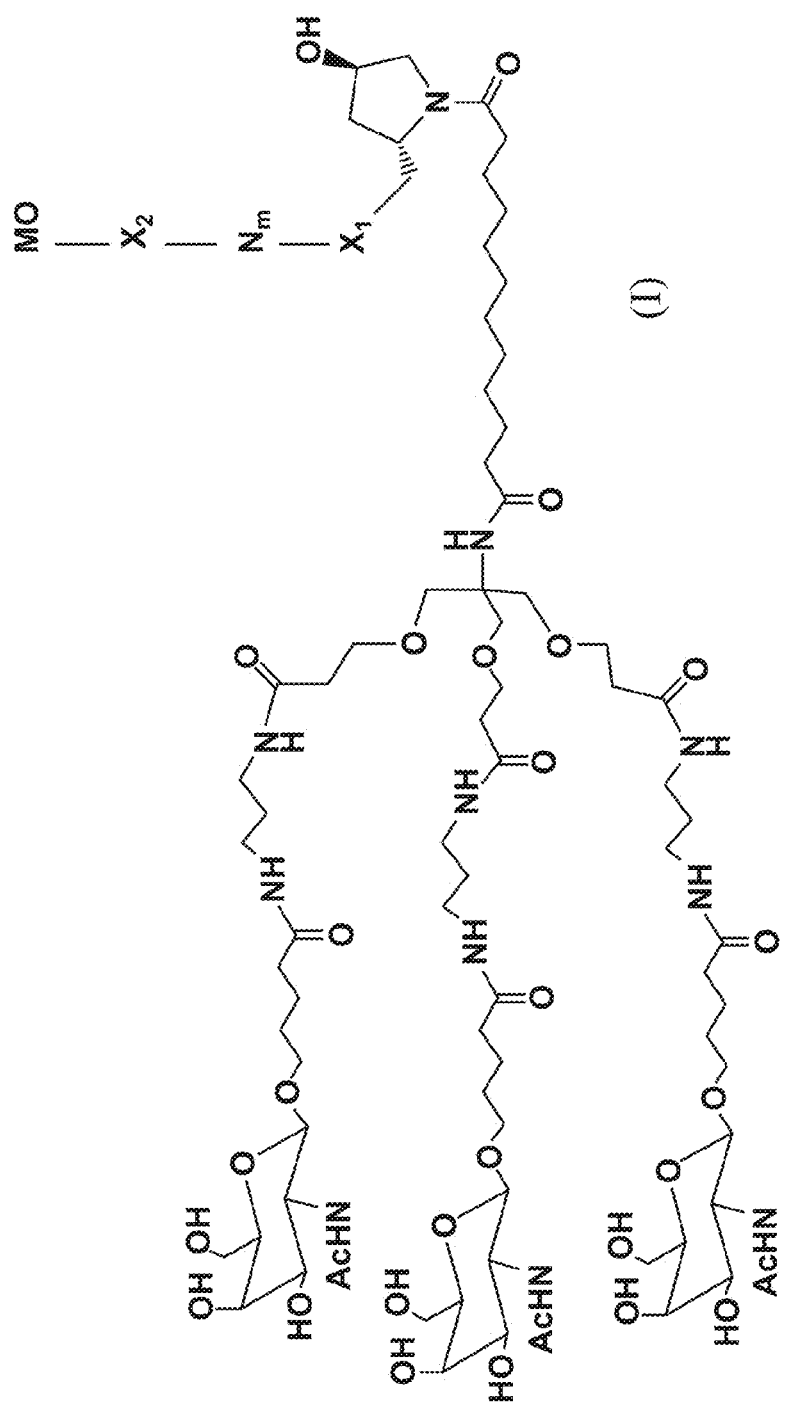
FIGS. 2A, 2B, and 2C. Conjugated modified oligonucleotide structures.
Figure 2B:
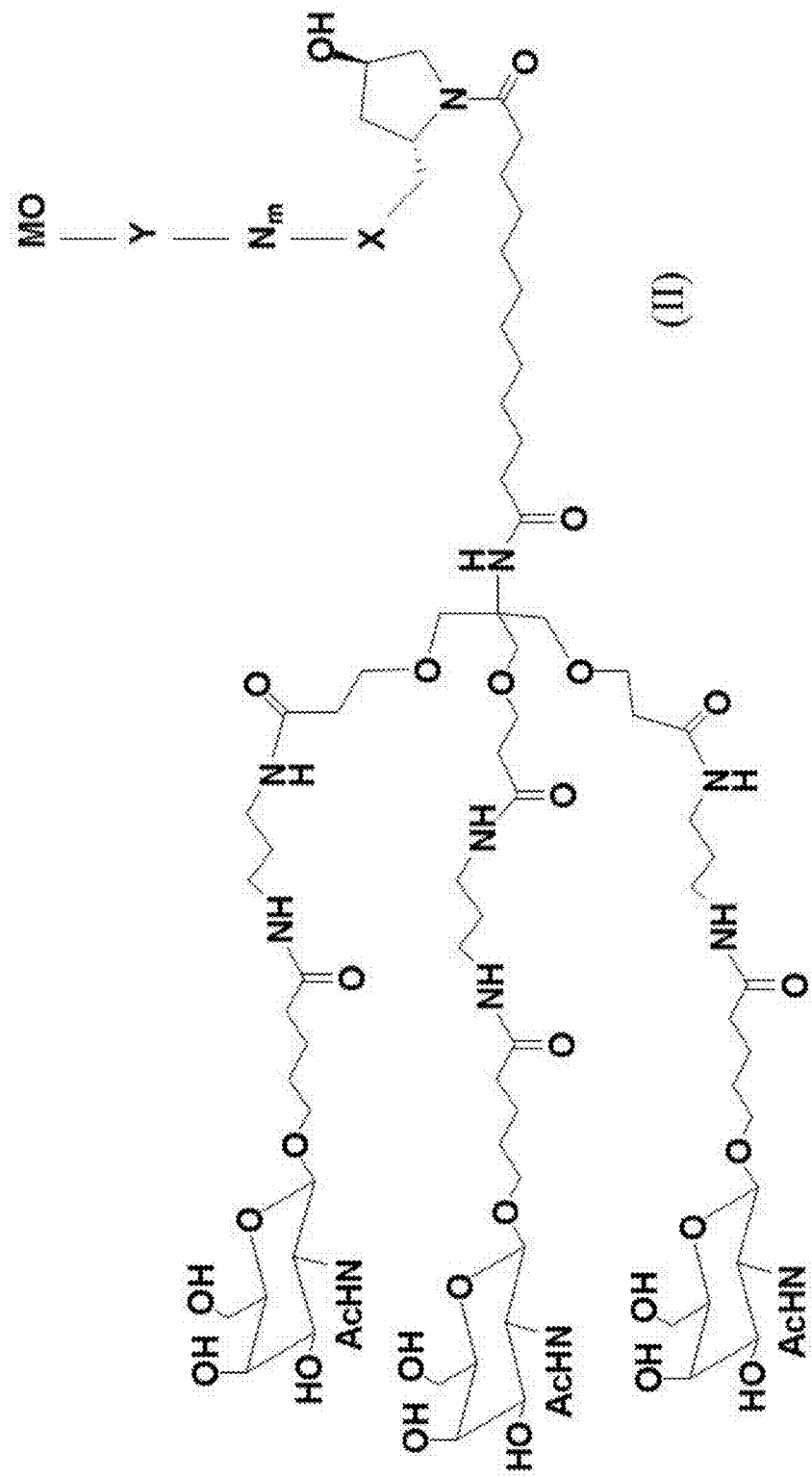
Figure 2C:
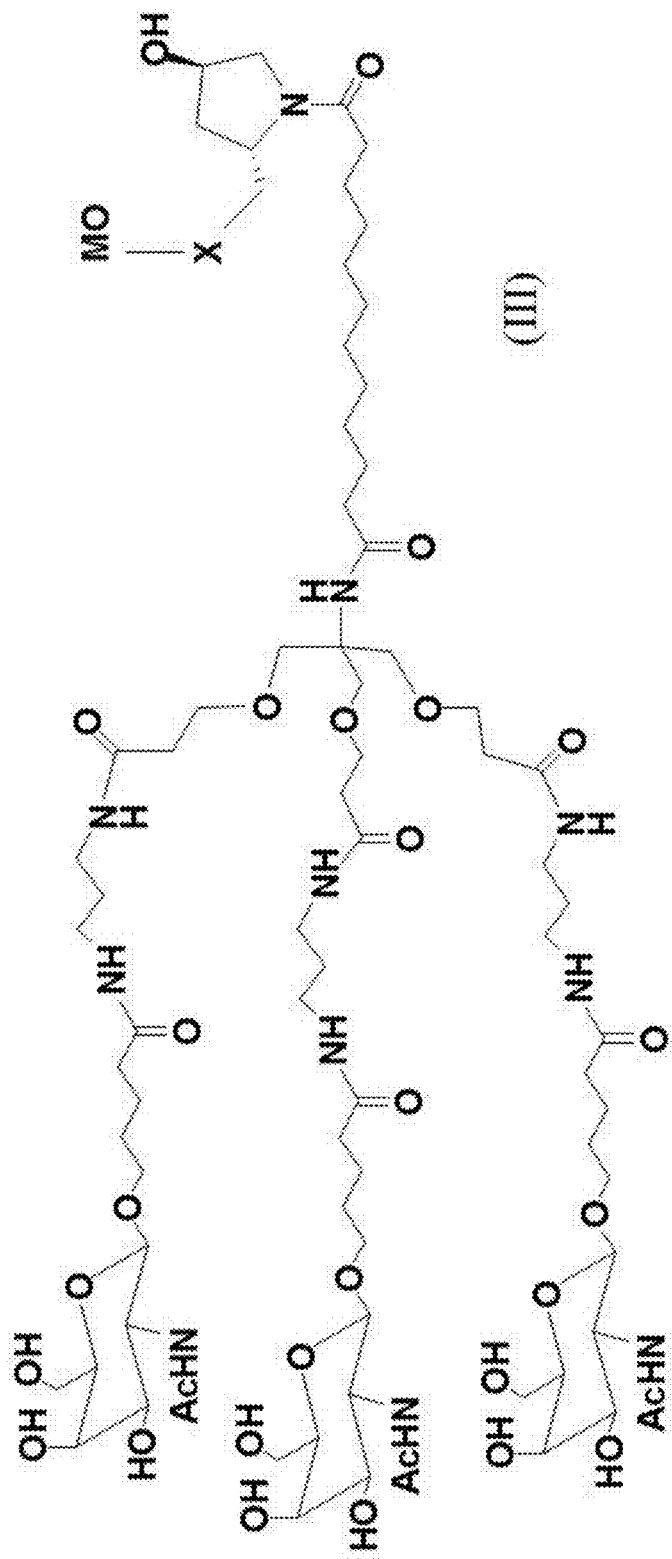

| | Sequence and Modifications | Structure | SEQ ID |
|---|---|---|---|
| 38577 | $A_E{}^{Me}C_E A^{Me}C_L CA_L TTG_L T_L CA^{Me}C_L A^{Me}C_L T^{Me}C_L{}^{Me}C_L A_S$ | Unconjugated | 2 |
| 38128 | $A_E{}^{Me}C_E AC_S C_S ATU_S GTC_S AC_S AC_S TC_S C_S A_E$ | Unconjugated | 3 |
| 38853 | $A_E{}^{Me}C_E A^{Me}C_L CA_L TTG_L T_L CA^{Me}C_L A^{Me}C_L T^{Me}C_L{}^{Me}C_L A_S$ | Structure III of FIG. 2C, where X is PO and MO is 38577 | 2 |
| 38856 | $A_E{}^{Me}C_E AC_S C_S ATU_S GTC_S AC_S AC_S TC_S C_S A_E$ | Structure III of FIG. 2C, where X is PO and MO is 38128 | 3 |

The GalNAc-conjugated modified oligonucleotides were assessed for in vivo potency, release of full-length unconjugated modified oligonucleotide, and liver and tissue concentration.

To determine in vivo potency, the compounds were evaluated for their ability to de-repress the expression of liver aldolase A (ALDOA), a gene that is normally suppressed by miR-122 activity. Inhibition of miR-122 leads to an increase in ALDOA expression, thus ALDOA mRNA levels can be used to measure miR-122 inhibitory activity in vivo. Compounds were administered to mice, and ALDOA mRNA levels were measured, by quantitative PCR, in RNA isolated from liver. The fold change in ALDOA mRNA, relative to saline, was calculated to determine in vivo potency.

Figure 3:
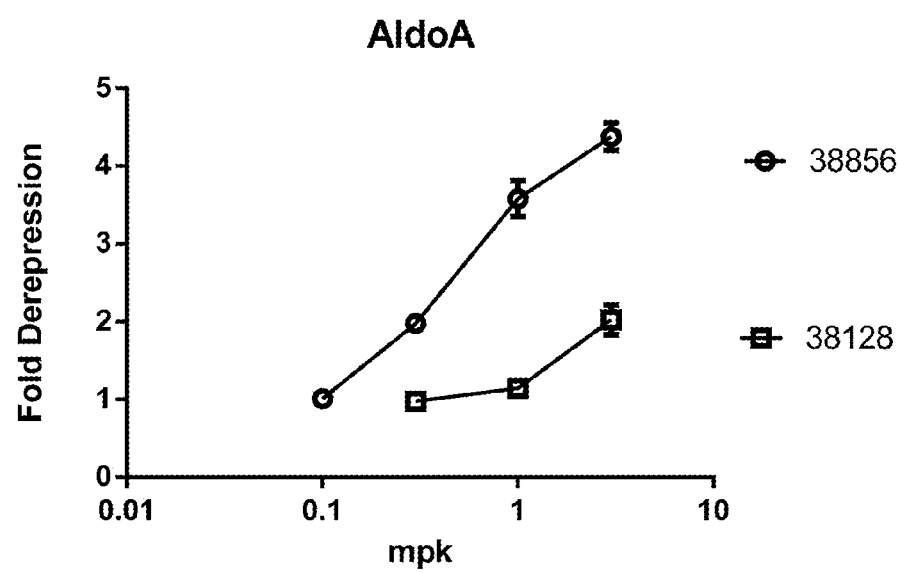
FIGS. 3A and 3B. In vivo potency of GalNAc-conjugated anti-miR-122 modified oligonucleotides.
Figure 3:
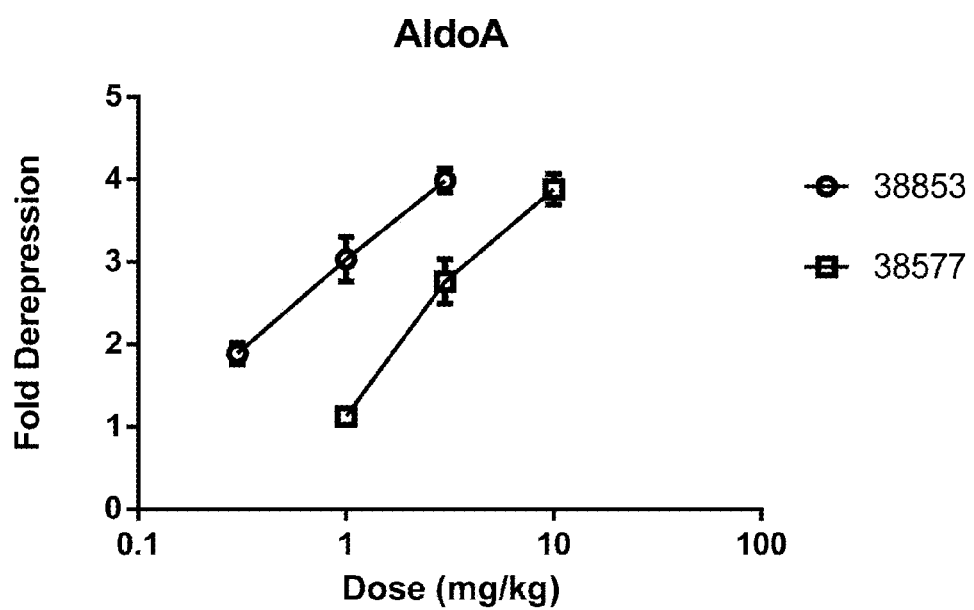

As shown in FIGS. 3A and 3B, each of the GalNAc-conjugated modified oligonucleotides shown in Table A was more potent than the corresponding unconjugated modified oligonucleotide. Compounds 38856 and 38853 exhibited an increase in potency of approximately 10-fold, relative to unconjugated compounds 38128 and 38577.

Also tested were LNA-containing unconjugated and conjugated modified oligonucleotides, shown in Table B.

122, the GalNAc-conjugated compound 38852 exhibited greater potency than unconjugated compound 38848.

Figure 4:
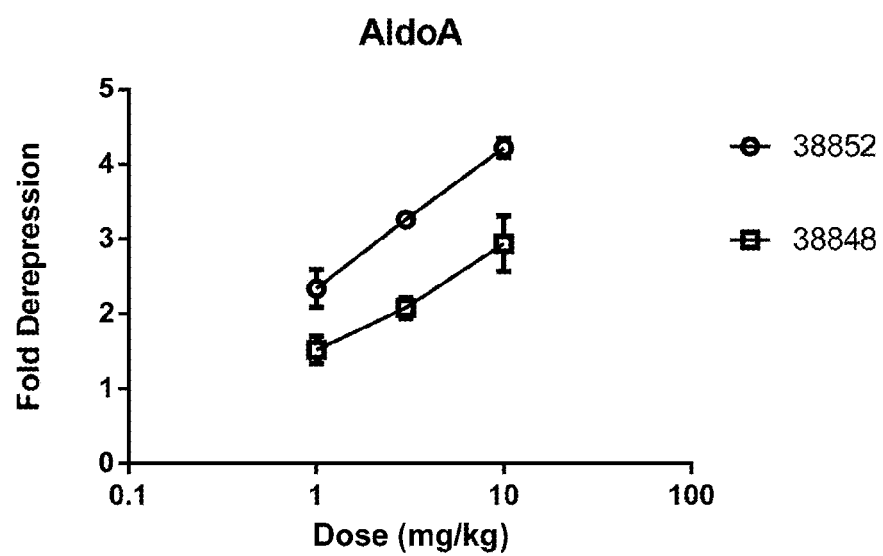
FIGS. 4A and 4B. In vivo potency of GalNAc-conjugated anti-miR-122 modified oligonucleotides.
Figure 4:
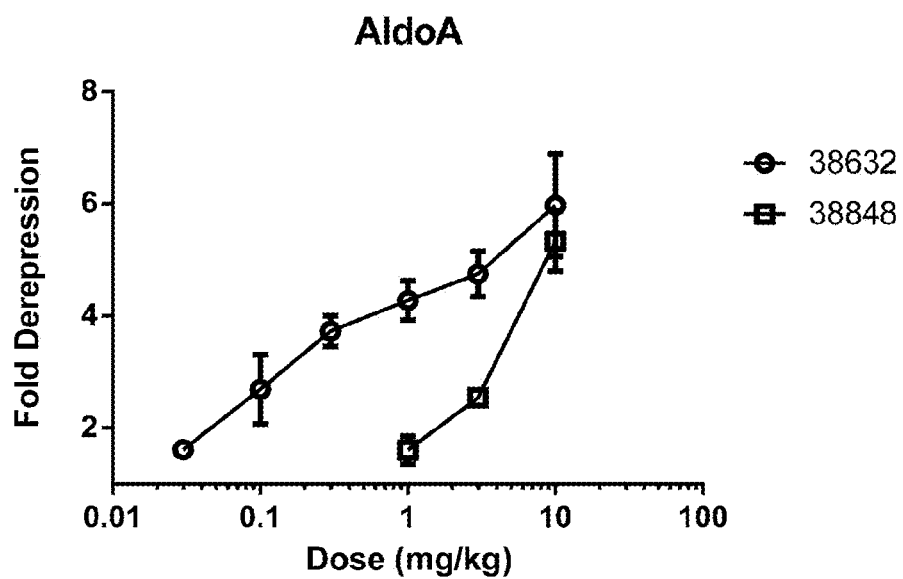

Compound 38632 was tested for in vivo potency according to the same protocol as described above, to evaluate the ability of the compound to inhibit miR-122 activity and increase ALDOA expression. As shown in FIG. 4B, while each compound was a potent inhibitor of miR-122, the GalNAc-conjugated compound 38632 exhibited greater potency than both unconjugated compound 38848 and conjugated compound 38852. In this experiment, the ED50 of 38848 was 4.24 mg/kg, and the ED50 of 38632 was 0.31 mg/kg, demonstrating an improvement in potency of at least 20-fold.

Additional GalNAc-containing compounds were made by conjugating the structure in FIG. 2 to the 3' end of the 38649 modified oligonucleotide. Modified oligonucleotide 38649 has the structure $A_E{}^{Me}C_E A_E{}^{Me}C_E{}^{Me}C_E A_E T_E TGU_S C_S AC_S AC_S TC_S C_S$ (SEQ ID NO: 5), where the superscript "Me" indicates 5-methylcytosine; nucleosides not followed by a subscript are β-D-deoxyribonucleosides; nucleosides followed by a subscript "E" are 2'-MOE nucleosides; nucleo-

TABLE B

LNA-containing compounds

| Compound # | Sequence (5' to 3') and Modifications | Structure | SEQ ID |
|---|---|---|---|
| 38848 | $C_L CA_L TTG_L T_L CAC_L AC_L TC_L C_L$, | Unconjugated | 4 |
| 38852 | $C_L CA_L TTG_L T_L CAC_L AC_L TC_L C_L$ | Conjugated as in Structure III of FIG. 2C, where X is PO and MO is 38848 | 4 |
| 38632 | $C_L CA_L TTG_L T_L CAC_L AC_L TC_L C_L$ | Conjugated as in Structure I of FIG. 2A, where $X_2$ is a phophodiester linkage, m is 1, $N_m$ is a β-D-deoxynucleoside (dA), $X_1$ is a phosphodiester linkage, and MO is compound 38848 | 4 |

Sugar and linkage moieties are indicated as follows: where nucleosides not followed by a subscript indicate β-D-deoxyribonucleosides; nucleosides followed by a subscript "L" indicate LNA nucleosides; and each internucleoside linkage is a phosphorothioate internucleoside linkage.

Compounds 38848 and 38852 were tested for in vivo potency according to the same protocol as described above, to evaluate the ability of the compounds to inhibit miR-122 activity and increase ALDOA expression. As shown in FIG. 4A, while each compound was a potent inhibitor of miRsides followed by a subscript "S" are S-cEt nucleosides; and each internucleoside linkage is a phosphorothioate internucleoside linkage.

The linkage between the GalNAc-containing moiety and the 3'-end of 38649 varied, as shown in Table C. For example, in compound 38368, the GalNAc-containing moiety is linked directly to the 3'-terminal nucleoside of 38649 through a phosphodiester linkage, as shown in FIG. 2C, where X is a phosphodiester linkage and MO is 38649. In compound 38458, the GalNAc-containing moiety is linked to the 3'-terminal nucleoside of 38649 through a β-D-deoxynucleoside, with a phosphorothioate linkage between the 3'-terminal nucleoside of 38649 and a phosphodiester linkage between the β-D-deoxynucleoside and the GalNAc-containing moiety, as shown in FIG. 2A, where $X_2$ is a phosphorothioate linkage, m is 1, $N_m$ is a β-D-deoxynucleoside, $X_1$ is a phosphodiester linkage, and MO is 38649.

TABLE C

GalNAc-containing compounds

| Compound # | Compound structure |
|---|---|
| 38368 | Structure III of FIG. 2C, where X is a phosphodiester linkage and MO is compound 38649 |
| 38371 | Structure III of FIG. 2C, where X is a phosphorothioate linkage and MO is compound 38649 |
| 38458 | Structure I of FIG. 2A, where $X_2$ is a phophorothioate linkage, m is 1, $N_m$ is a β-D-deoxynucleoside (dA), $X_1$ is a phosphodiester linkage, and MO is compound 38649 |
| 38459 | Structure I of FIG. 2A, where $X_2$ is a phophodiester linkage, m is 1, $N_m$ is a β-D-deoxynucleoside (dA), $X_1$ is a phosphodiester linkage, and MO is compound 38649 |
| 38597 | Structure I of FIG. 2A, where $X_2$ is a phosphorothioate linkage, m is 1, $N_m$ is a 2'-O-methoxyethyl nucleoside, $X_1$ is a phosphodiester linkage, and MO is compound 38649 |
| 38598 | Structure I of FIG. 2A, where $X_2$ is a phophorothioate linkage, m is 1, $N_m$ is a $X_1$ is a phosphodiester linkage, and MO is compound 38649 |

Figure 5:
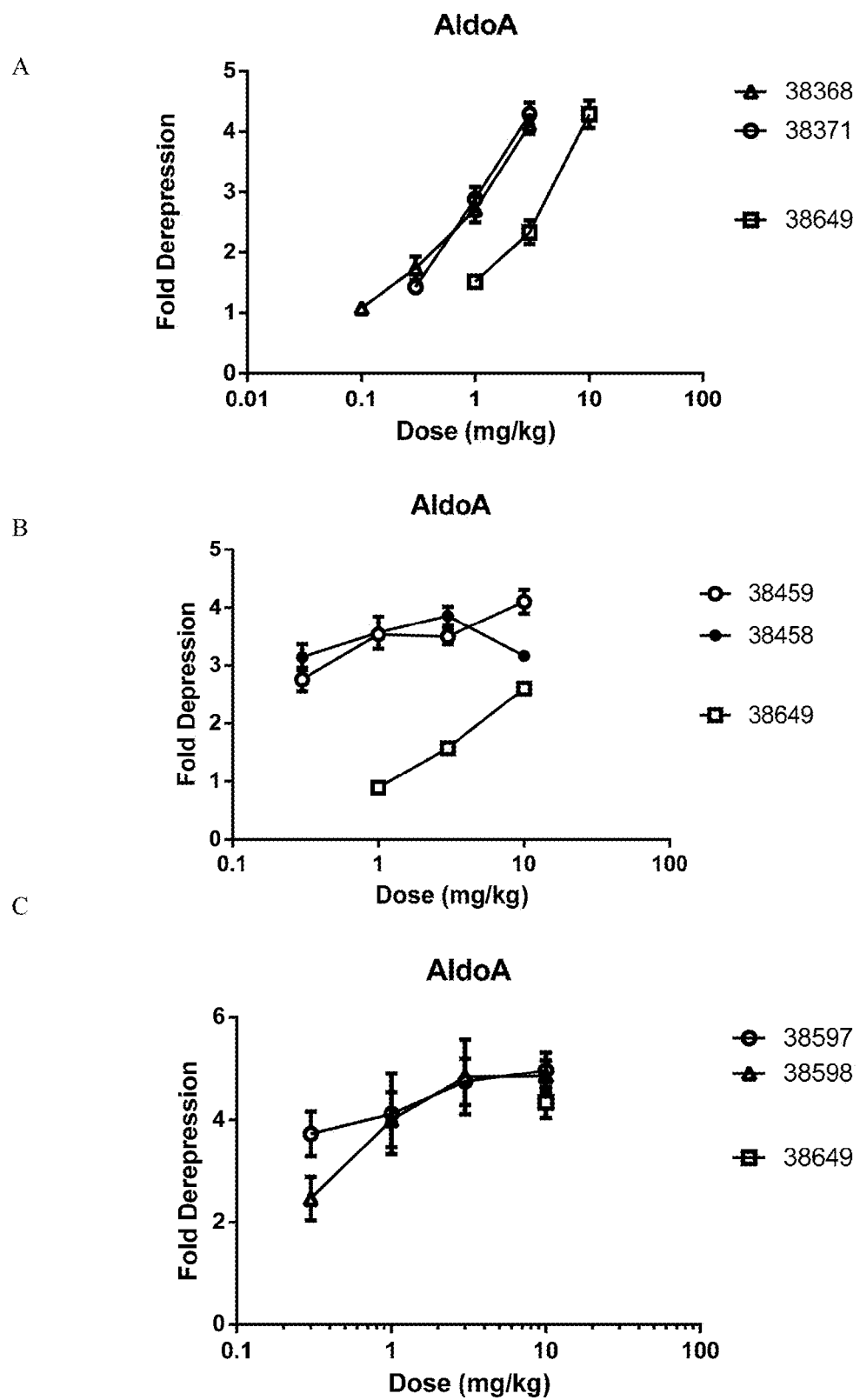
FIGS. 5A, 5B, and 5C. In vivo potency of GalNAc-conjugated anti-miR-122 modified oligonucleotides.
Figure 6:
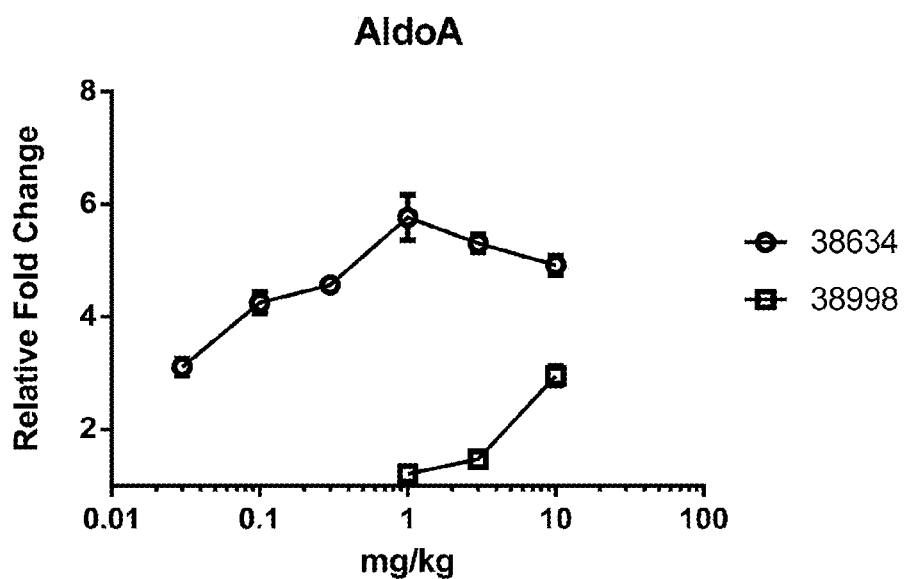
FIGS. 6A and 6B. In vivo potency of GalNAc-conjugated anti-miR-122 modified oligonucleotides.
Figure 6:
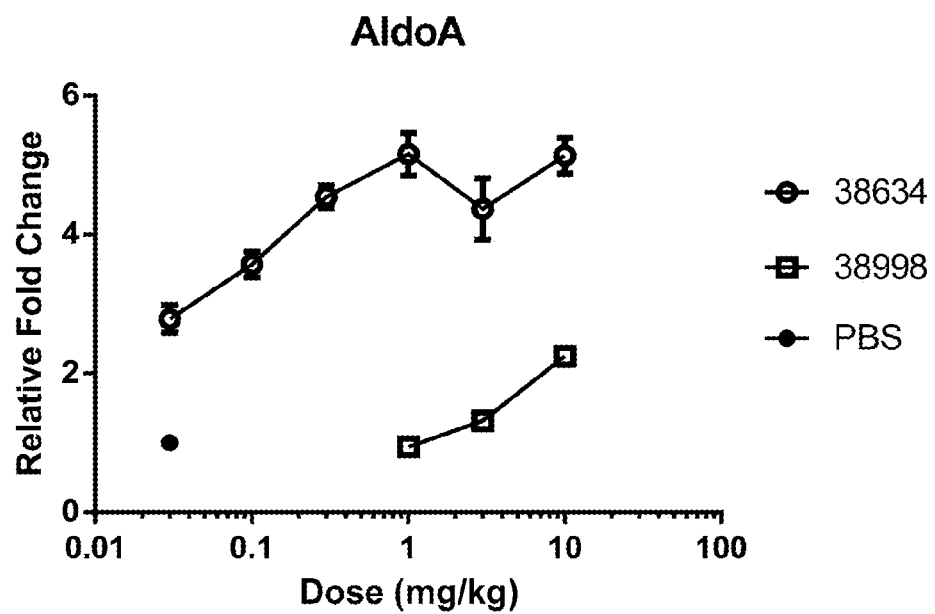
Figure 7:
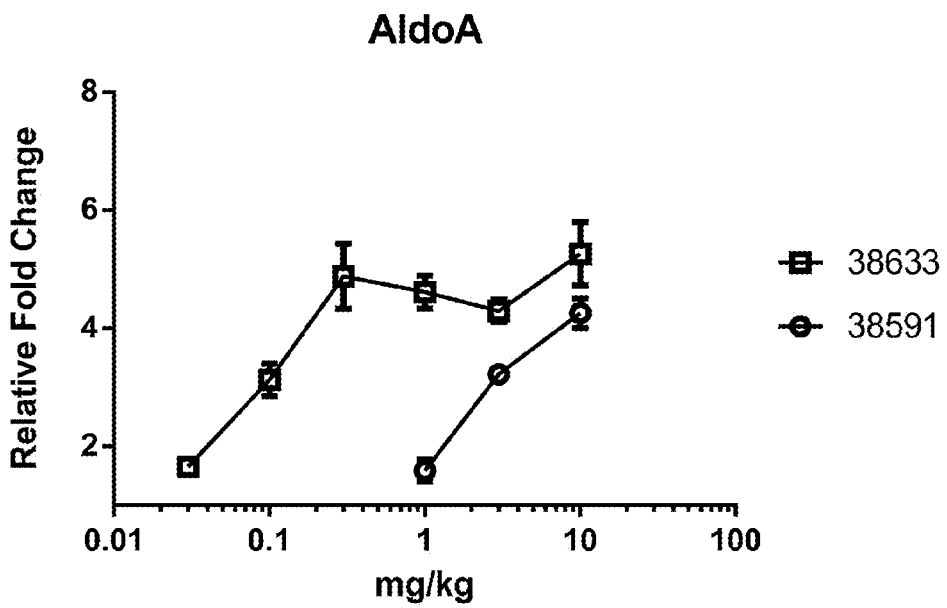
FIGS. 7A and 7B. In vivo potency of GalNAc-conjugated anti-miR-122 modified oligonucleotides.
Figure 7:

As shown in FIGS. 5A, 5B, and 5C, each of the three GalNAc-conjugated modified oligonucleotides in Table C was more potent than the unconjugated modified oligonucleotide. Compounds 38368 and 38371 exhibited an increase in potency of approximately 3-fold, relative to unconjugated 38649 (FIG. 5A). Compounds 38458 and 38459, each of which has a β-D-deoxyribonucleoside linking group, exhibited at least a 10-fold increase in potency (FIG. 5B). Compounds 38597 and 38598, each of which has a 2'-sugar modified linking group, also exhibited at least a 10-fold increase in potency (FIG. 5C). In additional studies, potency increases of up to 20-fold have been observed for compounds 38459, 38458, 38597, and 38598.

Also measured was the amount of unconjugated modified oligonucleotide in the liver and kidney tissue 7 days following a single subcutaneous dose of compounds 38368 and 38371 at doses of 1 mg/kg and 3 mg/kg, and compounds 38458 and 38459 at doses of 0.3 mg/kg, 1 mg/kg, and 3 mg/kg. Each sample was subjected to high-performance liquid chromatography time-of-flight mass spectrometry (HPLC-TOF MS) to measure oligonucleotide lengths and amounts. The lower limit of quantitation (LLOQ) by this method is 0.2-1.0 µg/g.

The GalNAc-conjugated modified oligonucleotides were found to have varying rates of formation of unconjugated modified oligonucleotide. For example, following administration of compound 38368, less than 10% of compound 38649 (the unconjugated modified oligonucleotide) was detected in the liver. Following administration of compound 38371, compound 38649 was not detected in the liver at either dose of compound 38371. Conversely, seven days following subcutaneous administration of compound 38459, the only unconjugated modified oligonucleotide species detected was unconjugated 38649; the parent compound 38459 was not detected. Following administration of compound 38458, unconjugated modified oligonucleotide was detected in two forms: 38649, as well as 38649-PO-A (a metabolite of compound 38458). This metabolite was detected at higher levels than unconjugated 38649.

Also measured was the amount of unconjugated modified oligonucleotide in the liver 24 hours following a single subcutaneous dose of compounds 38458 and 38459 at doses of 0.3 mg/kg, 1 mg/kg, and 3 mg/kg. Anti-miR levels were measured by LC-TOF. The lower limit of quantitation (LLOQ) by this method is 0.2-1.0 µg/g. It was observed that following administration of compound 38459, 90% of the total compound present in the liver was unconjugated compound 38649. Following administration of 38458, approximately 46% of total compound present in the liver was unconjugated compound 38649. Thus, unconjugated compound 38649 is released more rapidly from compound 38459 than from compound 38458.

Oligonucleotides generally accumulate to the highest levels in kidney tissue, followed by liver tissue. To determine whether the GalNAc conjugate altered the accumulation of compound in liver tissue compared to kidney tissue, relative to unconjugated compound, the amount of unconjugated 38649 was also measured in the kidney tissue. As described above, following administration of compound 38459, 100% of the total compound found in the liver is unconjugated 38649, indicating complete release of 38649 from the GalNAc-conjugated compound 38459. Following administration of compound 38459, compound 38649 accumulated less in the kidney relative to the liver, (i.e. exhibited a lower kidney:liver ratio), relative to accumulation of compound 38649 following administration of compound 38649. Thus, compound 38459 can preferentially deliver compound 38649 to the liver, while minimizing delivery to the kidney, as compared to unconjugated 38649.

The onset and duration of action for compound 38459 was evaluated in an in vivo study. Groups of mice were given a single, subcutaneous (SC) dose of compound 38459 at 0.1 mg/kg, 0.3 mg/kg, 1 mg/kg, and 3 mg/kg. An additional group of mice was administered unconjugated compound 38649 at a dose of 10 mg/kg. A group of animals from each treatment was sacrificed on each of days 1, 2, 3, 4, 5, 6, 14, 21, 28, and 56. RNA was isolated from liver and ALDOA mRNA levels were measured by real-time PCR. The mean ALDOA level for each group was calculated. The fold change relative to the control group (PBS-treated) is shown in Table D.

TABLE D

Onset and duration of action of compound 38459

| Days following single SC dose | Fold change in ALDOA | | | | |
|---|---|---|---|---|---|
| | 38459 3 mg/kg | 38459 1 mg/kg | 38459 0.3 mg/kg | 38459 0.1 mg/kg | 38649 10 mg/kg |
| 1 | 4.9 | 3.6 | 1.7 | 1.4 | 2.2 |
| 2 | 4.2 | 3.2 | 2.4 | 1.4 | 4.7 |
| 3 | 4.4 | 4.6 | 3.5 | 1.6 | 3.4 |
| 4 | 5.1 | 4.9 | 3.3 | 2.2 | 4.6 |
| 5 | 5.9 | 4.9 | 3.9 | 2.1 | 4.5 |
| 6 | 5.1 | 4.5 | 3.2 | 2.2 | 3.6 |
| 14 | 4.8 | 4.3 | 3.4 | 1.7 | 3.1 |
| 21 | 5.9 | 4.9 | 4.0 | 2.2 | 3.6 |
| 28 | 4.8 | 4.7 | 2.9 | 2.0 | 4.2 |
| 56 | 5.6 | 4.6 | 2.6 | 1.7 | 3.2 |

The data in Table D demonstrate that compound 38459, as well as compound 38649, has a rapid onset of action, as evidenced by ALDOA derepression as early as 1 day following a single dose of compound. Further, ALDOA derepression is maintained for at least 8 weeks following a single dose of compound.

These data demonstrate that the GalNAc-conjugated compound 38459, which is at least 10-fold more potent than the unconjugated 38649 compound, achieves this potency at significantly lower liver tissue concentrations, with preferential delivery to the liver tissue. Additionally, compound 38459 exhibits a rapid onset of action, and a duration of action of at least 8 weeks.

Example 2

Conjugated Shorter Modified Oligonucleotides

GalNAc-containing compounds were formed by conjugating a structure in FIG. 2 to the 3' end of the modified oligonucleotides shown in Table E. Sugar moieties, internucleoside linkages, and nucleobases are indicated as follows: nucleosides not followed by a subscript are β-D-deoxyribonucleosides; nucleosides followed by a subscript "S" are S-cEt nucleosides; and each internucleoside linkage is a phosphorothioate internucleoside linkage.

TABLE E

Unconjugated and Conjugated Modified Oligonucleotides

| Sequence and Modifications | Structure | SEQ ID |
|---|---|---|
| 38591 $U_STGU_SC_SAC_SAC_STC_SC_SA_S$ | Unconjugated | 6 |
| 38633 $U_STGU_SC_SAC_SAC_STC_SC_SA_S$ | Structure I of FIG. 2A, where $X_2$ is a phophodiester linkage, m is 1, $N_m$ is a β-D-deoxynucleoside (dA), $X_1$ is a phosphodiester linkage; MO is 38591 | 6 |
| 38998 $C_SA_SC_SA_SC_SU_SC_SC_S$ | Unconjugated | 1 |
| 38634 $C_SA_SC_SA_SC_SU_SC_SC_S$ | Structure I of FIG. 2A, where $X_2$ is a phophodiester linkage, m is 1, $N_m$ is a β-D-deoxynucleoside (dA), $X_1$ is a phosphodiester linkage; MO is 38998 | 1 |

To determine in vivo potency, the compounds were evaluated for their ability to de-repress the expression of liver aldolase A (ALDOA). Compounds were administered to mice, and ALDOA mRNA levels were measured, by quantitative PCR, in RNA isolated from liver. The fold change in ALDOA mRNA, relative to saline, was calculated to determine in vivo potency (FIGS. 6A and 6B and 7A and 7B). The ED50 (concentration of compound at which ALDOA derepression is 50% of maximum) and ED90 (concentration of compound at which ALDOA deprepression is 90% of maximum) calculated from the results of those experiments are shown in Table F and G.

TABLE F

In vivo potency of conjugated and unconjugated anti-miR-122 compounds

| Compound | ED50 (mg/kg) | Fold change | ED90 (mg/kg) | Fold change |
|---|---|---|---|---|
| Experiment 1 (FIG. 6A) | | | | |
| 38634 | 0.03 | 456 | 0.3 | 212 |
| 38998 | 13.7 | | 63.8 | |
| Experiment 2 (FIG. 6B) | | | | |
| 38634 | 0.04 | 290 | 0.43 | 99.3 |
| 38998 | 11.6 | | 42.7 | |

TABLE G

In vivo potency of conjugated and unconjugated anti-miR-122 compounds

| Compound | ED50 (mg/kg) | Fold change | ED90 (mg/kg) | Fold change |
|---|---|---|---|---|
| Experiment 1 (FIG. 7A) | | | | |
| 38633 | 0.08 | 27 | 0.25 | 26 |
| 38591 | 2.2 | | 6.62 | |
| Experiment 2 (FIG. 7B) | | | | |
| 38633 | 0.15 | 20 | 0.94 | 10 |
| 38591 | 3.0 | | 8.9 | |

As shown in Table F, GalNAc conjugation according to the present invention improved the ED50 and ED90 of an 8-mer anti-miR-122 compound by at least 100-fold. As shown in Table G, GalNAc conjugation according to the present invention improved the ED50 and ED90 of a 13-mer anti-miR-122 compound by at least 10-fold.

Derepression of another miR-122 target gene, CD320, was also determined for compounds 38634 and 38998. The results were similar to the results obtained for ALDOA shown in Table F: GalNAc conjugation according to the present invention improved the ED50 by 343-fold and 272-fold in experiments 1 and 2, respectively, and improved the ED90 by 492-fold and 545-fold in experiments 1 and 2, respectively.

Figure 8:
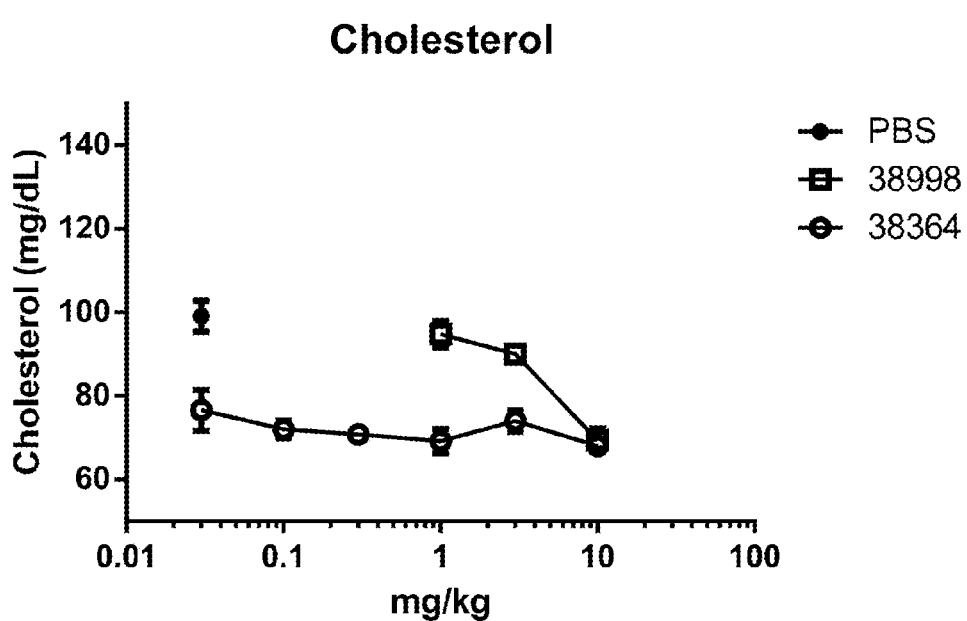
FIGS. 8A and 8B. In vivo potency of GalNAc-conjugated anti-miR-122 modified oligonucleotides.
Figure 8:
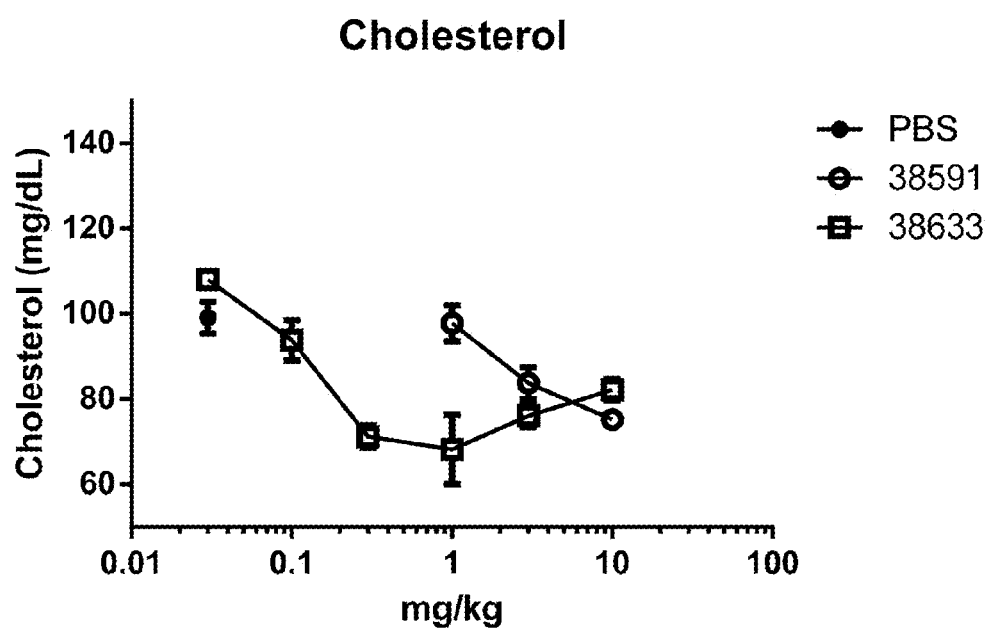

GalNAc conjugation described herein also improved cholesterol-lowering potency was also observed for the compounds comprising GalNAc. Exemplary results from experiment 1 are shown in FIGS. 8A and 8B. Compounds 38633 and 38634, which are GalNAc conjugates, were more potent than compounds 38591 and 38998, which lack GalNAc. Similar results were obtained for experiment 2 (data not shown).

Example 3

Conjugated RNaseH Modified Oligonucleotides

The GalNAc conjugation approach described herein also improved the potency of a modified oligonucleotide targeted to a protein-coding RNA. The oligonucleotide tested was a 5-10-5 2'-MOE modified 'gapmer' targeted to the PTEN mRNA. Hybridization of the gapmer modified oligonucleotide to the PTEN mRNA results in cleavage of the mRNA by RNaseH, thus reducing the level of PTEN mRNA. The potency of the compound is evaluated by its ability to reduce the level of PTEN mRNA.

GalNAc-containing compound was formed by conjugating a structure in FIG. 2 to the 3' end the modified oligonucleotide as shown in Table H.

TABLE H

Unconjugated and Conjugated Modified Oligonucleotides

| Sequence and Modifications | Structure | SEQ ID |
|---|---|---|
| 38631 $^{Me}C_ET_EG_E{}^{Me}C_ET_E$AGCCTCTGGAT$_ET_ET_EG_EA_E$ | Unconjugated | 7 |
| 38639 $^{Me}C_ET_EG_E{}^{Me}C_ET_E$AGCCTCTGGAT$_ET_ET_EG_EA_E$ | Structure I of FIG. 2A, where $X_2$ is a phophodiester linkage, m is 1, $N_m$ is a β-D-deoxynucleoside (A), $X_1$ is a phosphodiester linkage | 7 |

Sugar moieties, internucleoside linkages, and nucleobases are indicated as follows: the superscript "Me" indicate 5-methylcytosine; nucleosides not followed by a subscript are β-D-deoxyribonucleosides; nucleosides followed by a subscript "E" are 2'-O-methoxyethyl nucleosides; and each internucleoside linkage is a phosphorothioate internucleoside linkage.

A single dose of unconjugated compound was subcutaneously administered to mice (n=3) at doses of 1, 3, and 10 mg/kg. A single dose of conjugated compound was subcutaneously administered to mice (n=6) at doses of 0.03, 0.1, 0.3, 1, 3, and 10 mg/kg. Two days following administration, the study was terminated, and RNA was extracted from liver tissue collected from each animal. Quantitative PCR was performed to measure the level of PTEN mRNA. As shown in Table I, compound 38631 did not significantly reduced PTEN mRNA at any of the 3 doses tested. However, at doses of 3 and 10 mg/kg, The GalNAc-containing compound significantly reduced PTEN mRNA.

TABLE I

In vivo potency of conjugated and unconjugated PTEN modified oligonucleotides

| | % mRNA Level Relative to PBS | |
|---|---|---|
| Dose (mg/kg) | 38631 | 38639 |
| 10 | 84.4 | 39 |
| 3 | 122 | 52.4 |
| 1 | 87.2 | 98.8 |
| 0.3 | | 148.4 |
| 0.1 | | 121.2 |
| 0.03 | | 140.2 |

Example 4

Conjugated Modified Oligonucleotides

Anti-miR-21 modified oligonucleotides were conjugated to a GalNAc-containing moiety, to determine whether the conjugation would improve the potency of the oligonucleotides.

GalNAc-containing compounds were formed by conjugating the structure in FIG. 1 to the 3' end of the 36731 modified oligonucleotide. In compound 40601, the GalNAc-containing moiety is linked to the 3'-terminal nucleoside of 36731 through a β-D-deoxynucleoside, with a phosphodiester (PO) linkage between the 3'-terminal nucleoside of 36731 and the β-D-deoxynucleoside and a phosphodiester (PO) linkage between the β-D-deoxynucleoside (β-D-deoxyadenosine (A)) and the GalNAc-containing moiety, as shown in FIG. 2A, where $X_2$ is a phosphodiester linkage, m is 1, $N_m$ is a β-D-deoxynucleoside (A), $X_1$ is a phosphodiester linkage, and MO is compound 36731. In compound 40379, the GalNAc-containing moiety is linked to the 3'-terminal nucleoside of 36731 through a phosphodiester (PO) linkage between the 3'-terminal nucleoside of 36731 and the GalNAc-containing moiety, as shown in FIG. 2C, where X is a phosphodiester linkage, and MO is compound 36731.

40601:
(SEQ ID NO: 8)
$A_EC_SA_ET_EC_SA_EG_ET_EC_S$TGAU$_S$AAGC$_S$U$_S$A$_S$-PO-A-PO-GalNAc

40379:
(SEQ ID NO: 8)
$A_EC_SA_ET_EC_SA_EG_ET_EC_S$TGAU$_S$AAGC$_S$U$_S$A$_S$-PO-GalNAC

Figure 9A:
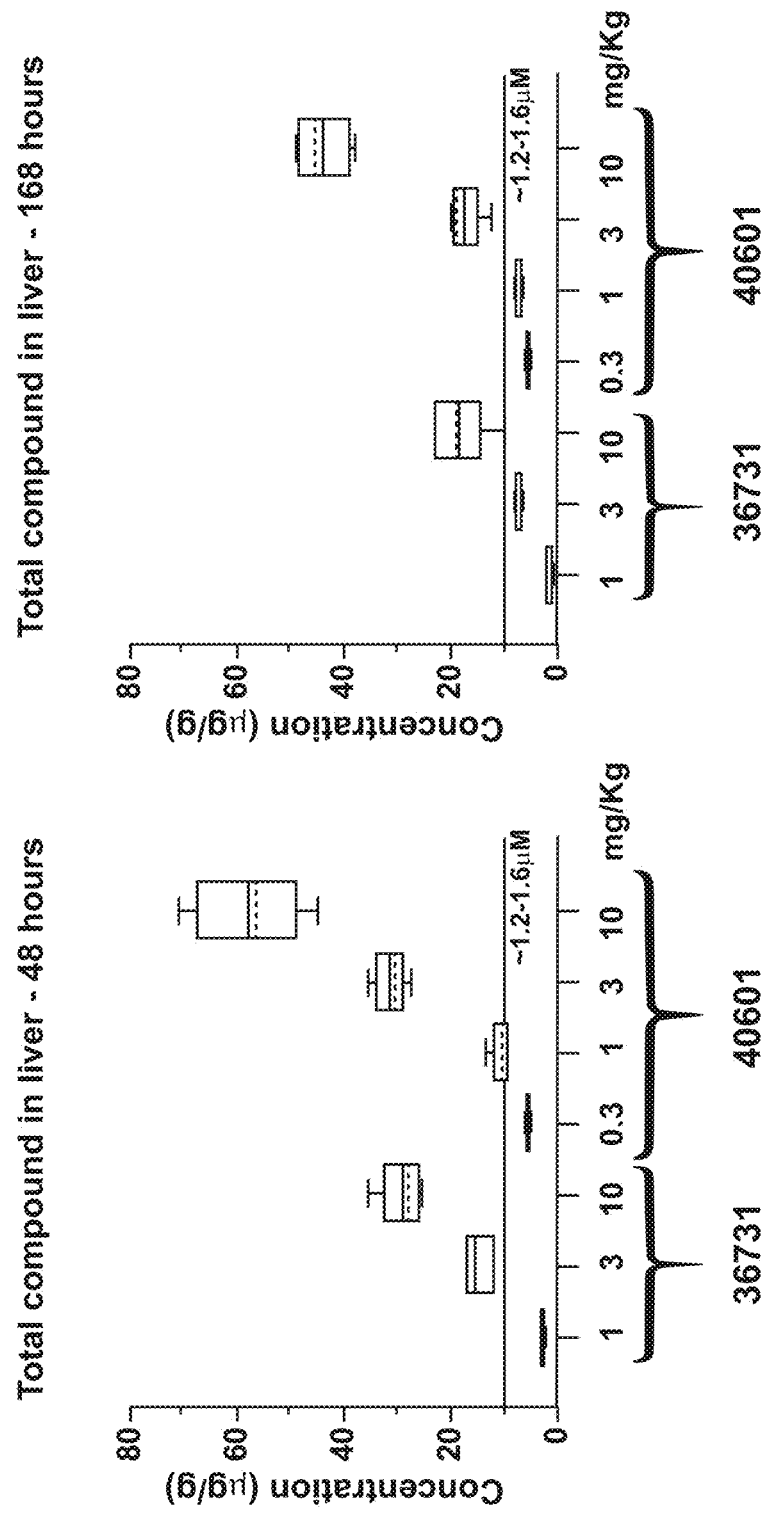
FIGS. 9A and 9B. Liver concentrations of GalNAc-conjugated anti-miR-21 modified oligonucleotides.

Liver concentrations of 36731 and 40601 were measured at 48 hours and 168 hours after a single subcutaneous dose of compound in three to five wild-type C7/Bl6 mice. The modified oligonucleotide portion of 36731 was dosed at 1 mg/kg, 3 mg/kg, and 10 mg/kg, and 40601 was dosed at 0.3 mg/kg, 1 mg/kg, 3 mg/kg, and 10 mg/kg. Each sample was subjected to liquid chromatography tandem mass spectrometry (LC-MS/MS) to measure oligonucleotide lengths and amounts. As shown in Table J and FIG. 9A, liver concentrations of modified oligonucleotide were significantly higher following administration of 40601 than following administration of a similar dose of 36731, at both time points. Each concentration of 40601 shown in FIG. 9A and Table J is the total concentration of all modified oligonucleotide-containing species detected by LC-MS/MS. Conjugation of modified oligonucleotide resulted in a dose-proportional increase in compound in the liver.

Figure 9B:
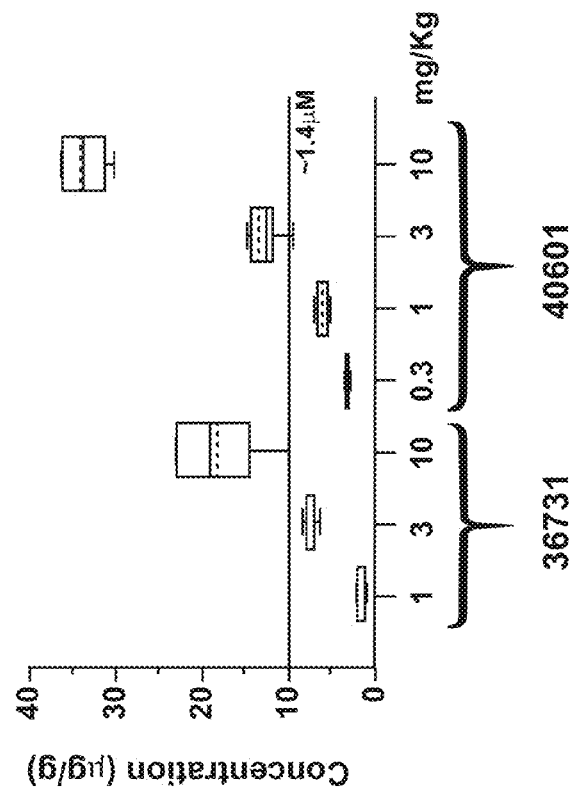
Figure 9B:
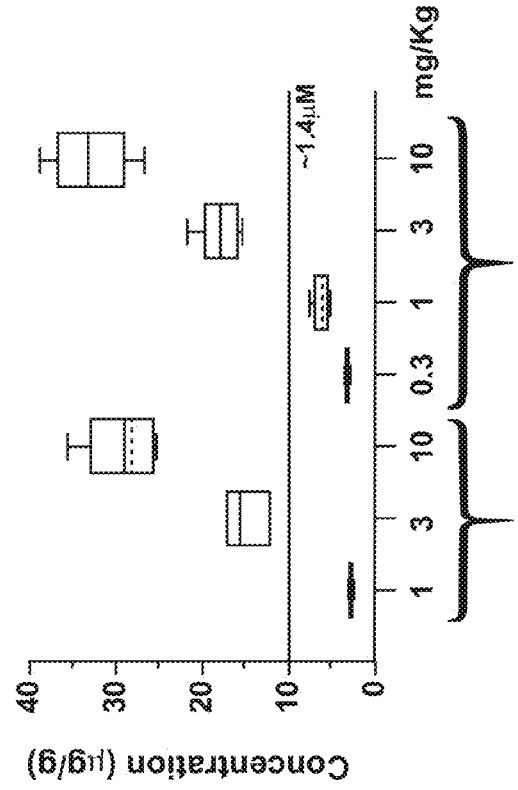

Metabolism of 40601 to release modified oligonucleotide 36731 was also evaluated. It was found that by 48 hours after a single subcutaneous administration of compound 40601, the dominant species identified by LC-MS/MS was 36731. Table J and FIG. 9B show the concentration of modified oligonucleotide 36731 in mouse livers following a single subcutaneous administration of compound 36731 or compound 40601. Table J shows the percentage of 36731 species detected in mouse liver following administration of 40601 (CV %=coefficient of variance).

TABLE J

Concentration of 36731 and 40601 in mouse liver after single SC dose

| Time after dosing | Compound dosed | Dose (μg/kg) | Total 40601 compound detected (μg/kg) | Mean 36731 detected (μg/kg) | CV % | % 36731 | N |
|---|---|---|---|---|---|---|---|
| 48 hours | 36731 | 1 | | 2.9 | 6 | | 5 |
| | | 3 | | 15.4 | 18.3 | | 3 |
| | | 10 | | 28.8 | 14.5 | | 5 |
| | 40601 | 0.3 | 5.5 | 3.1 | 5.2 | 57 | 5 |
| | | 1 | 10.6 | 6.3 | 15.4 | 60 | 5 |
| | | 3 | 30.9 | 17.5 | 14 | 57 | 5 |
| | | 10 | 57.6 | 32.7 | 13.7 | 57 | 5 |
| 168 hours | 36731 | 1 | | 1.9 | 32.1 | | 4 |
| | | 3 | | 7.6 | 8.9 | | 5 |
| | | 10 | | 18.6 | 28 | | 5 |
| | 40601 | 0.3 | 5.5 | 2.9 | 4.5 | 54 | 5 |
| | | 1 | 7.4 | 5.7 | 10.2 | 78 | 5 |
| | | 3 | 17.2 | 13.1 | 15.7 | 76 | 5 |
| | | 10 | 43.9 | 33.4 | 7.8 | 76 | 5 |

Liver concentration of 40379 was also measured at 48 hours and 168 hours after a single subcutaneous dose of compound in five wild-type C7/B16 mice. The compound was dosed at 0.3 mg/kg, 1 mg/kg, 3 mg/kg, and 10 mg/kg. Each sample was subjected to liquid chromatography tandem mass spectrometry (LC-MS/MS) to measure oligonucleotide lengths and amounts. As was observed for compound 40601, the liver concentrations of compound were significantly higher following administration of 40379 than following administration of a similar dose of 36731, at both time points. Conjugation of modified oligonucleotide resulted in a dose-proportional increase in compound in the liver. Metabolism of 40379 to release modified oligonucleotide 36731 was also evaluated. It was found that by 48 hours after a single subcutaneous administration of compound 40601, compound 36371 was present, but at lower concentrations relative to the amount of compound 36371 present following administration of compound 40379 (data not shown). Whereas at least 50% of compound 40601 was present as compound 36731 after 48 or 168 hours, approximately 15 to 30% of compound 40379 was present as compound 36731. Thus, while compound 40379 does undergo some metabolism that results in the release of unconjugated compound 36731, the release of unconjugated compound is less than that observed for compound 40601. These data suggest that the presence of the PO-A-PO linker facilates release of the unconjugated modified oligonucleotide from the GalNAc-containing compound.

To assess the effect of inhibition of miR-21 on known mRNA targets, de-repression of SPG20, Rnf167 and Taf7 in normal mouse liver was measured following a single dose of 36731 (1 and 10 mg/kg) or a single dose of 40601 (0.1, 1 and 10 mg/kg) administered to wild-type mice. Livers were harvested 4 or 7 days after administration. As shown in Table K, modest target gene derepression was observed for SPG20 and Taf7 seven days after a single dose of 36731, while Rnf167 was derepressed at both time points at the highest dose. Single dose administration of 40601 showed improved target derepression of both SPG20 and Taf7 at both time points and similar derepression of Rnf167. Improved target derepression included both larger fold change in target gene expression and earlier onset of derepression.

TABLE K

Derepression of miR-21 target genes in normal liver following administration of 36731 or 40601

| Treatment | Time Point | Dose | SPG20 | Rnf167 | Taf7 |
|---|---|---|---|---|---|
| Vehicle | | | 1.00 | 1.00 | 1.00 |
| 36731 | Day 4 | 1 mg/kg | 0.98 | 1.07 | 0.96 |
| | | 10 mg/kg | 0.97 | 1.29 | 1.02 |
| | Day 7 | 1 mg/kg | 1.11 | 0.91 | 1.21 |
| | | 10 mg/kg | 1.25 | 1.11 | 1.16 |
| 40601 | Day 2 | 10 mg/kg | 1.36 | 1.24 | 1.28 |
| | Day 4 | 0.1 mg/kg | 1.16 | 0.97 | 1.19 |
| | | 1 mg/kg | 1.32 | 0.97 | 1.12 |
| | | 10 mg/kg | 1.44 | 1.27 | 1.60 |
| | Day 7 | 0.1 mg/kg | 1.23 | 0.65 | 1.75 |
| | | 1 mg/kg | 1.70 | 1.04 | 2.49 |
| | | 10 mg/kg | 1.53 | 1.32 | 3.28 |

Delivery and efficacy of anti-miR-21 compounds were evaluated in a liver-specific doxycycline-regulated oncogene expression system, used to model hepatocellular carcinoma (HCC) in the mouse. In this model, transgenic mice express the oncogene H-rasG12V under the control of a doxycycline-repressable, liver-specific promoter (Tet-o-H-rasG12V; LAP-TTA; See, for example, Lim et al., Hepatology, 2013). When doxycycline is removed, H-rasG12V transgene expression is activated in the liver and the mice develop liver tumors. It was confirmed that expression of the GalNAc receptors ASGR1 and ASGR2 remains high for at least 6 weeks following removal of doxycycline, while miR-21 expression increases with the onset of morphologically detectable disease (data not shown).

In order to demonstrate delivery of compounds 40601 and 36731 to liver tumors, the compounds were administered to mice 4 weeks after removal of doxycycline, by which time the mice have a significant tumor burden. The concentrations of 36731 and 40601 in liver tumor tissue (whole liver containing tumor) were measured at 168 hours after two doses of compound in five mice per group. The first dose was given at 0 hours, the second dose at 72 hours and tumor tissue harvested at 168 hours. Compound 36731 was administered at 10 mg/kg, while compound 40601 was administered at 0.1, 1, and 10 mg/kg. As shown in Table L, total drug level achieved was 80% greater for 40601 as compared to 36731. Release of 36731 modified oligonucleotide from compound 40601 was between 44 and 70% of the total.

TABLE L

Quantification of 36731 and 40601 in mouse liver tumor tissue following administration

| | | 36731 | | 40601 | | |
|---|---|---|---|---|---|---|
| Cmpd admin.: | | 36731 | | 36731 | | All |
| Cmpd detected: | | Mean | | Mean | | Mean |
| Dose (μg/kg) | Total dose (μg/kg) | detected (μg/kg) | CV % | detected (μg/kg) | CV % | % 36731 | detected (μg/kg) | CV % |
| 0.1 BIW | 0.2 | | | 1.7 | 18 | 63 | 2.7 | 28 |
| 1 BIW | 2 | | | 4.9 | 35 | 70 | 7 | 32 |
| 10 BIW | 20 | 23.3 | 38 | 17.9 | 35 | 44 | 40.5 | 33 |

Target derepression for the three miR-21 target genes evaluated in normal liver was also evaluated in the liver tumor tissue. Although statistical significance was not achieved, there was a trend towards derepression in treated liver tumor tissue as compared to vehicle. Table M shows derepression of SPG21, Rnf167, and Taf7 in liver tumor tissue following administration of compound 40601 or compound 36731.

TABLE M

Derepression of miR-21 target genes in liver tumor tissue following administration of 36731 or 40601

| | Average target gene level | | |
|---|---|---|---|
| Treatment | SPG20 | Rnf167 | Taf7 |
| Vehicle | 1.00 | 1.00 | 1.00 |
| 36731 10 mg/kg | 1.01 | 1.37 | 1.72 |
| 40601 10 mg/kg | 1.24 | 1.52 | 1.56 |
| 40601 1 mg/kg | 1.31 | 1.50 | 1.12 |
| 40601 0.1 mg/kg | 0.84 | 1.28 | 0.78 |

In addition, AFP levels in liver tumor tissue were evaluated following administration of compound 40601 or compound 36731. There was a trend toward reduced AFP levels in the mice that received a biweekly dose of 10 mg/kg 40601.

Next, efficacy of compounds 40601 and 36731 was tested in the Tet-o-H-rasG12V; LAP-TTA transgenic mice. Tumor progression was initiated by removing doxycycline from male mice at 6 weeks of age. After two weeks off doxycycline, mice were divided into 5 treatment groups: vehicle, 36731 25 mg/kg biweekly (BIW), 40601 25 mg/kg BIW, 40601 25 mg/kg once weekly (Q7D), and 40601 5 mg/kg BIW. Mice were treated for 4 weeks. Liver morphology (mottled appearance) was used as an indicator of tumor formation and was scored at the end of study by an investigator blinded to the treatment group. As shown in Table N, the majority (6/8) of the animals in the vehicle group had mottled livers, while approximately half (5/9) of the animals in the 25 mg/kg 36731 BIW group had mottled livers. A greater reduction in the incidence of mottled appearance was seen in the BIW dosing groups of compound 40601, with 3/8 in the 25 mg/kg 40601 BIW group and 2/8 in the 5 mg/kg 40601 BIW groups showing mottled livers. Once weekly dosing of 25 mg/kg 40601 resulted in a similar mottled appearance frequency (8/10) to vehicle.

TABLE N

Incidence of mottled livers in transgenic mice following administration of 36731 or 40601

| Compound | Dose | Total mice | # mottled livers | # not mottled livers |
|---|---|---|---|---|
| vehicle | | 8 | 6 | 2 |
| 36731 | 25 mg/kg BIW | 9 | 5 | 4 |
| 40601 | 5 mg/kg BIW | 8 | 2 | 6 |
| 40601 | 25 mg/kg BIW | 8 | 3 | 5 |
| 40601 | 25 mg/kg Q7D | 10 | 8 | 2 |

At the end of the study, liver tumor tissue AFP was assessed as a marker of liver tumors in the samples by Western blot analysis, normalized to β-actin. As shown in Table O, AFP was significantly reduced by treatment with 25 mg/kg 40601 BIW.

TABLE O

AFP levels in liver tumors of transgenic mice following administration of 36731 or 40601

| Treatment | Dose | Frequency | AFP Average |
|---|---|---|---|
| Vehicle | | | 0.09 |
| 36731 | 25 mg/kg | BIW | 0.08 |
| 40601 | 25 mg/kg | BIW | 0.03 |
| 40601 | 5 mg/kg | BIW | 0.06 |
| 40601 | 25 mg/kg | Q7D | 0.07 |

Target derepression following 36731 or 40601 administration was assessed in the liver tumor tissue of the transgenic mice. As shown in Table P, both SPG20 and Rnf167 transcripts were derepressed in the end of study samples from the 36731 and 40601 BIW dosing groups. Taf7 was also evaluated but did not show consistent derepression (data not shown).

TABLE P

SPG20 and Rnf167 target derepression in liver tumors of transgenic mice following administration of 36731 or 40601

| Treatment | Dose | Frequency | SPG20 Average | Rnf167 Average |
|---|---|---|---|---|
| Vehicle | | | 1.00 | 1.00 |
| 36731 | 25 mg/kg | BIW | 1.75 | 2.01 |
| 40601 | 25 mg/kg | BIW | 1.59 | 2.44 |
| 40601 | 5 mg/kg | BIW | 1.51 | 2.09 |
| 40601 | 25 mg/kg | Q7D | 1.33 | 1.78 |

Finally, tumor drug concentrations were evaluated at the end of the study. As shown in Table Q, comparable levels of 36731 and total 40601 were achieved. Release of 36731 modified oligonucleotide from 40601 was approximately 50% of the total at all three doses.

TABLE Q

Quantification of 36731 and 40601 in liver tumor tissue following administration

| Cmpd admin.: | | 36731 | | | 40601 | | | | |
|---|---|---|---|---|---|---|---|---|---|
| Cmpd detect.: | | 36731 | | | 36731 | | | All | |
| Dose (μg/kg) | Total dose (μg/kg) | Mean detected (μg/kg) | CV % | Mean detected (μg/kg) | CV % | % 36731 | Mean detected (μg/kg) | CV % |
| 5 BIW x4 | 40 | | | 28.4 | 28 | 49 | 58.3 | 29.4 |
| 25 QW x4 | 100 | | | 37.9 | 23 | 41 | 92.2 | 24.6 |
| 25 BIW x4 | 200 | 233.5 | 37 | 96.0 | 31 | 49 | 197.1 | 30.5 |

To evaluate whether there was impact on efficacy parameters starting treatment with more advanced disease, a study with a comparable design was initiated, except treatment was started at 4 weeks after removal of doxycycline and the mice were only treated for three weeks. In this experiment, the once per week dosing group was not included. AFP and target gene assessment was measured at the end of the study. A trend towards reduced AFP levels in the high dose group of 40601, 25 mg/kg BIW, was observed (data not shown). Target engagement was also observed in the treatment groups, reaching statistical significance with Taf7 at 25 mg/kg of 36731 and 40601 (data not shown).

As demonstrated herein, conjugation of a modified oligonucleotide to a GalNAc-containing moiety results in improved potency of the modified oligonucleotide. Potency can be further improved by attaching the GalNAc-containing moiety to the modified oligonucleotide through a nucleoside linking group, for example as shown in FIGS. 2A and 2B. Additionally, use of a nucleoside linking group yields more complete release of the unconjugated modified oligonucleotide from the conjugated structure.

Example 5

Conjugated Shorter Modified Oligonucleotides

Cholesterol-containing compounds were formed by conjugating cholesterol to the 3' end of the modified oligonucleotides shown in Table R. Sugar moieties, internucleoside linkages, and nucleobases are indicated as follows: nucleosides not followed by a subscript are β-D-deoxyribonucleosides; nucleosides followed by a subscript "S" are S-cEt nucleosides; and each internucleoside linkage is a phosphorothioate internucleoside linkage, except the internucleoside linkages indicated by subscript (O), which are phosphodiester linkages.

TABLE S

In vivo potency of conjugated and unconjugated anti-miR-122 compounds

| Compound | ED50 (mg/kg) | Fold change | ED90 (mg/kg) | Fold change |
|---|---|---|---|---|
| 38070 | 0.08 | 78.8 | 1.27 | 31.6 |
| 38998 | 6.3 | | 40.1 | |

As shown in Table S, cholesterol conjugation according to the present invention improved the $ED_{50}$ and $ED_{90}$ of an 8-mer anti-miR-122 compound by at least 30-fold.

Derepression of another miR-122 target gene, CD320, was also determined for compounds 38070 and 38998. The results were similar to the results obtained for ALDOA (data not shown).

Cholesterol conjugation described herein also improved cholesterol-lowering potency. At most concentrations tested, compound 38070 reduced cholesterol to a greater extent than the same concentration of compound 38998 (data not shown).

TABLE R

Unconjugated and Conjugated Modified Oligonucleotides

| Sequence and Modifications | Structure | SEQ ID NO |
|---|---|---|
| 38998 $C_SA_SC_SA_SC_SU_SC_SC_S$ | Unconjugated | 1 |
| 38070 $C_SA_SC_SA_SC_SU_SC_SC_S$ | 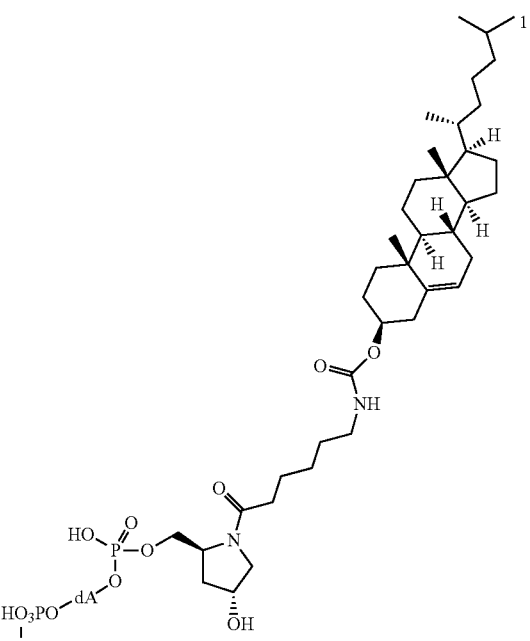 | 1 |

MO is $C_SA_SC_SA_SC_SU_SC_SC_S$

To determine in vivo potency, the compounds were evaluated for their ability to de-repress the expression of liver aldolase A (ALDOA). Compounds were administered to mice, and ALDOA mRNA levels were measured, by quantitative PCR, in RNA isolated from liver. The fold change in ALDOA mRNA, relative to saline, was calculated to determine in vivo potency. The ED50 (concentration of compound at which ALDOA derepression is 50% of maximum) and ED90 (concentration of compound at which ALDOA derepression is 90% of maximum) calculated from the results of those experiments are shown in Table S.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

What is claimed:

1. A compound comprising the structure:

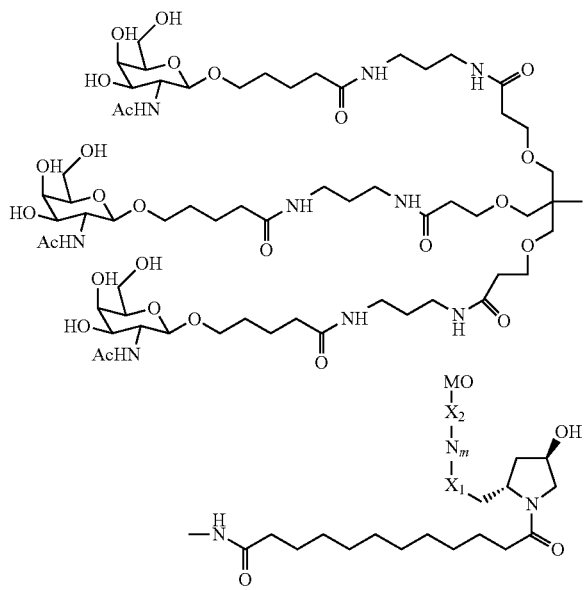

(I)

wherein each N of $N_m$ is, independently, a modified or unmodified nucleoside and m is from 1 to 5; $X_1$ and $X_2$ are each, independently, a phosphodiester linkage or a phosphorothioate linkage; and MO is a modified oligonucleotide; and wherein when m is greater than 1, each modified or unmodified nucleoside of $N_m$ is connected to adjacent modified or unmodified nucleosides of $N_m$ by a phosphodiester internucleoside linkage or a phosphorothioate internucleoside linkage.

2. The compound of claim 1, wherein at least one of $X_1$ and $X_2$ is a phosphodiester linkage.

3. The compound of claim 1, wherein each of $X_1$ and $X_2$ is a phosphodiester linkage.

4. The compound of claim 1, wherein m is 1, 2, or 3.

5. The compound of claim 1, wherein $N_m$ is $N'_pN''$, wherein each N' is, independently, a modified or unmodified nucleoside and p is from 0 to 4; and N'' is a nucleoside comprising an unmodified sugar moiety; and wherein each pair of adjacent N' nucleosides are connected by a phosphodiester internucleoside linkage or a phosphorothioate internucleoside linkage and N'' is connected to an adjacent N' by a phosphodiester internucleoside linkage or a phosphorothioate internucleoside linkage.

6. The compound of claim 5, wherein p is 0, 1, 2, 3, or 4.

7. The compound of claim 6, wherein p is 1, 2, 3, or 4 and each N of $N_m$ is linked by a phosphodiester internucleoside linkage.

8. The compound of claim 5, wherein each N' comprises an unmodified sugar moiety.

9. The compound of claim 5, wherein N'' is a β-D-deoxyriboadenosine or a β-D-deoxyriboguanosine.

10. The compound of claim 1, wherein the sugar moiety of each N of $N_m$ is independently selected from a β-D-ribose, a β-D-deoxyribose, a 2'-O-methoxy sugar, a 2'-O-methyl sugar, a 2'-fluoro sugar, and a bicyclic sugar moiety.

11. The compound of claim 1, wherein the nucleobase sequence of the modified oligonucleotide is complementary to a target RNA.

12. The compound of claim 11, wherein the target RNA is selected from a microRNA, a messenger RNA, a pre-messenger RNA, and a long non-coding RNA.

13. The compound of claim 12, wherein the modified oligonucleotide is hybridized to a second modified oligonucleotide, wherein the nucleobase sequence of the second modified oligonucleotide is complementary to the nucleobase sequence of the modified oligonucleotide.

14. The compound of claim 11, wherein the target RNA is a human target RNA.

15. The compound of claim 1, wherein the nucleobase sequence of the modified oligonucleotide is at least 90% identical to the nucleobase sequence of a microRNA.

16. The compound of claim 15, wherein the microRNA is a human microRNA.

17. The compound of claim 1, wherein the modified oligonucleotide consists of 8 to 25 linked nucleosides.

18. The compound of claim 1, wherein the modified oligonucleotide comprises at least one nucleoside with a modified sugar moiety.

19. The compound of claim 18, wherein each modified sugar moiety is independently selected from a 2'-O-methyl sugar moiety, a 2'-O-methoxyethyl sugar moiety, a 2'-fluoro sugar moiety, and a bicyclic sugar moiety.

20. The compound of claim 19, wherein each bicyclic sugar moiety is independently selected from a cEt sugar moiety and an LNA sugar moiety.

21. The compound of claim 1, wherein each nucleoside of the modified oligonucleotide comprises a modified sugar moiety.

22. The compound of claim 1, wherein the modified oligonucleotide comprises a plurality of nucleosides with a modified sugar moiety, and a plurality of nucleosides with an unmodified sugar moiety.

23. The compound of claim 1, wherein the modified oligonucleotide comprises a plurality of non-bicyclic nucleosides and a plurality of bicyclic nucleosides.

24. The compound of claim 1, wherein at least one linkage of the modified oligonucleotide is a modified internucleoside linkage.

25. A process of making a compound comprising the structure

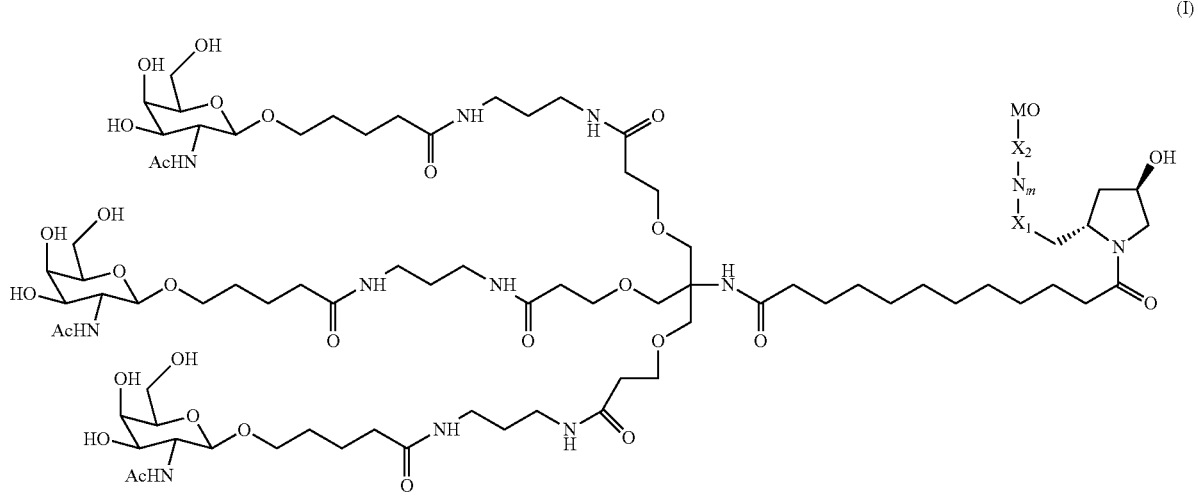

(I)

wherein each N of $N_m$ is, independently, a modified or unmodified nucleoside and m is from 1 to 5; $X_1$ and $X_2$ are each, independently, a phosphodiester linkage or a phosphorothioate linkage; wherein when m is greater than 1, each modified or unmodified nucleoside of $N_m$ is connected to adjacent modified or unmodified nucleosides of $N_m$ by a phosphodiester internucleoside linkage or a phosphorothioate internucleoside linkage; and MO is a modified oligonucleotide, the process comprising the steps of:
providing a solid support containing a conjugate as shown in formula IV;

(IV)
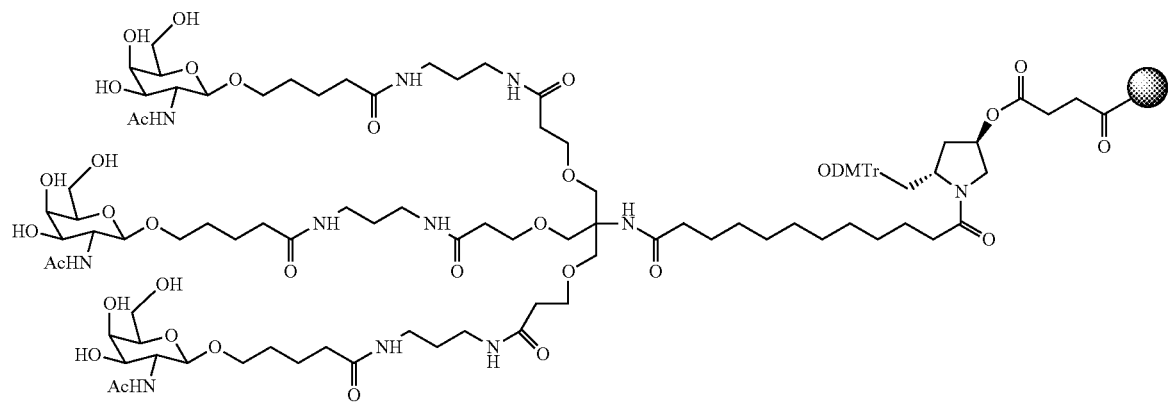
deprotecting the DMTr group under conditions effective to produce a reactive hydroxyl;
performing sequential phosphoramidite coupling steps to form $N_m$;
performing sequential phosphoramidite coupling steps to form the modified oligonucleotide; and
releasing the conjugated modified oligonucleotide from the solid support.
* * * * *

UNITED STATES PATENT AND TRADEMARK OFFICE
CERTIFICATE OF CORRECTION

PATENT NO. : 9,506,030 B2  
APPLICATION NO. : 14/266127  
DATED : November 29, 2016  
INVENTOR(S) : Balkrishen Bhat Page 1 of 2

It is certified that error appears in the above-identified patent and that said Letters Patent is hereby corrected as shown below:

In the Claims

Claim 1, Column 71, Lines 32-56, replace the structure with the following structure:

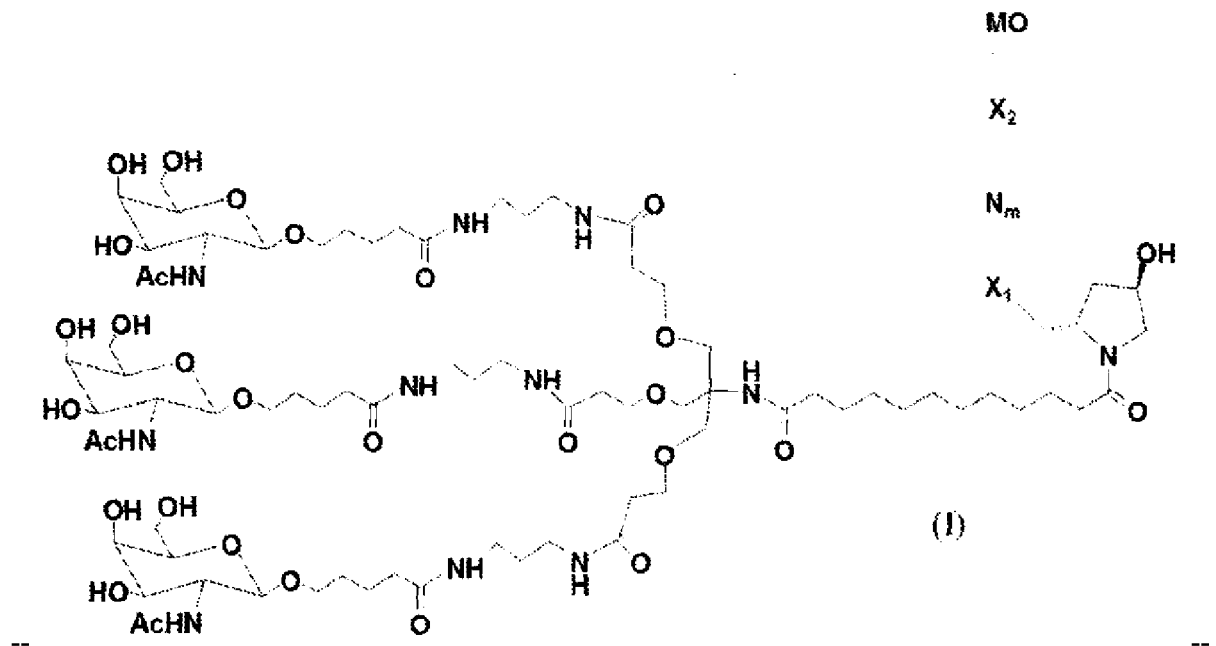

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 9,506,030 B2

Columns 75-76, Lines 1-19, replace the structure with the following structure:

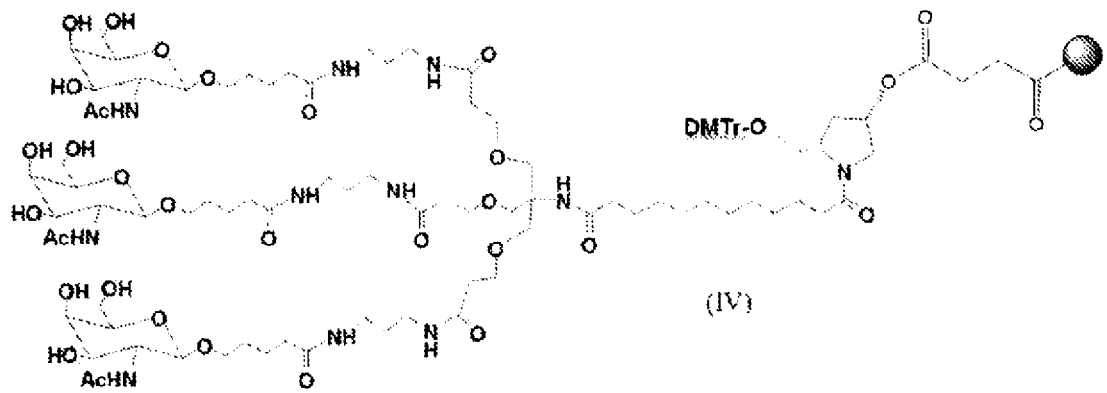

(IV)

SEQUENCE LISTING

```
<160> NUMBER OF SEQ ID NOS: 8

<210> SEQ ID NO 1
<211> LENGTH: 8
<212> TYPE: DNA
<213> ORGANISM: Artificial sequence
<220> FEATURE:
<223> OTHER INFORMATION: Synthetic

<400> SEQUENCE: 1 cacactcc                                                                    8

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
acaccattgt cacactcca                                                       19

<210> SEQ ID NO 3
<211> LENGTH: 18
<212> TYPE: DNA
<213> ORGANISM: Artificial sequence
<220> FEATURE:
<223> OTHER INFORMATION: Synthetic

<400> SEQUENCE: 3
acaccatgtc acactcca                                                        18

<210> SEQ ID NO 4
<211> LENGTH: 15
<212> TYPE: DNA
<213> ORGANISM: Artificial sequence
<220> FEATURE:
<223> OTHER INFORMATION: Synthetic

<400> SEQUENCE: 4
ccattgtcac actcc                                                           15

<210> SEQ ID NO 5
<211> LENGTH: 17
<212> TYPE: DNA
<213> ORGANISM: Artificial sequence
<220> FEATURE:
<223> OTHER INFORMATION: Synthetic

<400> SEQUENCE: 5
acaccattgc acactcc                                                         17

<210> SEQ ID NO 6
<211> LENGTH: 13
<212> TYPE: DNA
<213> ORGANISM: Artificial sequence
<220> FEATURE:
<223> OTHER INFORMATION: Synthetic

<400> SEQUENCE: 6
ttgtcacact cca                                                             13
```

```
<210> SEQ ID NO 7
<211> LENGTH: 21
<212> TYPE: DNA
<213> ORGANISM: Artificial sequence
<220> FEATURE:
<223> OTHER INFORMATION: Synthetic

<400> SEQUENCE: 7
ctcgctagcc tctggatttg a                                              21

<210> SEQ ID NO 8
<211> LENGTH: 19
<212> TYPE: DNA
<213> ORGANISM: Artificial sequence
<220> FEATURE:
<223> OTHER INFORMATION: Synthetic

<400> SEQUENCE: 8
acatcagtct gataagcta                                                 19
```